(12) United States Patent
Lipke et al.

(10) Patent No.: US 11,166,920 B2
(45) Date of Patent: Nov. 9, 2021

(54) MICROFLUIDICS DEVICE FOR FABRICATION OF LARGE, UNIFORM, INJECTABLE HYDROGEL MICROPARTICLES FOR CELL ENCAPSULATION

(71) Applicant: Auburn University, Auburn, AL (US)

(72) Inventors: Elizabeth A. Lipke, Auburn, AL (US);
Wen Jun Seeto, Auburn, AL (US);
Yuan Tian, Auburn, AL (US)

(73) Assignee: Auburn University, Auburn, AL (US)

( * ) Notice: Subject to any disclaimer, the term of this patent is extended or adjusted under 35 U.S.C. 154(b) by 333 days.

(21) Appl. No.: 16/153,095

(22) Filed: Oct. 5, 2018

(65) Prior Publication Data

US 2019/0105279 A1  Apr. 11, 2019

Related U.S. Application Data

(60) Provisional application No. 62/568,652, filed on Oct. 5, 2017.

(51) Int. Cl.
*A61K 9/50* (2006.01)
*C12N 5/074* (2010.01)
(Continued)

(52) U.S. Cl.
CPC .......... *A61K 9/5089* (2013.01); *A61K 9/0019* (2013.01); *A61K 9/06* (2013.01);
(Continued)

(58) Field of Classification Search
None
See application file for complete search history.

(56) References Cited

U.S. PATENT DOCUMENTS 8,563,325 B1 * 10/2013 Bartsch ............. B01L 3/502776
436/180
2003/0201022 A1 * 10/2003 Kawai ................. B01F 13/0059
137/828

(Continued)

OTHER PUBLICATIONS

Hong et al. "Bio-electrospraying and droplet-based microfluidics: control of cell numbers within living residues." Biomed. Mater. 5 (2010), 6 pages. (Year: 2010).*

(Continued)

*Primary Examiner* — William H. Beisner
(74) *Attorney, Agent, or Firm* — Meunier Carlin & Curfman LLC

(57) ABSTRACT

The devices, methods, and compositions disclosed herein accomplish robust cell encapsulation in polymer microparticles using a vertically oriented microfluidic device. A hydrophilic polymer precursor solution is flowed into a first inlet channel, which extends inward from an upper surface of the device housing. A hydrophobic fluid is flowed into a second inlet channel, which extends inward from a lower surface of the device housing. The two inlet channels meet at a junction, and an outlet channel extends away from the two inlet channels. When the two inwardly flowing streams meet at the junction, the polymer precursor solution disperses into the hydrophobic fluid. The dispersed precursor droplets are photopolymerized into microparticles as they travel through the outlet channel. The resulting microparticles are highly uniform, and are larger than conventionally formed microparticles. Cells of varying types can be encapsulated with high viability and spatial uniformity.

17 Claims, 35 Drawing Sheets

(51) Int. Cl.

| | |
|---|---|
| *C12M 3/06* | (2006.01) |
| *C12N 5/071* | (2010.01) |
| *C12N 5/00* | (2006.01) |
| *C12M 1/12* | (2006.01) |
| *A61P 9/00* | (2006.01) |
| *A61K 9/06* | (2006.01) |
| *A61K 9/00* | (2006.01) |
| *A61K 35/44* | (2015.01) |
| *A61K 35/545* | (2015.01) |
| *A61K 35/34* | (2015.01) |
| *C12M 1/00* | (2006.01) |

(52) U.S. Cl.
CPC .......... *A61K 9/5052* (2013.01); *A61K 35/34* (2013.01); *A61K 35/44* (2013.01); *A61K 35/545* (2013.01); *A61P 9/00* (2018.01); *C12M 3/065* (2013.01); *C12M 23/34* (2013.01); *C12N 5/0012* (2013.01); *C12N 5/069* (2013.01); *C12N 5/0696* (2013.01); *C12M 25/10* (2013.01); *C12M 25/16* (2013.01)

(56) References Cited

U.S. PATENT DOCUMENTS

| | | | | |
|---|---|---|---|---|
| 2005/0103690 | A1* | 5/2005 | Kawano | G01N 15/1484 209/576 |
| 2006/0003439 | A1* | 1/2006 | Ismagilov | B01L 3/0293 435/287.2 |

OTHER PUBLICATIONS

Abate, et al., "Synthesis of Monodisperse Microparticles from Non-Newtonian Polymer Solutions with Microfluidic Devices", Adv. Mat., 2011, 4 pages.

Ahmed Shama, "Study of Microfluidic Mixing and Droplet Generation for 3D Printing of Nuclear Fuels", École Polytechnique Fédérale de Lausanne, 2017, 74 pages.

Atwood et al., "Microencapsulation of Cells" University of Wisconsin—Madison Dec. 7, 2005, 30 pages.

Barron, et al., "Alginate-based microcapsules generated with the coaxial electrospray method for clinical application." J Biomater Sci Polym Ed, 1, 2017.

Bidarra, et al., "Injectable alginate hydrogels for cell delivery in tissue engineering". Acta Biomaterialia 10, 1646, 2014.

Chan, et al., "Efficient One-Step Production of Microencapsulated Hepatocyte Spheroids with Enhanced Functions." Small. 2016, 2720-2730.

Dendukuri, et al., "Continuous-flow lithography for high-throughput microparticle synthesis", Nat Mater, 2006, 5, 365-369.

Franco, et al., "Development and optimization of a dual-photoinitiator, emulsion-based technique for rapid generation of cell-laden hydrogel microspheres", 2011, 7, 3267-3276.

Guo, et al., "Droplet microfluidics for high-throughput biological assays.", Lab on a Chip, 2012, 12, 2146-2155.

Headen, et al. "Microfluidic-Based Generation of Size-Controlled, Biofunctionalized Synthetic Polymer Microgels for Cell Encapsulation", Advanced Materials 2014;26(19):3003-3008.

Jiang, et al., "Cell-laden microfluidic microgels for tissue regeneration". Lab Chip 16, 4482, 2016.

Kerscher, et al., "Direct hydrogel encapsulation of pluripotent stem cells enables ontomimetic differentiation and growth of engineered human heart tissues." Biomaterials. 2015;83:383-395.

Lee, et al., "High Throughput Synthesis of Uniform Biocompatible Polymer Beads with High Quantum Dot Loading Using Microfluidic Jet-Mode Breakup", Langmuir 2014, 2216-2221.

Nunes, et al., "Dripping and jetting in microfluidic multiphase flows applied to particle and fiber synthesis", J Phys D Appl Phys. Mar. 20, 2013; 46(11): 114002.

Olabisi, R.M. "Cell microencapsulation with synthetic polymers." Journal of Biomedical Materials Research Part a 103, 846, 2015.

Olabisi, et al., "Hydrogel Microsphere Encapsulation of a Cell-Based Gene Therapy System Increases Cell Survival of Injected Cells, Transgene Expression, and Bone Volume in a Model of Heterotopic Ossification", Tissue engineering. Part A, 2010, 16, 3727-3736.

Panda, et al., "Stop-flow lithography to generate cell-laden microgel particles.", Lab on a Chip, 2008, 8, 1056-1061.

Seeto, W.J., et al. "Encapsulation of Equine Endothelial Colony Forming Cells in Highly Uniform, Injectable Hydrogel Microspheres for Local Cell Delivery." Tissue Engineering Part C—Methods 2017;23(11):815-825.

Teh, et al., "Droplet microfluidics.", Lab on a Chip, 2008, 8, 198-220.

Tumarkin, et al., "Microfluidic generation of microgels from synthetic and natural polymers". Chemical Society Reviews 38, 2161, 2009.

Velasco, et al., "Microfluidic Encapsulation of Cells in Polymer Microgels", Small 2012;8(11):1633-1642.

Watanabe, et al., "Microfluidic formation of monodisperse tetra-PEG hydrogel microbeads for cell encapsulation," 2016 IEEE 29th International Conference on Micro Electro Mechanical Systems (MEMS), Shanghai, 2016, pp. 718-720.

Zhao, et al., "Injectable Stem Cell-Laden Photocrosslinkable Microspheres Fabricated Using Microfluidics for Rapid Generation of Osteogenic Tissue Constructs." Advanced Functional Materials. 2016:n/a-n/a.

* cited by examiner

Rapid encapsulating of cells in uniform hydrogel microspheres for multiple applications using microfluidic system

- high cell density
- multiple cell types (hMSCs, cancer cells, hiPSCs)
- high viability
- support cellular activities
- even distribution through microsphere

- rapid fabrication
- rapid photocrosslinking
- 10 minutes, 200 μL, 2 million cells

- high batch-to-batch reproducibility
- tight size & shape control
- high batch uniformity
- tailorable size

- cell injection delivery
- drug screening
- stem cell differentiation
- bioreactor tissue production
- cancer tissue model
- long term culture
- cryopreservation
- bioprinting ink

- multiple materials (PF, GelMA, PEGDA)
- low cost
- easy scalable fabrication
- custom-designed t-junction
- larger microspheres >200 μm
- vertical orientation
- readily adjustable assembly (can change inlet and outlet)

FIG 1B

MICROFLUIDICS DEVICE FOR FABRICATION OF LARGE, UNIFORM, INJECTABLE HYDROGEL MICROPARTICLES FOR CELL ENCAPSULATION

RELATED APPLICATIONS

This application claims priority to 62/568,652, filed Oct. 5, 2017, which is hereby incorporated by reference in its entirety.

STATEMENT REGARDING FEDERALLY SPONSORED RESEARCH OR DEVELOPMENT

This invention was made with Government Support under Grant No. NSF-EPS-1158862 and Grant No. NSF-CBET-1150854, both awarded by the National Science Foundation. The Government has certain rights in the invention.

FIELD

The disclosed devices and methods relate to the field of cell therapy, and more specifically to the encapsulation of cells in biomaterials.

BACKGROUND

Hydrogel microspheres are advantageous for use in a wide range of regenerative medicine applications due to their many desirable properties (Lutolf and Hubbell, 2005). These properties have opened up countless potential uses for hydrogels in regenerative medicine including cell delivery (Yao, et al., 2012), 3D drug disease modeling (Horning, et al., 2008), cell differentiation (Shofuda, et al., 2013), drug delivery (Dini, et al., 2003), vaccine production (Tree, et al., 2001), and cell production (Tashiro, et al., 2012). Depending on the application, cells can be either encapsulated within or seeded on the surface of the microspheres, in which case they are referred to as microcarriers.

Microspheres can be fabricated using extrusion, atomization, emulsion, and microfluidics. Among these methods, emulsion and microfluidics are used more widely because of the specialized equipment that is required for the other two methods (Leong and Wang, 2015). Although emulsion allows for scalable production without employing specialized equipment and has been used successfully for mammalian cell encapsulation (Franco, et al., 2011; Pradhan, et al., 2017), this method of microsphere production has some inherent challenges. The emulsion process can require the use of harsh chemical solvents, necessitating further processing steps to minimize the negative impact on cell viability, and can be time consuming depending on the crosslinking method (King and Patrick, 2000; Yang, et al., 2001). Incorporating cells directly is also challenging; the high levels of shear stress make consistent maintenance of high cell viability during the emulsion process difficult. In addition, microspheres produced from emulsion usually have a broad size distribution which can be problematic for downstream applications where tight size distribution is critical (Khademhosseini and Langer, 2007). In contrast, microfluidic approaches can precisely produce uniform microspheres with very narrow size distribution (coefficient of variance, CV<5%) (Headen, et al., 2014). However, one major limitation of microfluidic chip based production is that the resulting microspheres typically have a maximum diameter of around 200 micrometers (Velasco, et al., 2012). This constraint is due to limitations on the channel dimensions imposed by the use of photolithography for microfluidic chip fabrication. Furthermore, pressure differences and changes in flow stability within these smaller channels make it more challenging to encapsulate cells at high densities or in cell clusters, which tend to clog the microfluidic channels and junctions (Headen, et al., 2014). Previous work has shown that high cell density is important in therapeutic cell delivery, where millions of cells were used for large animal cell therapy (Seeto, et al., 2017). The use of high cell densities minimized the delivered volume and fabrication. However, using conventional microfluidic chips, the total number of cells that can be encapsulated per time is low, which fails to meet the need for therapeutic cell delivery. Additionally, there are other restrictions on the applications of microspheres where larger size microspheres are desired, for example, modeling drug testing for large tumor and high throughput cell differentiation. In addition to the limitation on channel size, the complex process of photolithography makes it difficult to adjust the channel dimensions of microfluidic chip efficiently. It requires substantial investment of time and resources to make a microfluidic chip with a different design that can be used for a new application.

SUMMARY

The devices, methods, and compositions disclosed herein accomplish robust cell encapsulation in polymer microparticles using a vertically oriented microfluidic device. Orientation of the device such that the channels extend in non-horizontal directions increases the speed at which microparticles can be produced and greatly improves size and shape uniformity as compared to conventional, horizontally oriented devices. The disclosed devices yield microparticles that are substantially larger than microparticles formed using conventional microfluidic systems, with better control over size and shape. As such, the microparticles can be produced across a wide range of tightly controlled sizes and aspect ratios.

The device is fabricated such that a first inlet channel extends inward from an upper surface of the device housing and downward toward a second inlet channel. The second inlet channel extends inward from a lower surface of the device housing and upward toward the first inlet channel. A hydrophilic polymer precursor solution is flowed into the first inlet channel, and a hydrophobic fluid is flowed into the second inlet channel. The two inlet channels meet at a junction, and an outlet channel extends away from the two inlet channels and toward the other side of the device housing. When the two inwardly flowing streams meet the junction, the polymer precursor solution disperses into the hydrophobic fluid to form dispersed droplets. The dispersed droplets are photopolymerized into microparticles as they travel through the outlet channel. Cells of varying types can be encapsulated with high viability and spatial uniformity within a given microparticle. The cells survive within the microspheres over long periods of time in culture.

Compositions formed using the devices and methods disclosed herein include a therapeutically effective amount of microparticles suspended in a carrier fluid. The microparticles can range in size from 100 micrometers to 1,000 micrometers across a largest dimension. In some embodiments, cells can be encapsulated in the microparticles at a density of up to 60 million per milliliter. The compositions can be used in methods to promote tissue healing or regeneration. The methods could include delivering the composition to a target tissue and retaining the composition at the target tissue for a duration long enough to elicit a therapeutic response. Microparticles without cells can also be used in certain therapeutic methods.

DESCRIPTION OF DRAWINGS

FIG. 1B describes the advantages of various embodiments of the disclosed devices and methods.

(FIG. 6A) Schematic of the microfluidic encapsulation platform. (FIG. 6B) Setup of the microfluidic encapsulation platform in a biosafety cabinet. (FIG. 6C) 3D printing of the jig. The jig helps with consistent, low-cost, and scale-up production of microfluidic devices. (FIG. 6D) The printed reusable jig holds the assembly of the channels together. The T-junction and the channels are molded with Teflon tubes and metal wires, enabling quick testing during prototype development, which is beneficial for understanding the fluid dynamics during microsphere production. (FIG. 6E) PDMS microfluidic device after curing and channel molds being removed. (FIG. 6F) T-junction of the microfluidic device with precursor inlet on top and mineral oil inlet from bottom. The restriction region for stabilization the precursor/oil interface is indicated by an asterisk. (FIG. 6G-6J) Hydrogel microspheres with a wide range of diameters (from 300 μm to 1100 μm) can be produced using the microfluidic encapsulation platform. The hydrogel microspheres are shown in fluorescent green due to the eosin Y used during photocrosslinking.

(FIG. 7E-7F) Compression testing was used to assess elastic moduli of the microspheres. 7G) Elastic moduli of PF, GelMA, and PEGDA were found to be 127.3±24.4 Pa, 1894±257 Pa, and 31,800±5,280 Pa respectively (n=3 separate measurements for each material). Significant difference in elastic moduli was found from all pairs (p<0.05).

(FIG. 8A) Hydrogel precursor to oil flow rate ratio and outlet channel diameter are important factors in determining microsphere diameter. By changing the flow ratio or the outlet channel diameter, the size of microspheres can be adjusted. Significant difference in diameters was found from all pairs (p<0.05, n>78 microspheres/condition). (FIG. 8B) Roundness (above 0.95) was maintained under all conditions. (FIG. 8C-8F) The change of microspheres in size under different experimental conditions shown by fluorescent images.

(FIG. 9A-9C) PF microspheres with encapsulated horse ECFCs from 3 separate batches. (FIG. 9D) Tight control of microsphere size and shape was achieved by the microfluidic encapsulation platform within and between batches (n>54 microspheres per batch). Microsphere average diameter ranged from 740 μm to 793 μm between batches with low variance within each batch. The roundness was above 0.980 with the standard deviation of 0.01 for all batches.

(FIG. 10A) Microsphere diameter, (FIG. 10B) microsphere roundness, (FIG. 10C) elastic modulus with multiple cell types.

(FIG. 11D) Diameters of hiPSCs, horse ECFC, and MCF7 microspheres are 878±29 μm, 957±31 μm, and 939±26 μm (n>20 microspheres for each cell type). Microsphere diameter was found to differ between cell types, possibly as a result of differences of cell size, cell encapsulation density, and dissociation method (p<0.05). High degree of roundness (above 0.95) was maintained for all cell types.

(FIG. 12A) Cell distribution throughout the microsphere post-encapsulation shown by cryosections of ECFC microspheres (Green: Eosin Y, Blue: DAPI). (FIG. 12B) Cells maintained high viability post encapsulation on PF microspheres encapsulated with different cell types (Green: Calcein AM, Red: Ethidium homodimer).

(FIG. 13A-13B) Outgrowth of ECFCs from microspheres indicating high proliferative capability were maintained post encapsulation. (FIG. 13C) The elastic modulus of microspheres with horse ECFCs have significantly increased from 142±10 Pa on day 1 to 354±62 Pa on day 3 (p<0.05, n>4 microspheres/condition). (FIG. 13D-13E) ECFCs remodeled the microsphere size and shape during culture. (FIG. 13F-13G) Encapsulated ECFCs maintained proliferative shown by the expression of cell proliferation marker Ki67 (Blue:DAPI, Magenta:Ki67).

(FIG. 15A-15C) Colonies outgrowth of cancer cells on MCF7 microspheres, indicating proliferation of cells for a long-term culture. (FIG. 15E-15G) SEM images of MCF7 microspheres with magnification of 1,000×. Cancer cell colonies are indicated by arrows. (FIG. 15D, FIG. 15H) Encapsulated MDA-MB-231 cells maintained high viability for a long-term. Viability assay was conducted on day 38 post-encapsulation (Green: Calcein AM, Red: Ethidium homodimer).

FIG. 16A) Schematic of ECFC encapsulation in PF microspheres. (FIG. 16B) Timeline for in vitro, ex vivo and in vivo FIGS. 17A-17I. High microsphere uniformity and cell viability post-encapsulation.

(FIG. 18A) By Day 1, cells are aligning and covering the surface of the microsphere (MS). (FIG. 18B) Outgrowth ECFCs from the MS forming a confluent monolayer on Day 3. (FIG. 18C) Outgrowth ECFCs proliferating 1 day after transfer of MS to a new well plate. (FIG. 18D) ECFCs sub-cultured from the confluent monolayer of outgrowth ECFCs maintain characteristic high proliferation rate.

FIG. 19I) No difference was found in expression of markers (vWF, CD105, and CD14) or Dil-Ac-LDL uptake between the outgrowth ECFCs from microspheres and non-encapsulated ECFCs (flow cytometry, n=3 separate encapsulations).

(FIG. 20A) XTT assay indicated the encapsulated ECFCs (Day 1) remained viable after shearing through different sizes of needles (n=4 separate encapsulations normalized to control). There is no statistical difference between conditions. (FIG. 20B) PEGDA microspheres (stained with trypan blue) remained localized in the tissues after subcutaneous injection at the edge of a wound in a cadaver limb from a horse. (FIG. 20C) Overlay image of the autofluorescence of ECFC encapsulated PF microspheres (green) in a horse subcutaneous tissue 1 day after ex vivo culture. (FIG. 20D) Phase contrast image showing tubule formation (black arrow) of the encapsulated ECFCs on the surface of the microspheres in subcutaneous tissue 1 day after ex vivo culture.

(FIG. 21A) Fluorescent microscopy showed the presence of Q-tracker labeled ECFCs (fluorescent red in color) encapsulated in microspheres before injection. (FIG. 21B) Encapsulated ECFCs (red) were found in cryosectioned biopsy 1 week after injection. Migration of ECFCs to host tissue was observed (white arrows).

(FIG. 22A) HiPSCs suspended in hydrogel aqueous-precursor solution were infused through a custom PDMS mold opposite an oil phase to produce uniform cell-laden microspheres. The cell-polymer solution was pumped through the tubing at 1 ml/hr and each microsphere was photocrosslinked for approximately 1 s. (FIG. 22B) Encapsulated hiPSCs survive encapsulation as visualized using a Live/Dead Assay with live cells shown in green and dead cells in red. (FIG. 22C) Microspheres could be readily visualized through long exposure from the autofluorescence of eosin Y 24 h after photocrosslinking and images were used to quantify microsphere diameter and circularity. (FIG. 22D) The microspheres were uniform both within a batch and between batches as shown in the violin plots. Each color represents an individual batch while each microsphere is represented by a black dot. Microspheres were 908±40 μm in diameter and (FIG. 22E) were highly circular (0.96±0.02, n=8 individual batches, 485 spheres analyzed). (FIG. 22F) Successful cell encapsulation and maintenance of microspheres in suspension culture could be visualized from daily phase contrast images prior to cardiac differentiation initiation. (FIG. 22G) Cryosections from day 0 show uniform distribution of cells throughout the hydrogel from nuclei staining of various size sections.

(FIG. 23A) Phase contrast images throughout the time course of cardiac differentiation showed the progression of differentiating cells in PEG-fibrinogen microspheres. (FIG. 23B) Prior to cardiac differentiation, cell proliferation for two hiPSC lines was verified by XTT assay, which showed an increase in optical density between day −2 and day −1 (n=5 microspheres per condition), indicating continued proliferation and growth of the cells. (FIG. 23C) Ki67 staining (green) confirms the cells maintain their proliferative phenotype following cell encapsulation. (FIG. 23D) From the onset of cardiac differentiation (day 0), microsphere size increased significantly by day 3, and continued to grow until day 7. (FIG. 23E) HiPSC phenotype of rounded colonies could be seen using Phalloidin staining prior to initiating cardiac differentiation (day 0). (FIG. 23F) By day 10, the cells start to elongate, indicative of cardiomyocyte phenotype, visualized using Phalloidin staining. (FIG. 23G) The PEG-fibrinogen provides a soft microenvironment (<200 Pa) throughout cardiac differentiation, similar to that of a developing heart.

(FIG. 24A) Day 20 microspheres were composed of 71.6±8.4% CMs (cTnT+), with 7.1±1.7% proliferating CMs (cTnT+/Ki67+). Microspheres were also contained of 8.41±6.5% fibroblasts (P4HB+, n=3 individual batches). (FIG. 24B-24F) The resulting cardiac microspheres exhibited appropriate temporal changes in gene expression, including a decrease in pluripotent gene, Oct4, as well as appropriate changes in cardiac genes MLC2v, αMHC, and βMHC, and the expression of functional protein Cx43. (n=3 biological replicates in duplicate, 1-way ANOVA p=0.05). (FIG. 24G) Staining of an individual microsphere with cardiac marker (cTnT) shows differentiation throughout the spheroid. (FIGS. 24H-24I) From day 21 to day 50, sections labeled with αSA show the sarcomeres becoming more aligned, a feature of maturing CMs. (FIG. 24J) The cells exhibit cell-cell interactions as shown by the labeling of Cx43 in day 250 sections.

(FIG. 25A) Cells remodeled their PEG-fibrinogen microenvironment to form dense cardiac microspheres. (FIG. 25B) Aligned cells were visualized on the surface with ECM deposition. (FIG. 25C) Higher magnification SEM image showed junctions between two adjoining cells. (FIG. 25D) Aligned myofibril structure was detected in day 60 microspheres, similar to (FIG. 25E) human cardiac tissue samples. (FIG. 25F) Representative microsphere CMs image display positive sarcomere staining with the cardiac marker αSA (red). Samples were counterstained with DAPI (blue). (FIGS. 25G-25I) Cardiac microspheres were sectioned using a cryostat and immunofluorescently labeled with cardiac marker, αSA (red), and DAPI (blue). The section shown here shows positive staining for αSA indicating cardiac differentiation occurred throughout the entire microsphere.

(FIG. 26A) Microspheres were dissociated and plated onto the MEA. (FIG. 26B) Day 20 CMs responded to the β-adrenergic agonist, isoproterenol (Iso), increasing the contraction rate. The subsequent addition of propranolol (Prop), a β-adrenergic antagonist, reversed the initial increase in contraction rate caused by isoproterenol. (FIG. 26C) In addition to appropriate response to drug treatment, day 50 microsphere CMs showed 1:1 capture to outside pacing frequencies up to 6.0 Hz. (FIG. 26D) The contraction rate of the cardiac spheroids is 16.6±5.9, 13.8±2.3, and 25.6±10.8 beats per minute on days 20, 30, and 60 respectively. (FIG. 26E) The cardiac spheroids had a calcium transient duration (CTD) at 50% repolarization of 1256 ms and 1713 ms at 80% repolarization. (FIG. 26F) The contraction and relaxation velocities were determined using a MATLAB GUI in which the contraction rate of the cardiac spheroids was 110±49, 161±69, and 175±112 μm/s on days 20, 30, and 60 with relaxation velocities of 70±36, 106±42, and 146±88 μm/s, respectively in which a representative trace is shown in (FIG. 26G).

(FIG. 27A) Schematic of the microfluidic setup for the generation of cell-laden PF microspheres and 3D culture. (FIG. 27B) Phase contrast image of MCF7 cell-encapsulated microspheres. (FIG. 27C) MCF7 microspheres imaged under green fluorescence (due to presence of Eosin Y photoinitiator in hydrogel precursor). Scale bar=1,000 μm. (FIG. 27D) Distribution of microsphere diameter from three independent batches demonstrates high degree of inter-batch and intra-batch uniformity and monodispersity.

(FIGS. 28A-28C) Confocal z-projections of MCF7 cells and (FIGS. 28D-28F) those of MDA-MB-231 cells over 2 weeks in culture. White dotted circles denote edge of microspheres. (Green: Calcein AM, live cells; red: ethidium homodimer, dead cells) (Scale bar=200 μm). (FIG. 28G) High magnification z-projections of MCF7 cells and (FIG. 28H) MDA-MB-231 reveal overall high viability and differences in cell-type dependent morphology (Scale bar=100 μm). (FIG. 28I) Quantification of cell viability within PF microspheres reveals high viability for both cell types through 14 days in culture.

FIGS. 29A-29N. Variation in microsphere size and stiffness over time. (FIGS. 29A-29L) Phase contrast images of breast cancer cells encapsulated within PF microspheres demonstrates variations in size distribution and cellular appearance of MCF7 and MDA-MB-231 cells. (FIG. 29A, FIG. 29C, FIG. 29E, FIG. 29G, FIG. 29I, FIG. 29K: Scale bar=1,000 μm; FIG. 29B, FIG. 29D, FIG. 29F, FIG. 29H, FIG. 29J, FIG. 29L: Scale bar=200 μm). (FIG. 29M) Quantification of microsphere diameter reveals significant reduction in size for both cell types over 14 days in culture (*p<0.05, n=minimum of 50 microspheres). Red circles denote individual microspheres, blue diamonds denote mean while rectangular boxes represent lower quartiles, medians and upper quartiles of respective groups. (FIG. 29N) Quantification of Young's modulus reveals significant increase in MCF7 microsphere stiffness but no variation in MDA-MB-231 microsphere stiffness over time. Acellular microsphere stiffness is significantly low compared to cell-laden microsphere for both cell types. *, #p<0.05, n=3 microspheres per group).

(FIG. 31A) SEM image of MCF7 microspheres reveals dense local colony formation in individual microspheres. (FIG. 31B) At higher magnification, MCF7 cells appear to be tightly packed within individual colonies with visible cell surface microvilli-like features. (FIG. 31C) SEM image of MDA-MB-231 microspheres and (FIG. 31D) higher magnification image reveals individual cells (bulge-like appearance) interacting with the surrounding PF hydrogel matrix. (FIG. 31E) Ki67 immunofluorescent staining of MCF7 microspheres. (FIG. 31F) F-actin, Ki67 and DAPI staining of MCF7 microspheres. (FIG. 31G) Ki67 immunofluorescent staining of MDA-MB-231 microspheres. (FIG. 31H) F-actin, Ki67 and DAPI staining of MDA-MB-231 microspheres.

FIG. 32A shows fluorescent images of microparticles resulting from an oil flow rate of 2 mL/hour with a corresponding PEGDA flow rate of 2 mL per hour. FIGS. 32B and 32C show microparticles resulting from an oil flow rate of 2 mL/hour with a corresponding PEGDA flow rate of 6 mL/hour and 9 mL/hour, respectively. As shown in FIGS. 32D and 32E, increasing the polymer precursor flow rate while keeping the oil flow rate constant increases the length and the aspect ratio of the resulting microparticles.

(FIG. 33A) Phase contrast image of fibroblasts loaded in elongated microparticles. (FIG. 33B) F-actin staining of fibroblasts loaded in elongated microparticles. (FIG. 33C) Image of calcien fluorescent staining of fibroblasts encapsulated in elongated microparticles (indicating live cells). (FIG. 33D) Image of ethidium bromide staining of fibroblasts encapsulated in elongated microparticles (indicating dead cells). Calcien (live) staining of hiPSCs in elongated microparticles having higher (FIG. 33E) and lower (FIG. 33F) aspect ratios.

(FIG. 34A) There is no statistical difference in the beat rate of the cardiomyocytes cultured in microparticles having aspect ratios of 1-2, 2-3, or greater than 3. However, maximum contraction velocity (FIG. 34B) and maximum relaxation velocity (FIG. 34C) increase with increasing aspect ratio. * signifies p<0.05, n≥2.

FIGS. 35A-35I show microparticles of varying aspect ratios and uniformity. FIG. 35J is a table showing how flow fraction affects aspect ratio.

FIG. 35K is a graph showing how flow fraction affects aspect ratio of the microparticles.

DETAILED DESCRIPTION

Figure 1A:
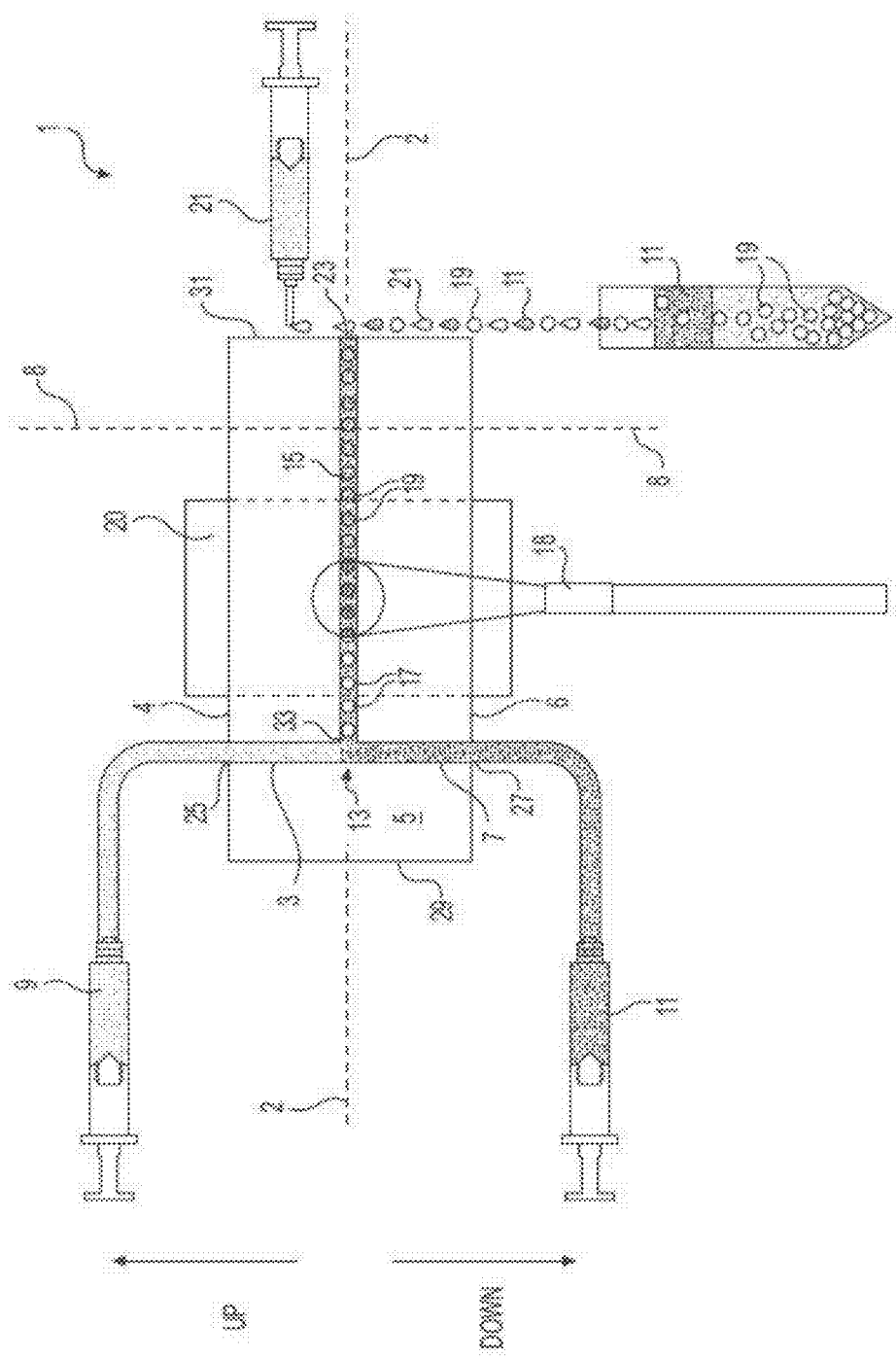
FIG. 1A is a schematic of the method for encapsulating cells in microparticles.

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another example includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

The term "therapeutically effective amount" refers to the amount of cell-laden microparticles that will elicit the biological or medical response of a tissue, system, animal, or human that is being sought by the researcher, veterinarian, medical doctor or other clinician over a generalized period of time. In some embodiments, a desired response can be wound healing. In some embodiments, a desired response can be vascularization of a tissue, or transplantation of viable cells. In some instances, a desired biological or medical response is achieved following administration of multiple dosages of the composition to the subject over a period of days, weeks, or years.

The devices, methods, and compositions disclosed herein accomplish robust cell encapsulation in polymer microparticles using a vertically oriented microfluidic device 1, a schematic of which is shown in FIG. 1A. For directional purposes, FIG. 1A includes imaginary horizontal plane 2 and vertical plane 8 extending through the device housing 5, as well as arrows indicating the upward and downward directions. A first inlet channel 3 extends inward from an inlet port 25, which is on or attached to the upper surface 4 of the device housing 5, and adjacent to a first side surface 29 of the device housing 5. The first inlet channel 3 continues downward into device housing 5 and toward a second inlet channel 7. The second inlet channel 7 extends inward from a second inlet port 27, which is on or attached to the lower surface 6 of the device housing 5 and adjacent to the first side surface 29 of the device housing 5. The second inlet channel 7 continues upward into the device housing 5 and toward the first inlet channel 3. A hydrophilic polymer precursor solution 9 is flowed into the first inlet channel 3, and a hydrophobic fluid 11 is flowed into the second inlet channel 7. The two inlet channels 3, 7 meet at a junction 13, and an outlet channel 15 extends away from the two inlet channels 3, 7 and toward an outlet port 23 on the second side surface 31 of the device housing 5. When the two inwardly flowing streams meet at the junction 13, the polymer precursor solution 9 disperses into the hydrophobic fluid 11 to form dispersed droplets 17. The dispersed droplets 17 are photopolymerized by light 18 shining through a front side of the housing 5 and through the outlet channel 15. In some embodiments, the light is reflected off mirror 20 that is attached to the back side of the device housing 5, such that it travels back through the outlet channel 15. The droplets 17 are thus polymerized into microparticles 19 as they travel through the outlet channel 15. Certain embodiments may also include a wash fluid 21 that is flowed over the outlet port 23 to stabilize flow within microfluidic channels 3, 7, 15. The resulting microparticles 19 are highly uniform in both size and shape, and are larger than microparticles formed using conventional microfluidic systems. Cells of varying types can be encapsulated with high viability and spatial uniformity within a given microparticle by first mixing the cells with the polymer precursor solution. The encapsulated cells survive within the microspheres over long periods of time in culture. FIG. 1B is a diagram outlining the applications and advantages of the various embodiments of the disclosed devices, methods and compositions.

Figure 2:
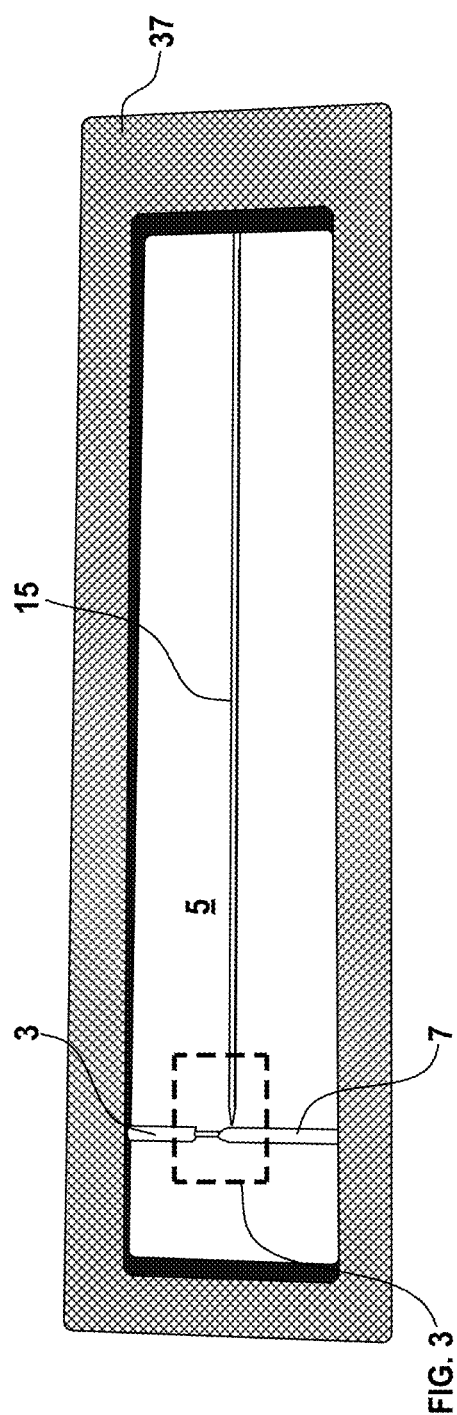
FIG. 2 shows a microfluidic device still held within the molding bracket used during fabrication.
Figure 3A:
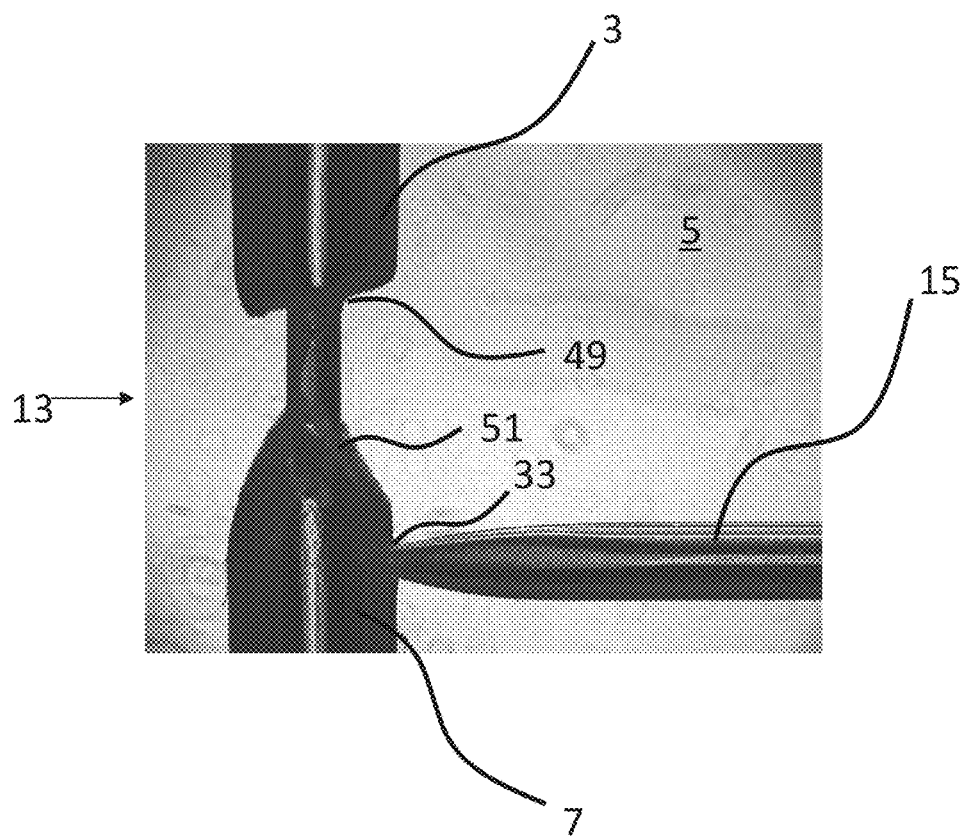
FIG. 3A is a magnified image of the boxed region outlined in FIG. 2. It shows the junction of the inlet channels and the outlet channel extending away from the inlet channels.

FIG. 2 shows an image of an embodiment of the device housing 5 incorporating first inlet channel 3, second inlet channel 7, and outlet channel 15. FIG. 3A shows a magnified image of the boxed area of FIG. 2, zooming in on the junction 13 of the inlet channels 3, 7 and the exiting outlet channel 15. In the embodiment shown, the first inlet channel 3 and second inlet channel 7 both extend parallel to the vertical plane 8 that extends through the device housing 5, at a 90 degree angle to horizontal plane 2. The inlet channels 3, 7 meet each other to form a continuous straight line that extends vertically through the device housing 5.

The outlet channel 15 extends outwardly from the top portion of the second inlet channel 7, just below junction 13, parallel to the horizontal plane 2 and at a 90 degree angle to the vertical plane 8. Conventionally, T-junctions are designed such that the two inlet streams are perpendicular to each other, i.e. with the dispersed phase (the precursor solution with cells) entering the continuous phase (the hydrophobic fluid) at a 90 degree angle. The outlet channel is conventionally a continuation of the continuous phase channel. In the embodiment shown in FIGS. 2 and 3A, the precursor solution and the hydrophobic fluid meet at the T-junction and then progress down the outlet channel which is perpendicular to both inlet channels. This modification of the T-junction design allows for control of the size and shape of microparticles using inlet flow ratio based control. Inlet flow ratio based control means that varying the ratio of the flow rates of the precursor solution to the hydrophobic fluid can alter the size and shape of the microspheres. For example, initially, the hydrophobic fluid phase has a much higher flow rate than precursor solution. When increasing the ratio of precursor to hydrophobic fluid flow rate, the hydrophobic fluid phase flows relatively slower and the precursor solution flows relatively faster, resulting in a decrease in shear stress. Without being wed to theory, a possible explanation for inlet flow ratio based control is that this decreased shear stress makes it harder to break the surface tension of the precursor solution, resulting in an increase in microsphere size until it is limited by the size of the outlet channel.

Inlet flow ratio based control is explained in more detail below, referring to FIG. 3A. As shown in FIG. 3A, the top part is the precursor inlet (first inlet flow channel 3). Below the inlet is a restriction segment working as a flow stabilizer (stepwise narrowing diameter of first inlet flow channel 3). The restriction segment is implemented to stabilize the interface of the precursor solution 9 and the hydrophobic fluid 11 prior to the fluids entering the outlet channel 15 as the denser precursor solution 9 otherwise tends to escape from the flow and form unwanted droplets that sink to the bottom inlet (second inlet channel 7). Beneath the flow stabilizer is a conical region (tapered narrowing diameter of second inlet channel 7) instead of a cylindrical region. The taper is introduced to eliminate the dead volume of precursor solution 9. The tapered end is designed to increase the flow velocity at the junction between the second inlet channel 7 and the outlet channel 15 (connection point 33), to aid in microparticle formation.

Without being wed to theory, the equations and explanation below may help to describe how microparticle size and geometry can be controlled. They are:

Capillary number:

$$Ca = \frac{\text{Viscous force}}{\text{Surface tension}} = \frac{\mu V}{\gamma} \quad \text{Equation 1.}$$

Where:
$\mu$: Dynamic viscosity of continuous phase (oil phase)
$V$: Relative velocity of continuous phase (hydrophobic fluid phase) to discrete phase (aqueous precursor solution)
$\gamma$: Interfacial tension (precursor solution/hydrophobic fluid)

Flow Fraction:

$$\text{Flow Fraction} = \frac{\text{Precursor flow rate}}{\text{Precursor flow rate} + \text{Oil flow rate}} = \frac{V_{Gel}}{V_{Gel} + V_{Oil}} \quad \text{Equation 2.}$$

Narrowing Ratio ($NR$):

$$\text{Narrowing Ratio}(NR) = \frac{\text{Diameter}_{Junction}}{\text{Diameter}_{Outlet}} \quad \text{Equation 3.}$$

where:
junction refers to connection point 13
outlet refers to widest diameter of outlet channel 15

Microsphere diameter $$\text{Diameter}_{Microsphere} \propto \frac{1}{Ca} \quad \text{Equation 4.}$$

Figure 3B:
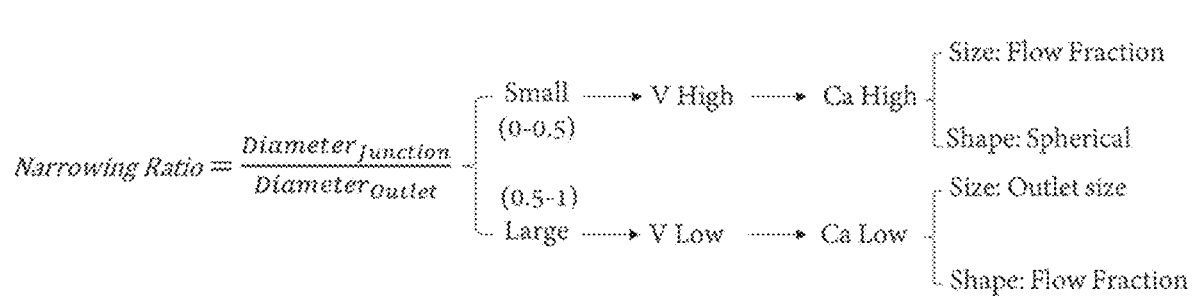
FIG. 3B is a tree chart describing the relationship between narrowing ratio and the microparticle size and shape.

In modulating the microsphere size and geometry, capillary number (Equation 1) plays an important role. Capillary number (Ca) describes the relative effect of viscous forces and surface tension at the interface of two immiscible fluids. The relationship between the diameter of the microspheres and capillary number is described by Equation 4. When Ca has a higher value, the diameter of the microparticles decreases. When Ca has a lower value, the diameter of the microparticles increases until it is restricted by the diameter of the outlet channel 15. Based on the definition of capillary number (Ca=$\mu V/\gamma$), when V (relative velocity of continuous phase to discrete phase) increases, Ca has a higher value. When V decreases, Ca has a lower value. Based on the definition of V, it is directly related to the Flow Fraction (Equation 2), which defines the relative flow rate of precursor solution 9 to hydrophobic fluid 11. And flow rate is a parameter that can be controlled during experiments. For a more consistent photocrosslinking, the microparticles going through the outlet channel 15 have a similar exposure time to the visible light source 18, which means they have a similar velocity (velocity=flow rate/cross section area; cross section area $\propto$ diameter of outlet channel$^2$) in the outlet channel 15. The total flow rate will change along with the widest diameter of the outlet channel 15 in order to achieve a similar velocity in the outlet channel 15. As a result, the V is not always determined by the absolute diameter of the junction between the second inlet channel 7 and the outlet channel 15 (connection point 33). For example, compared to a system where the diameter of the junction between second inlet channel 7 and outlet channel 15 (connection point 33)

is the same as the widest diameter of outlet channel 15, the V has a much higher value in a system where the diameter of the junction between second inlet channel 7 and the outlet channel 15 (connection point 33) is much smaller than the full diameter of outlet channel 15. To better quantify the V in Ca, Narrowing Ratio (Equation 3) is introduced to describe the relative value of Junction Diameter (junction of outlet channel 15 and second inlet channel 7, also referred to as connection point 33) and Outlet Diameter (full diameter of outlet channel 15. To summarize the description above, a tree chart is shown as FIG. 3B. When the Narrowing Ratio is small, V has a high value, which means Ca has a high value. The size of the microparticles is determined by the Flow Fraction and the shape of the microparticle is spherical. When the Narrowing Ratio is large, V has a low value, which means Ca has a low value. The size of the microparticle is limited by the diameter of the outlet channel and the shape of the microparticle is determined by the Flow Fraction.

By increasing the Flow Fraction, the aspect ratio (rod length:rod diameter) can be increased. The Reynolds number (Re), which describes the relative effect of inertial forces and viscous forces, comes into play when varying the aspect ratio of the microparticles. When the diameter across connection point 33 is large, the Narrowing Ratio is relatively large, the instantaneous velocity is low, and the Ca and Re numbers will be low. Viscous forces therefore cannot overcome the surface tension of the polymer precursor solution as readily. In this case radial diameter of the microspheres is mainly dependent on the radial diameter of the outlet channel 15. By changing the ratio of the inlet flow rates (polymer precursor solution:hydrophobic fluid/oil), the shape or the aspect ratio of the microspheres can be modulated. That is, for large connection points 13, with low Ca and Re numbers where the radial diameter is strongly dependent on the radial diameter of the outlet channel, the aspect ratio of the microparticles can be adjusted by controlling the flow fraction, which is the relative magnitude of the two inlet flow rates.

When the diameter across connection point 13 is decreased, the Narrowing Ratio is relatively small, and the instantaneous velocity increases accordingly, which results in higher value of Ca and Re numbers. The increase in Ca means that viscous forces are able to break the surface tension more readily, leading to a decrease in microsphere size. Moreover, the contraction at the junction likely introduces more velocity components perpendicular to the axis of the outlet channel, which also work to break the hydrogel precursor solution. If the diameter across connection point 13 size is too small, the corresponding Re number will increase drastically, which means the fluid will behave more like turbulent flow. As a result of the instability, the microspheres will be small and nonuniform in size.

While the configuration of the microfluidic channels shown in FIGS. 2 and 3A offers the aforementioned advantages, various other configurations are also envisioned and are within the scope of this disclosure. For example, the inlet channels 3, 7 need not be perpendicular to the horizontal plane 2, nor parallel to the vertical plane 8. The first inlet channel 3 can extend downward into the housing 5 at an angle to the horizontal plane 2 that is less than 90 degrees, and the second inlet channel 7 can extend upward into the housing 5 at an angle to the horizontal plane 2 that is less than 90 degrees. Likewise, the outlet channel 15 can extend away from the first and second inlet channels 3, 7 at an angle that is not parallel to the horizontal plane 2.

Figure 16:
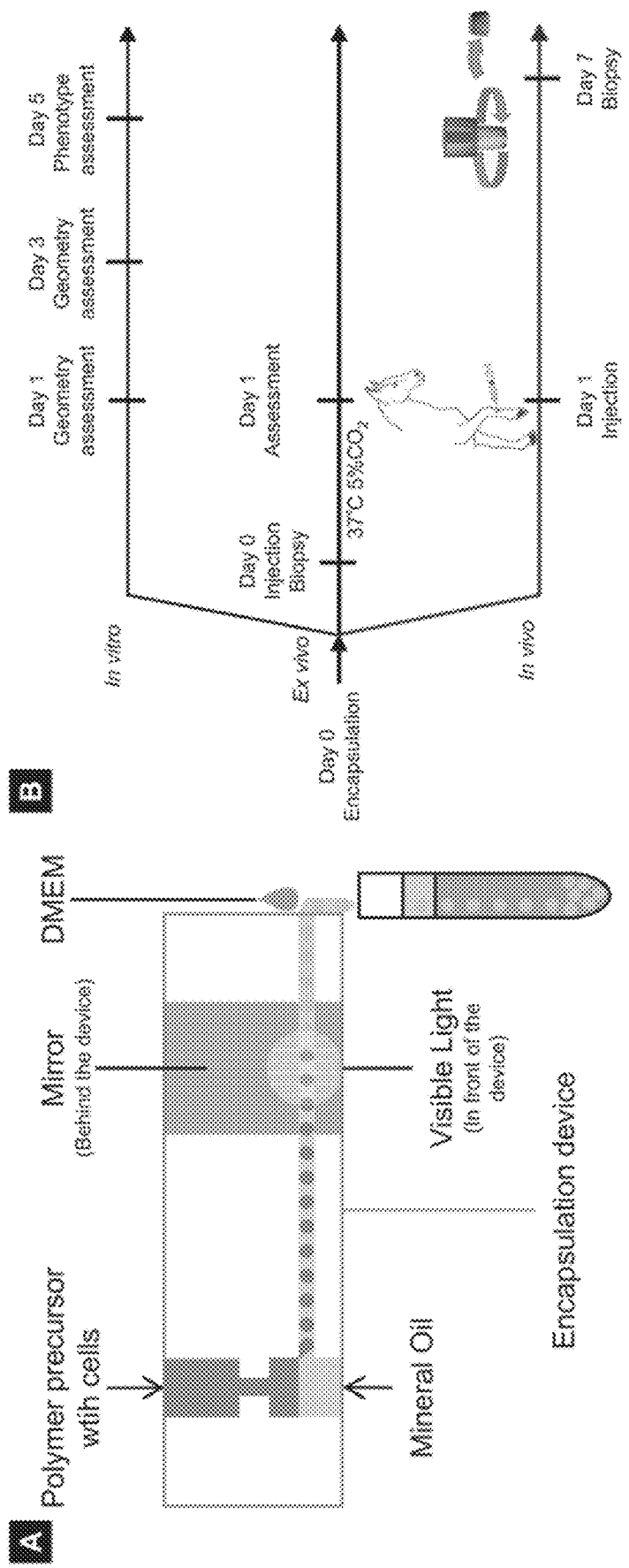
FIGS. 16A-16B.

In the embodiment shown in FIGS. 2 and 3A, the inlet channels 3, 7, and the outlet channel 15 are cylindrical along portions of their lengths. In the embodiment shown in FIGS. 2 and 3, each of the inlet channels 3, 7 narrow in diameter as they approach junction 13. In some embodiments, the widest diameter of the first and second inlet channels is from about 0.5 millimeters to 2.5 millimeters (including, for example, about 0.5 millimeters, about 0.75 millimeters, about 1 millimeter, about 1.25 millimeters, about 1.5 millimeters, about 1.75 millimeters, about 2 millimeters, about 2.25 millimeters and about 2.5 millimeters). The first inlet channel 3 narrows in a stepwise fashion at a stepwise transition 49, whereas the second inlet channel 7 narrows in a tapered fashion at tapered transition 51. The narrowed diameter of the first inlet channel 3 can range from, for example, about 0.2 to about 0.8 millimeters, including, for example, about 0.2 millimeters, about 0.3 millimeters, about 0.4 millimeters, about 0.5 millimeters, about 0.6 millimeters, about 0.7 millimeters and about 0.8 millimeters. However, in other embodiments, the diameters of the inlet channel may both narrow in a tapered fashion, may both narrow in a stepwise fashion (as shown in FIG. 16A and described in the Examples, below), or the second inlet channel 7 may narrow in a stepwise fashion while the first inlet channel 3 may narrow in a tapered fashion (the reverse of the embodiment of FIGS. 2 and 3A).

In the embodiment shown in FIGS. 2 and 3A, outlet channel 15 attaches to the top portion of second inlet channel 7 at connection point 33. This configuration is advantageous because it leverages emulsification to stabilize the formation of the microspheres before they enter the outlet channel 15. The hydrophobic fluid coming from the bottom provides an advantage in terms of buoyancy (wants to rise, so it will move higher to support the aqueous polymer precursor as it they move through the connection point 13). However, in other embodiments, the outlet channel 15 can attach to and extend away from the junction 13 between the inlet channels 3, 7, or the outlet channel 15 can attach to and extend away from a lower portion of the first inlet channel 3. The outlet channel 15 can extend away from a portion of the inlet channel 3 or 7 having the widest diameter, or it can extend away from the portion of the inlet channel 3 or 7 having a narrowed diameter (a portion adjacent the junction 13).

In the embodiment shown in FIGS. 2 and 3A, the width of the outlet channel 15 increases as it extends away from inlet channels 3, 7. The ratio of the narrowest diameter of the outlet channel 15 to the widest diameter of the outlet channel 15 can range from about 0.2 to about 1.1 millimeters, including about 0.2, 0.3, 0.4, 0.5, 0.6, 0.7, 0.8, 0.9, 1.0 and 1.1 millimeters. The outlet channel can have a very large diameter as compared to conventional microfluidic devices. For example, the largest width of the outlet channel 15 can range from about 0.2 millimeters to about 3 millimeters, including about 0.2 millimeters, about 0.4 millimeters, about 0.6 millimeters, about 0.8 millimeters, about 1.0 millimeters, about 1.2 millimeters, about 1.4 millimeters, about 1.6 millimeters, about 1.8 millimeters, about 2.0 millimeters, about 2.2 millimeters, about 2.4 millimeters, about 2.6 millimeters, about 2.8 millimeters, and about 3.0 millimeters. The length of the outlet channel 15, as measured from its connection point 33 to the inlet channel 7 to the outlet port 23 on the side surface 31 of the housing 5, can be from about 5 centimeters to about 20 centimeters, including about 5, 6, 7, 8, 9, 10, 11, 12, 13, 14, 15, 16, 17, 18, 19, and about 20 centimeters in length.

Figure 4:
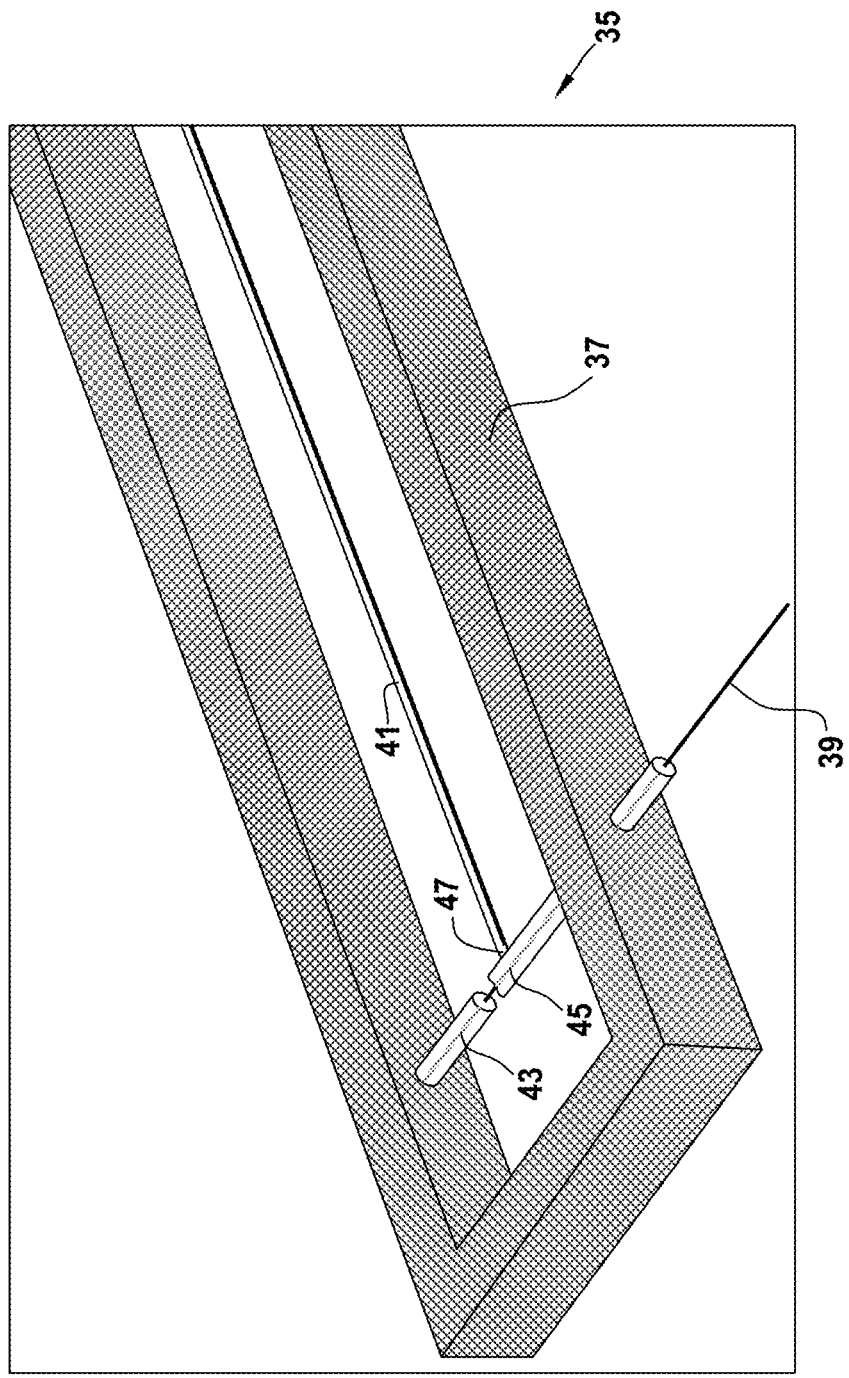
FIG. 4 shows the molding bracket with channel molds in place, prior to the pouring of the elastomer that forms the disclosed microfluidic device.
Figure 5A:
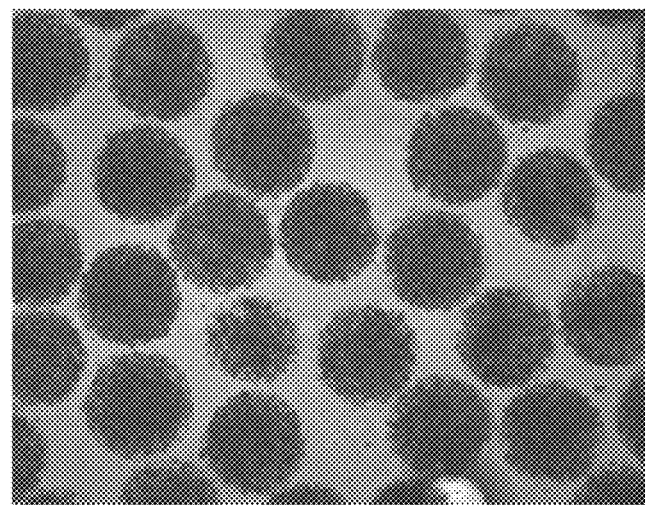
FIG. 5A is a phase contrast image highlighting the high degree of uniformity of cell-laden microparticles (in both size and roundness).
Figure 5B:
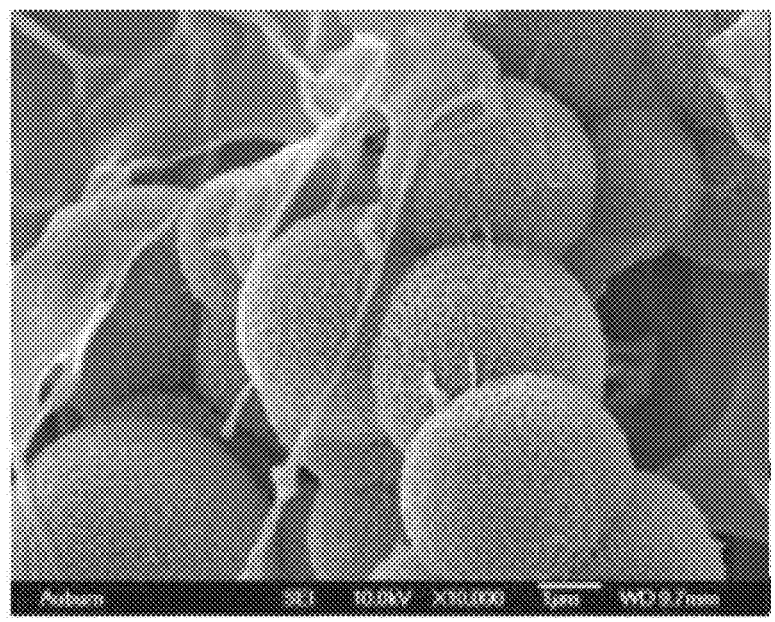
FIG. 5B is an SEM image highlighting the high degree of uniformity of cell-laden microparticles (in both size and roundness).

Housing 5 can be fabricated from any transparent material that enables transmission of light into the outer channel 15 for photopolymerization. For example, housing 5 can be formed of polydimethylsiloxane. Hydrophobic materials, such as PDMS, are advantageous because the aqueous phase is not drawn to the surfaces of the device as it moves through the channels. In one embodiment, the housing 5 is fabricated using a molding process. An example mold 35 for the housing 5 is shown in FIG. 4. The mold 35 includes an outer bracket 37, a first wire 39, a second wire 41, a first inlet channel mold 43 (formed in this embodiment by tubing that fits around wire 39), and a second channel mold 45 (also formed in this embodiment by tubing that fits around wire 39). In some embodiments, bracket 37 can be pre-fabricated, for example, using high throughput methods such as 3D printing.

Wires and tubing can be used in combination to form the molds that ultimately create channels 3, 7, and 15. In the embodiment shown in FIG. 4, the first wire 39 extends vertically through the bracket 35 and supports the tubing of channel molds 43, 45, which can be slid over the first wire 39 during the fabrication of the mold. The shapes and diameters of the wires and tubing can be altered for achieve channels of desirable shapes and diameter. For example, in this embodiment, the tubing of first channel mold 43 has been cut bluntly to form the stepwise transition 49 of first inlet channel 3 that is shown in FIG. 3A. The first inlet channel 3 is ultimately molded around the combination of the first wire 39 and the first inlet channel mold 43. The tubing of second channel mold 45 has been whittled to form the tapered transition 51 of second inlet channel 7 that is shown in FIG. 3A. The second inlet channel 7 is ultimately molded around the combination of the first wire 39 and the second inlet channel mold 45. However, the shapes of the tubing and wires can vary to achieve channels of desired shapes. The diameters of the first and second inlet channels 3, 7 can be widened or narrowed by, for example, using wires and/or tubing of the desired size.

The second wire 41 extends horizontally through the bracket 37, having a first end 47 that is attached to channel mold 45. In this embodiment, the first end 47 of the second wire 41 has been sharpened to a taper and can be used to pierce the polymer tubing 45 for fixation during the molding process. The resulting outlet channel 15 has a diameter that widens as it extends away from second inlet channel 7, as shown in FIG. 3A. Alternatively, the first end 47 of the second wire 41 can be attached to or second inlet channel mold 45 by another fixation method such as, but not limited to, adhesives or heat bonding/melting. In other embodiments, the second wire 41 can be attached to first wire 39 by any of the aforementioned fixation mechanisms, for example, between the tubing of channel molds 43, 45, so as to create an outlet channel 15 that extends away from junction 13. Or, alternatively, the first end 47 of the second wire 41 can be attached to the first inlet channel mold 43 by any of the aforementioned fixation mechanisms. The second end of the second wire 41 that forms outlet channel 15 (not shown) is attached to the far side of the bracket (the full bracket 37 can be seen in FIG. 2). Though not shown, the diameter of outlet channel 15 can be altered by using a narrower second wire 41 or by positioning any size of tubing over second wire 41.

After the wires and tubing are arranged within bracket 37 to achieve the desired channel configuration, a backing can be affixed to the bracket 37. In some embodiments, affixing the backing to bracket 37 can be as simple as securing an elongated piece of glass (a slide, or coverslip, for example) to the bracket 37 using binder clips. Alternatively, the backing can be any other material and can be affixed to the bracket 37 using bonding, pegs, screws, or any other fixation method known in the arts. The material used to form housing 5 can then be positioned around the mold 35. In some embodiments, this may include pouring the housing material in an uncured state into the bracket 37 and around the wires and tubing. For example, housing 5 can be formed of a silicone elastomer, such as polydimethysiloxane, by using a Sylgard 184 silicone elastomer kit (Dow Corning). In this embodiment, the base and curing components are mixed then poured into the pre-assembled bracket and then the PDMS is cured to form housing 5. Once the PDMS is cured, the wires, tubing are removed and the resulting housing 5 is extracted from the bracket 37. The housing 5 can then be cleaned and sterilized, for example, by washing, sonicating, soaking in 70% ethanol, UV sterilization, ethylene oxide treatment, or any combination of the above, before and after each use.

The fabrication of housing 5 using molding processes has certain advantages over photolithographic processes that are conventionally used for fabricating microparticles. Wires and tubing can be rapidly changed to easily test many combinations of channel sizes and junctions. Behavior at a channel junction is challenging to analyze and predict, and it is therefore helpful to produce empirical data without having to redesign and produce new photolithography chips (a process that is both time consuming and expensive). There are also currently size limitations on the diameters of channels that can be made using photolithographic techniques, because typical photoresist only permits the formation of stable and consistent structures with maximum heights of around 200 micrometers. These size limitations prevent wider channels such as those used to produce the microparticles of submillimeter size disclosed herein. The shorter length of conventional photolithography chips is also a limitation, due to the lower amount of space provided for photocrosslinking the droplets 17. The space between the light source and the connection point 13 must be large enough that light cannot travel back up the channel to the connection point 13 to crosslink the polymer there (or one would have to drop the intensity of the light, reducing speed). Using the fabrication techniques described herein, the bracket 37 can be as long as desired, which ensures that droplets 17 of polymer precursor solution 9 spend ample residence time in the outlet channel 15 for sufficient polymerization. Another limitation of photolithography is that it is difficult to impossible to form channels that are circular in cross section.

The following description refers back to FIG. 1A. As described briefly above, the method of making the microparticles 19 involves flowing the hydrophilic polymer precursor solution 9 downward through first inlet channel 3, which is positioned at an angle to the horizontal plane 2. A hydrophobic fluid 11 is flowed upward through second inlet channel 7, which is positioned below the first inlet channel 3 and also extends at an angle to the horizontal plane 2. The hydrophilic polymer precursor solution is brought into contact with the hydrophobic fluid 11 at the junction 13 of the first and second inlet channels 3, 7, and they flow together through the outlet channel 15. The hydrophobic fluid 11 disperses the hydrophilic polymer precursor solution 9 into droplets 17 as it moves upward within the outlet channel 15. The dispersed droplets 17 are polymerized into microparticles 19 within the outlet channel 15 and ejected from outlet port 23. In some embodiments, the method can also include running wash fluid 21 over the outlet port 23 in order to stabilize flow within the channels and to prevent clogging of the channels.

Cells can be encapsulated in the microparticles 19 during their fabrication at very high cell densities due, at least in part, to the highly stable flow within the device (achieved, at least in part, due to the vertical orientation of the device). The cells are suspended into the polymer precursor solution 9 at the desired cell density prior to injecting the polymer precursor solution 9 into the first inlet channel 3. The disclosed methods are able to achieve high cell densities within the microspheres, for example, of up to about 60 million cells/milliliter, including about 0.5 million cells/milliliter, about 1 million cells/milliliter, about 5 million cells/milliliter, about 10 million cells/milliliter, about 15 million cells/milliliter, about 20 million cells/milliliter, about 25 million cells/milliliter, about 30 million cells/milliliter, about 35 million cells/milliliter, about 40 million cells/milliliter, about 45 million cells/milliliter, about 50 million cells/milliliter, about 55 million cells/milliliter, and about 60 million cells/milliliter. The resulting cell density in microparticles 19 is the approximately the same as the cell density at which the cells were suspended in the initial polymer precursor solution 9. Because of the high cell density within the formed microparticles 19, the number of cells delivered per volume of microsphere is at least an order of magnitude higher than what can be achieved using conventional techniques. The high cell density lowers the bulk concentration of photocrosslinkable polymer, such that a relatively high power light source may be helpful for thoroughly photocrosslinking the microspheres as they travel through the outlet channel 15.

Cells may be loaded as individual cells, or, in some embodiments, as clusters of cells. Encapsulation of cell clusters can be advantageous, for example, when delivering cells that require connection to other cells for robust survival (such as some stem cells, for example). However, it is difficult to encapsulate cell clusters using conventional microfabrication devices due to the small size of the channels and the likelihood of clogging the system.

It is noted that the disclosed device may have advantages in the fabrication of microparticles 19 that do not include cells. The high uniformity of the size and shape of the disclosed microparticles could have applications in many industries beyond cell therapy.

Because of the vertical orientation of the device, the hydrophobic fluid 11 is able to disperse the aqueous polymer precursor droplets 17 in a highly uniform fashion as it travels upward through the aqueous polymer precursor phase. Such uniformity is an improvement over conventional microfluidic devices used to fabricate microspheres. Conventional microfluidic devices lay flat and the channels are oriented parallel to the horizontal plane. The emulsification is not uniform when the streams are side by side, because it does not benefit from the buoyancy and gravitational differences that, in the disclosed device, pull the hydrophobic phase upward through the aqueous phase to separate the aqueous phase. Buoyancy also becomes a consideration because the channels of the device are larger than those of conventional microfluidic chips. Vertical orientation helps stabilize the system.

In some embodiments, microparticles 19 can be formed at speeds that range from about 3,500 to 35,000 microparticles per hour, including about 3,500, about 4,500, about 5,500, about 6,500, about 7,500, about 8,500, about 9,500, about 10,500, about 11,500, about 12,500, about 13,500, about 14,500, about 15,500, about 16,500, about 17,500, about 18,500, about 19,500, about 20,500, about 21,500, about 22,500, about 23,500, about 24,500, about 25,500, about 26,500, about 27,500, about 28,500, about 29,500, about 30,500, about 31,500, about 32,500, about 33,500, about 34,500, and about 35,000 microparticles per hour. The number of microparticles formed per hour is dependent, in part, upon the flow rate of the polymer precursor solution 9, the hydrophobic fluid 11, and the wash fluid 21. In one embodiment, the flow rates of the above can be: 1 mL/hour for the polymer precursor solution 9, 10 mL/hour for the hydrophobic fluid 11, and 22 mL/hour for the wash fluid 21. Related to both of the above variables (microparticles formed per hour and flow rates of the solutions) is the speed of cell encapsulation. In one embodiment, up to 12 million cells can be encapsulated in 12 minutes (or about up to 60 million cells per hour). The speed of cell encapsulation is also dependent upon the cell concentration and the concentration of polymer precursor solution 9.

As noted above, the dispersed droplets 17 of the polymer precursor solution 9 are polymerized within outlet channel 15. In one embodiment, the polymer precursor solution 9 is photopolymerized using a light source 18. Photopolymerization can be accomplished using visible light or, in alternative embodiments, using UV light or infrared light. The light source 18 can be positioned to transmit light through outlet channel 15. Some embodiments can include mirror 20 positioned on the opposite side of housing 5. After being transmitted from light source 18 through outlet channel 15, light from the light source 18 is reflected off of the mirror 20 and back through the outlet channel 15 to increase the amount of energy for polymerization.

In some embodiments, the microparticles 19 travel through the light beam for a relatively long "residence time," as compared to microparticles formed using conventional microfabrication devices. The long length of outlet channel 15 makes the long residence time possible. The long length of outlet channel 15 is made possible due to the molding technique, as described above. In one embodiment, the residence time of a microparticle (the time spent in the light beam that induces polymerization) is from about 0.5 seconds to about 3 seconds, including about 0.5 seconds, about 0.75 seconds, about 1 second, about 1.25 seconds, about 1.5 seconds, about 1.75 seconds, about 2 seconds, about 2.25 seconds, about 2.5 seconds, about 2.75 seconds, and about 3 seconds. The residence time depends, in part, on the diameter of the outlet channel 15 and the total flow rate within the outlet channel 15.

The microparticles formed by the methods described above can range in size from about 100 micrometers to about 1,000 micrometers across the largest dimension (which, in the case of spherical microparticles, is the diameter). The microparticles can be, for example, about 100 micrometers, about 150 micrometers, about 200 micrometers, about 250 micrometers, about 300 micrometers, about 350 micrometers, about 400 micrometers, about 450 micrometers, about 500 micrometers, about 550 micrometers, about 600 micrometers, about 650 micrometers, about 700 micrometers, about 750 micrometers, about 800 micrometers, about 850 micrometers, about 900 micrometers, about 950 micrometers, and about 1,000 micrometers across a largest dimension. Microspheres formed by the methods described above can be highly uniform in size. For example, the coefficient of variance (COV) for the microsphere diameter can range from about 2% to about 6%, including a COV of about 2%, a COV of about 2.5%, a COV of about 3%, a COV of about 3.5%, a COV of about 4%, a COV of about 4.5%, a COV of about 5%, a COV of about 5.5%, and a COV of about 6%. Microspheres formed by the above methods have a high degree of roundness. For example, in one embodiment, the roundness is greater than 0.95 for all microspheres.

The microparticle aspect ratio can be controlled, for example, by altering the ratio of the flow rates of the polymer precursor solution 9 and the hydrophobic fluid 11. For example, increasing the polymer precursor solution 9 flow rate while holding the hydrophobic fluid 11 flow rate constant will lead to microparticles 19 with higher aspect ratios (i.e., longer microparticles).

The microparticles 19 can be formed of any variety of polymers known in the art. For cell encapsulation, it is advantageous to form the microparticles 19 from a biomimetic material. Examples of biomimetic materials include natural materials, synthetic materials, and combinations thereof. Natural materials include, but are not limited to, materials derived from proteins, polysaccharides, and other derivatives of these substances, such as, for example, collagen, gelatin, glycosaminoglycans (e.g. hyaluronic acid), elastin, fibronectin, laminin, fibrin, and alginates. Synthetic materials include temporally-changing or externally-modifiable materials that can be engineered to provide biomimetic properties. Biomimetic hydrogel materials (natural, synthetic or a combination thereof) can be advantageous because they facilitate diffusion of nutrients and fluids to the encapsulated cells. In some embodiments, the microparticles are formed of polyethylene glycol (PEG), polyethylene glycol diacrylate (PEGDA), PEG-fibrinogen, or gelatin methacrylate (GelMA). However, any photocrosslinkable polymer can be used in the disclosed devices and methods.

Therapeutic compositions can be formed that include the microparticles disclosed herein and described above. The compositions include a therapeutically effective amount of cell-laden microparticles suspended in a carrier fluid. The density of the cells within the microparticles can be up to 60 million cells/milliliter, including about 0.5 million cells/milliliter, about 1 million cells/milliliter, about 5 million cells/milliliter, about 10 million cells/milliliter, about 15 million cells/milliliter, about 20 million cells/milliliter, about 25 million cells/milliliter, about 30 million cells/milliliter, about 35 million cells/milliliter, about 40 million cells/milliliter, about 45 million cells/milliliter, about 50 million cells/milliliter, about 55 million cells/milliliter, and about 60 million cells/milliliter. The cells can be encapsulated as individual cells, or as clusters of cells. If encapsulated as clusters, the cell clusters can range from about 5 cells to about 40 cells, including about 5, about 10, about 15, about 20, about 25, about 30, about 35, and about 40 cells in a cluster. It is possible to load any type of cell into the microparticles, and as such, the disclosure is not meant to be limited to any particular cell type.

The therapeutic compositions comprising microparticles can be used in methods of promoting tissue healing and/or regeneration. In such a method, the compositions are delivered to a target tissue, where microparticles are retained at the target tissue for durations long enough to elicit a therapeutic response. The therapeutic response can be, for example, the integration of one or more of the encapsulated cells into the target tissue (wherein the one or more encapsulated cells release therapeutic paracrine signals to the target tissue). In other applications, the microparticles described herein can be used as an ink in bioprinting or in HTS.

EXAMPLES

Example 1

Microsphere Fabrication

Hydrogels with microscale dimensions, also known as microparticles, are beneficial for many applications, from high throughput in vitro drug testing to in vivo regenerative medicine. Microfluidic devices provide highly efficient methods for scaling up production of uniformly sized microparticles, or microspheres (when the microparticles have a substantially spherical shape). However, the diameter of microspheres is typically limited to below 200 micrometers with traditional microfabrication techniques. To rapidly fabricate larger microspheres with uniform size and geometry distribution, this study presents a novel encapsulation platform that produces uniform and tightly controlled microspheres with diameters above 200 micrometers. This fabrication method is low cost and does not require microfabrication facilities which are conventionally required to produce microfluidic chips using photo-lithographic techniques. The design enables cells to be encapsulated with high cell density and viability, and supports long-term cellular function. Encapsulated cells have been maintained within the microspheres for extended culture times and cell proliferation and elastic modulus of microspheres have been assessed. The established microfluidic encapsulation platform can be leveraged to produce microtissues for a wide range of applications, including supporting injectable cell therapy, bioreactor-based cell expansion and differentiation, and tissue spheroid-based drug-testing assays.

This example describes the design of a custom-built microfluidic platform that overcomes some of the challenges inherit to microfluidic cell encapsulation using standard microfluidic chips. The microfluidic device, which is the major component of the platform, leverages the use of 3D printing for scalable mold production and a custom-developed molding technique that does not require expensive reagents and facilities for photolithography. This new molding technique allows for designing the microfluidic device with a wider range of dimensions on various parts, including junction geometry, channel width, and device length. The ease of device fabrication provided by this technique enables quick testing during prototype development, which is beneficial for understanding the fluid dynamics during microsphere production. With a custom-designed T-junction and readily adjustable assembling components, the platform enables rapid photocrosslinking and production of uniformly sized microspheres over a wide range of diameters from 300 micrometers to 1100 micrometers. This robust platform also has a potential to be used with a variety of natural and synthetic polymers, such as poly(ethylene glycol) (PEGDA), PEG-fibrinogen (PF), and gelatin methacrylate (GelMA), as described below. With the use of eosin Y as the photoinitiator and a full spectrum light source for rapid photocrosslinking, cells were encapsulated at high density (10-60 million cells/mL of hydrogel precursor solution) including horse endothelial colony forming cells (ECFCs), breast cancer cells, or human induced pluripotent stem cells (hiPSCs). The encapsulated cells were evenly distributed through the microspheres and were shown to maintain high viability, robust functional cellular activities, and ongoing proliferative capabilities in long-term encapsulation studies. These results demonstrate the capabilities of this microfluidic encapsulation platform and show its potential for various regenerative medicine applications.

Methods for this Example

Horse Cell Isolation and Culture:

All procedures involving animals were approved by the Auburn University Animal Care and Use Committee. Isolation and culture of horse endothelial colony forming cells (ECFCs) from horse peripheral blood were performed based on a method that was previously published (Salter, et al., 2015). ECFCs were cultured in Endothelial Cell Basal Medium-2 (Lonza) containing 5% horse serum (HyClone) and SingleQuots Kit (Lonza) at 37° C. and 5% $CO_2$. The SingleQuots Kit contained hydrocortisone, hFGF-B, VEGF, R3-IGF-1, ascorbic acid, hEGF, GA-1,000, and heparin. The ECFCs were seeded and expanded on collagen coated tissue culture polystyrene flask. When ECFCs reached 90% confluency, trypsin/EDTA (Lonza) was added to detach the cells at 37° C. for 50 seconds and was neutralized by ECFCs medium followed by centrifugation at 200 g for 5 min. ECFCs were resuspended in medium and then subcultured at a ratio of 1:6 or immediately used for experiment. Cells between passage 2-7 were used for all experiments.

PEGDA Synthesis:

Poly(ethylene glycol) (PEG, 10 kDa; Sigma) was acrylated to form PEG-diacrylate (PEGDA) following a method from a previously published literature (DeLong, et al., 2005). Briefly, PEG was first lyophilized, and then reacted with 0.4 M acryloyl chloride (Alfa Aesar) and 0.2 M triethyl amine (TEA, Sigma) in anhydrous dichloromethane (Acros) under argon overnight. 1.5 M $K_2CO_3$ (Fisher) was added subsequently, and then the solution was separated into aqueous and organic phase. The organic phase was collected and dried with anhydrous $MgSO_4$ (Fisher). The PEGDA was then precipitated by cold ethyl ether, filtered, dried, and stored under argon at −20° C. The degree of acrylation was estimated to be 96.0% by NMR.

PEG Fibrinogen Synthesis:

PEG-Fibrinogen was synthesized by following a previously published method (Almany and Seliktar, 2005). In brief, fibrinogen was dissolved in 8 M urea (Sigma) in PBS (Lonza) solution to a final concentration of 7 mg/mL with pH of 7.4. Then tris(2-carboxyethyl) phosphine (Acros Organics) was added to the solution and reacted at pH of 8. PEGDA was dissolved in urea-PBS to a final concentration of 280 mg/mL and then slowly added to fibrinogen solution to react for 3 hours in dark at room temperature. After reaction, PEGylated fibrinogen was extracted with acetone, followed by centrifugation to get rid of acetone, and then dissolved in urea-PBS again for dialysis. The product was dialyzed in sterile PBS over 24 hours in dark at 4° C., and then stored at −80° C. Protein content was obtained to be 12.5 mg/mL using a Pierce BCA protein assay kit (Thermo Fisher). PEGylation yield was calculated to be 98.1%.

GelMA Synthesis:

Methacrylated gelatin (GelMA) was synthesized following previous protocols (Nichol, et al., 2010; Van Den Bulcke, et al., 2000) with modifications. Briefly, gelatin (Type B, bovine) was mixed at 5% (w/v) into phosphate buffered solution (PBS, Gibco) at 60° C. with constant stirring until fully dissolved. Methacrylic anhydride (MA) was slowly added until the target concentration was reached (15% w/v) and reacted at 60° C. for 2 h. The reaction was stopped with PBS; methacrylated gelatin was dialyzed for seven days and lyophilized for five days. Lyophilized GelMA was dissolved in deuterium oxide (Fisher Scientific) for NMR analysis. $^1$HNMR spectra were collected using a Bruker NMR spectrometer. Before integration, phase and baseline corrections were applied to ensure accurate methacrylation calculations.

3D Printed Bracket for Scale Up Production of Encapsulation Device:

A bracket was 3D printed to hold the mold for creating the junction and the channels for the encapsulation device. The bracket was designed in Blender 2.77 and printed using the LulzBot TAZ 5 with an acrylonitrile butadiene styrene (ABS) filament. Variable sized tubing and wires were used as channel molds to achieve channels of desirable shapes and diameter. After the channel molds were arranged and assembled to achieve the desired junction design, the bracket was fixed on a glass using binder clips. The microfluidic encapsulation device was then created using a Sylgard 184 silicone elastomer kit (Dow Corning) by pouring the mixture of base and cure component into a polystyrene dish containing the pre-assembled bracket and microfluidic channel molds. Air bubbles were degassed by vacuum. Then the PDMS was cured at 60-70° C. for 2 hours. Once the PDMS was cured, the channel molds were removed and the resulting microfluidic encapsulation device was extracted from the bracket. The microfluidic encapsulation device was cleaned and sterilized by sonicating in 70% ethanol before and after each use.

Cell Encapsulation in PEG-Fibrinogen (PF) Microspheres:

Cell encapsulation in PF microspheres was achieved through the custom developed microfluidic polydimethylsiloxane (PDMS) mold described above. Before cell encapsulation, a hydrogel precursor solution was prepared by mixing PF with 1 v/v % of Pluronic P68 (Sigma) solution, 1 v/v % of Eosin Y photoinitiator (Fisher Scientific) solution, 1.5 v/v % triethanolamine (Acros Organics), and 0.4 v/v % of N-vinylpyrrolidone (Sigma). Pluronic F68 is an amphiphilic block copolymer that is commonly used as a surfactant to stabilize the emulsion of microencapsulation which narrows the size distribution of the microspheres. ECFCs were detached from tissue culture flasks, centrifuged, and resuspended in hydrogel precursor solution to create a hydrogel precursor cell suspension with a cell density of 10 million cells/mL.

Cell encapsulation and hydrogel photo-crosslinking were conducted in a biosafety cabinet to keep the process sterile. The microfluidic PDMS mold has a top inlet, a bottom inlet, and one outlet. Syringe pumps were used to flow the hydrogel precursor cell suspension through the top inlet and mineral oil through the bottom inlet. When the two streams met at the junction, emulsification caused the hydrogel precursor cell suspension to separate into microdroplets. The cell-laden microdroplets were crosslinked into microspheres in the outlet channel, using a 2.7 W full spectrum visible light (Prior Lumen 200). A mirror was placed behind the microfluidic device near the outlet to aid the crosslinking by reflecting the light that passed through the device. The microspheres were washed down from the outlet with prewarmed Dulbecco's Modified Eagle Medium (DMEM) by using a third syringe pump setting at 22 mL/hr. The microspheres were then washed twice with DMEM by centrifugation at 200 g for 3 min to remove the residual mineral oil and cultured in medium on a collagen coated well plate at 37° C. and 5% $CO_2$.

Microsphere Geometry Characterization:

The uniformity of the microspheres was evaluated by measuring their maximum diameter and roundness on one and three days after cell encapsulation. Three batches of microspheres with at least 30 microspheres per batch were measured and the measurements were performed using ImageJ. Roundness measured in ImageJ is defined by $$\text{Roundness} = \frac{\text{Area}}{\pi \times \text{Major axis}^2} \quad \text{(Equation 5)}$$

Uniformity was also analyzed by coefficient of variance (COV) which is defined by $$\text{Coefficient of variance} = \frac{\text{Standard deviation}}{\text{Mean}} \quad \text{(Equation 6)}$$

Post-Cell Encapsulation Cell Viability Assay:

Cell viability after encapsulation was assessed by Live/Dead viability/cytotoxicity kit (Invitrogen) and XTT Cell Viability Assay Kit (Biotium). For Live/Dead staining, microspheres collected immediately after encapsulation were incubated for 30 min with calcein AM and ethidium homodimer-1, and then Z-stack-images were obtained with fluorescence microscopy. Three regions with same size (250×250 micrometers) were randomly selected on each microsphere using ImageJ and viability was then assessed by counting Live/Dead stained cells through the optical slices along the z-axis for the depth about 550 micrometers. To further estimate the cell viability and proliferation continuously in a relatively long time range, XTT assay was used. Microspheres containing ECFCs were aliquoted into 96-well-plate with one microsphere per well. 100 microliters of pre-warmed medium and 25 microliters of XTT working solution were then added to each well. After incubation of the well for 18 hours at 37° C., absorbance signal of the sample was measured with a microplate reader (BioTek). Microspheres were assessed on day 0, 7, 14 after encapsulation with XTT assay.

Scanning Electron Microscopy:

The ultrastructural features of the microspheres and the cell-laden microspheres were visualized through scanning electron microscopy (SEM). Microspheres were washed with PBS, fixed with 4% glutaraldehyde for 1 hour and then fixed with 2% osmium tetroxide (Electron Microscopy Sciences, EMS) for 1 hour, all at room temperature. The fixed microspheres were frozen in liquid nitrogen for 2 minutes and then dried in a freeze dryer (Labconco). Dried samples were mounted on carbon taped-aluminum stubs, sputter-coated with gold (Pelco SC-6 sputter coater) and imaged using scanning electron microscope (JEOL JSM-7000F).

Microsphere Stiffness:

In order to measure the Young's modulus of the hydrogel microspheres, they were subjected to compression testing under physiological conditions using a MicroSquisher (CellScale). Briefly, ECFCs encapsulated in microspheres were culture for 1 or 3 days prior to mechanical testing. These microspheres were then loaded onto the MicroSquisher platform maintained at 37° C. in PBS, preconditioned for compression testing and made to undergo cycles of compression and relaxation at a rate of 2.5 micrometers/s for a minimum of 15% strain. The force-displacement data obtained from the stress were converted to stress-strain curves and the lower portion of the curve (5-15% strain) was used to estimate the Young's moduli of microspheres.

Immunocytochemistry:

Encapsulated horse ECFCs were evaluated for the expression of cell proliferation maker Ki67 with indirect immunofluorescence assay (IFA). Microsphere cryosections containing ECFCs were fixed with 4% paraformaldehyde (PFA) solution and rinsed with PBS solution. ECFCs were then permeabilized with PBS-T containing 0.2% Trition X 100 (Sigma) in PBS for 30 minutes and blocked with 3% FBS at 4° C. overnight. The encapsulated cells were then incubated at room temperature for 2 hours with primary antibody solution which was rabbit anti-Ki67 (Abcam) at 1:100 dilution in 3% FBS solution. After incubation, cells were washed with PBS-T before applying secondary antibody. Alexa Fluor 680-conjugated goat anti-rabbit IgG diluted at 1:200 in 3% FBS solution was used as secondary antibody and incubated with cells at room temperature in dark for 2 hours. Cells were counter stained with DAPI, washed with PBS, mounted with ProLong Gold antifade reagent (Life technologies), and imaged with fluorescent microscopy.

Cryopreservation of ECFC Encapsulated Microspheres:

Encapsulated horse ECFCs were cultured in medium at 37° C. and 5% $CO_2$ for 2 days. Then the ECFC-laden microspheres were collected through centrifugation for 3 min at 200 rcf. Supernatant medium was removed and cryoprotectant solution was added to resuspend the microspheres. The cryoprotectant solution contained 10% (v/v) dimethyl sulfoxide (DMSO, Sigma) and 90% (v/v) FBS. The Cryogenic Vials (Nalgene) containing ECFC-laden microspheres were placed in Mr. Frosty Freezing Container (ThermoFisher Scientific) and stored in −80° C. freezer (VWR) overnight. On the second day, Cryogenic Vials were transferred into liquid nitrogen. When thawing, the cryogenic vials were taken out from liquid nitrogen and warmed up quickly in 37° C. water bath for 1-2 min. Cryoprotectant solution was removed by centrifugation (3 min at 200 rcf) and pre-warmed Phenol Red-free DMEM was added to rinse the ECFC-laden microspheres for 5 min. After washing once with DMEM, microspheres were resuspended in fresh DMEM and incubated for 15 min at 37° C. and 5% $CO_2$ before assessing viability of encapsulated ECFCs.

Results for this Example

Figure 6:
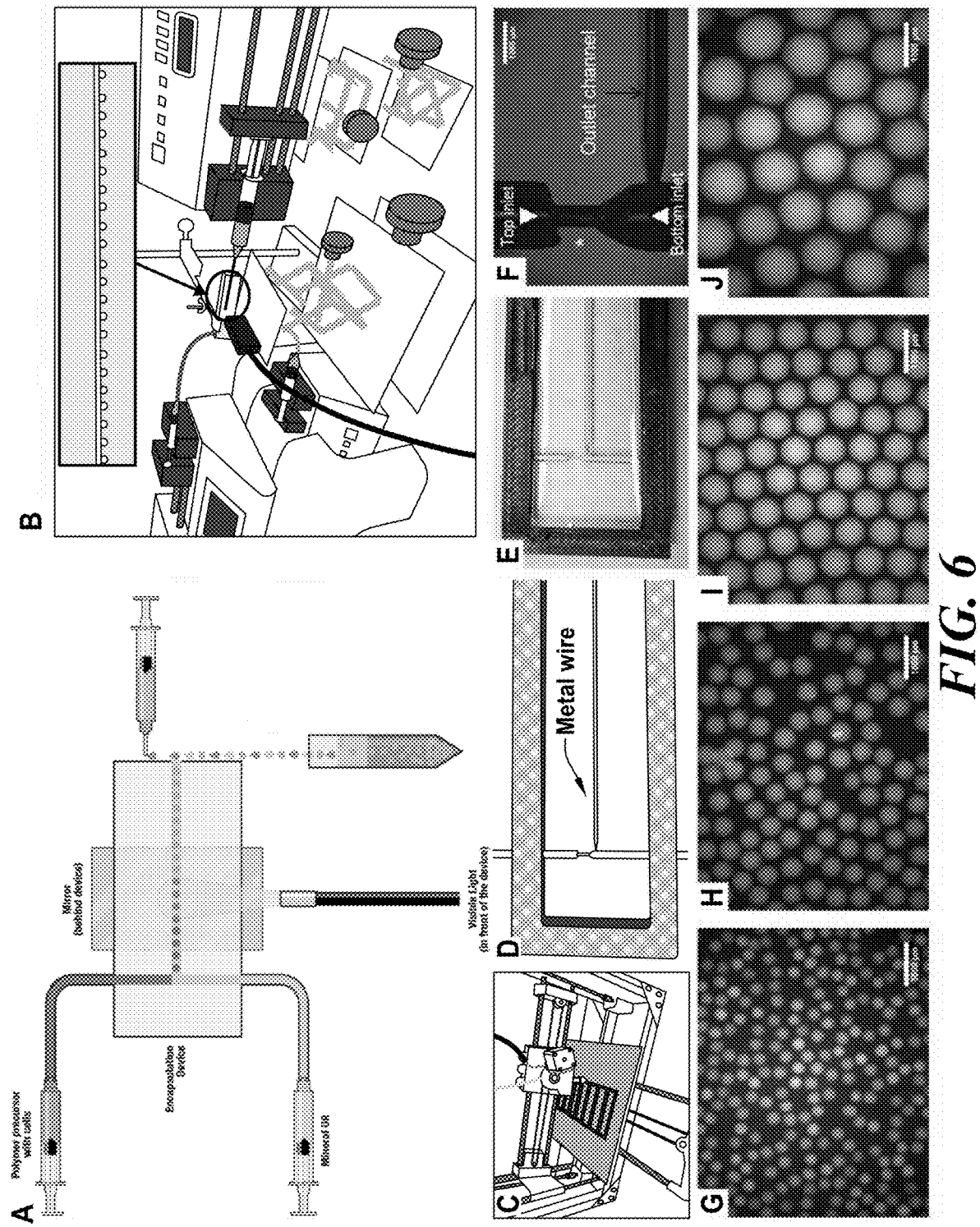
FIGS. 6A-6J. Microfluidic encapsulation platform using a novel custom design and device molding technique enables production of uniform hydrogel microspheres with a wide range of diameters.

Microfluidic Encapsulation Platform Using a Novel Custom Design and Device Molding Technique:

A novel microfluidic encapsulation platform was developed in this study. As shown in FIG. 6A-6B, the microfluidic encapsulation platform is composed of three syringe pumps, a collection vessel, and the novel polydimethylsiloxane (PDMS) microfluidic device. Polymer precursor flows in through the top inlet channel and the oil carrier flows in through the bottom channel. The flow rate of the polymer precursor and oil can be independently adjusted, providing control over the polymer precursor/oil flow rate ratio. Microspheres are formed at the junction due to emulsification and then photo-crosslinked in the microfluidic device, where a wide spectrum visible light with a liquid light guide is employed. At the end of the outlet, the microspheres hydrogels are washed down and collected in media.

This encapsulation platform uses a high power visible light source to perform rapid photocrosslinking. Compared to other microfluidic platforms, microspheres here have a much shorter residence time passing through the light beam. It takes approximately 1 s for photocrosslinking, whereas other platforms take up to 20 s or longer. A range of power output (0.5 W→3 W, 10%-100%) of the light source has been tested for photocrosslinking of the microspheres. Microspheres have a residence time approximately 1 s passing through the light beam depending on the diameter of the outlet channel and total flow rate. In order to achieve rapid photocrosslinking, a minimum of 2.7 W was used to form microspheres with stable boundaries and structural integrity. Power output can be increased for photocrosslinking without affecting the consistency of microsphere size and geometry.

When employing conventional microfabrication techniques, the maximum diameter of fabricated microspheres is generally determined by the maximum height of microfluidic channels, which is usually around 200 µm (Velasco, et al., 2012). This limitation is a result of the channel height being dictated by the maximum thickness of photoresist that can be casted onto a wafer and depends on the series and choice of the photoresist. As a result, traditional microfluidic device fabrication is not suitable when microspheres with larger diameters are desired. This study overcomes the size limitation by employing a molding technique and designing a suitable T-junction in the fabrication of the microfluidic encapsulation device.

The microfluidic device channels are assembled with easily acquired components (tubing, wires, custom bracket, binder clips) as described in above. Numerous iterations were able to be performed in the design of the reported device due to the ease of employing the molding technique. In order to hold the assembly of the channel molds together and control the dimension of the resulting encapsulation device, a reusable channel mold-holding bracket was designed and 3D printed (FIG. 6C) with ABS. The 3D-printed bracket is good for consistent and scale-up production of microfluidic encapsulation devices. In addition, the cost of all components of the channel molds ($0.80/device) and the bracket ($0.16/device) is relatively low (FIG. 6D). After the PDMS is cured, the channel molds can be easily removed (FIG. 6E). The amount of PDMS used to form each encapsulation device is 14 g ($1.94). The total cost of each encapsulation device is estimated to be $2.90. This encapsulation device and methods of making it are easily replicated because fabrication does not involve photolithography, which requires expensive microfabrication facilities.

The T-junction and the channels are molded with Teflon tubes and metal wires. In conventional T-junction designs, the two inlet channels are perpendicular to each other, with the discrete phase entering the continuous phase channel at an angle and then progressing linearly to the outlet. Here, however, the discrete and continuous phase inlet channels are collinear with each other and the joint outlet channel is perpendicular to both inlets. This unique design leverages the simplicity of the T-junction design while providing additional control over microsphere size and operational stability, typically only achieved using much more complex flow focusing microfluidic designs. In particular, manipulation of the inlet flow ratio enables control over microsphere size. The top inlet channel was designed to contain a restriction region as indicated by an asterisk in FIG. 6F. This is implemented to stabilize the precursor/oil interface prior entering the outlet channel as the denser precursor tends to escape from the flow and form unwanted droplets that sink to the bottom inlet. Beneath the restriction region is a conical part instead of a cylindrical part, which was introduced to eliminate the dead volume of hydrogel precursor solution. The metal wire has a tapered end that can be inserted into the Teflon tube forming the T-junction. In addition, the tapered end slightly increases the flow velocity at the T-junction which aid in microsphere formation.

Since rapid photocrosslinking requires a high-power light source, the outlet channel length in this design was increased to achieve an optimal distance between the T-junction and the light source to minimize the influence of light back scattering. As readily facilitated by the employed molding technique, the device length was extended to 10 cm, which provided the distance between the light source and the T-junction needed to prevent light from traveling down the interior of the outlet channel.

Additionally, comparing to most microfluidic devices, the one in this study is oriented vertically instead of laying flat horizontally. According to a preliminary study during platform development, such orientation allows the less dense oil, which is flowing in from the bottom inlet, to separate the denser hydrogel precursor/cell-precursor suspension, which is flowing in from the top inlet, in a more stable manner. With all the new designs mentioned above, the microfluidic encapsulation system is able to produce microspheres with a wide range of diameters from 300 µm to 1100 µm (FIG. 6G-6J). The resulting cell-laden microspheres can be employed for a wide range of applications, including injectable cell delivery, bioreactor-based cell expansion and differentiation, and tissue spheroid-based drug-testing assays.

Besides the design of the encapsulation device, the continuous downward washing of microspheres with DMEM at the outlet into the collection tube also contributes to stabilize the system flow, and helps to create uniform microsphere diameter and geometry. Furthermore, such stable system flow also enables the formation of a range of microsphere diameters within a range of flow rates by using a single design. More details will be discussed in the later section. Taken together, by using the microfluidic device with a novel custom design and molding technique, the encapsulation platform can overcome the limitation of traditional microfluidic chip-based production and produce uniform microspheres with a wide range of diameters.

Figure 7:
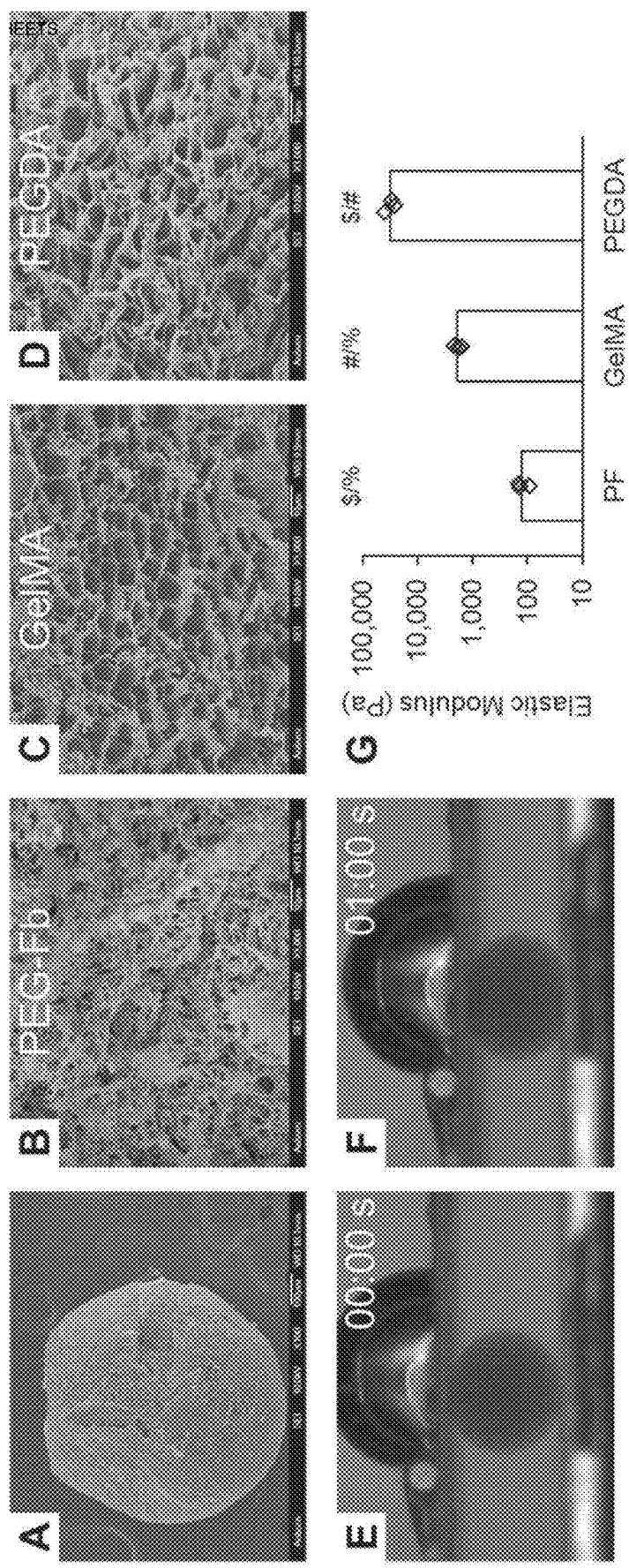
FIGS. 7A-7G. Microspheres were able to be formed using a range of photocrosslinkable hydrogel materials. Porous structure of the hydrogel scaffolds shown by SEM of (FIG. 7A) GelMA microspheres (100×), (FIG. 7B) PF microspheres (1,000×), (FIG. 7C) GelMA microspheres (1,000×), and (FIG. 7D) PEGDA microspheres (1,000×).

The Established Microfluidic Encapsulation Platform is Compatible with Various Materials:

This is important because numerous types of photocrosslinkable polymers have been widely employed for tissue engineering applications (Nguyen and West, 2002). Each of these materials has their own advantages, depending on the desired application. Here we examined the photocrosslinkable hydrogel materials PF, GelMA, and PEGDA. These polymers were selected to demonstrate the ability of this setup to be compatible with various polymers. The presence of the acrylate groups allows them to crosslink and form hydrogels through radical chemistry (Odian, 2004). The photoinitiator in polymer precursor solution triggers the photocrosslinking reaction once exposed to light. Acellular microspheres were fabricated with these polymers, and SEM images of the microspheres showed typical porous structure that are present in hydrogel scaffolds (FIG. 7A-7D) (Annabi, et al., 2010). Using the same parameters for microsphere production, microspheres formed using the three different polymers were evaluated for their elastic moduli by a compression test (FIGS. 7E and 7F). All microspheres were observed to regain their initial geometries following compression. Elastic moduli of PF, GelMA, and PEGDA were found to be 127.3±24.4 Pa, 1894±257 Pa, and 31,800±5,280 Pa respectively (FIG. 7G). This demonstrates the capability of translating this microfluidic encapsulation platform to various polymer systems.

Figure 8:
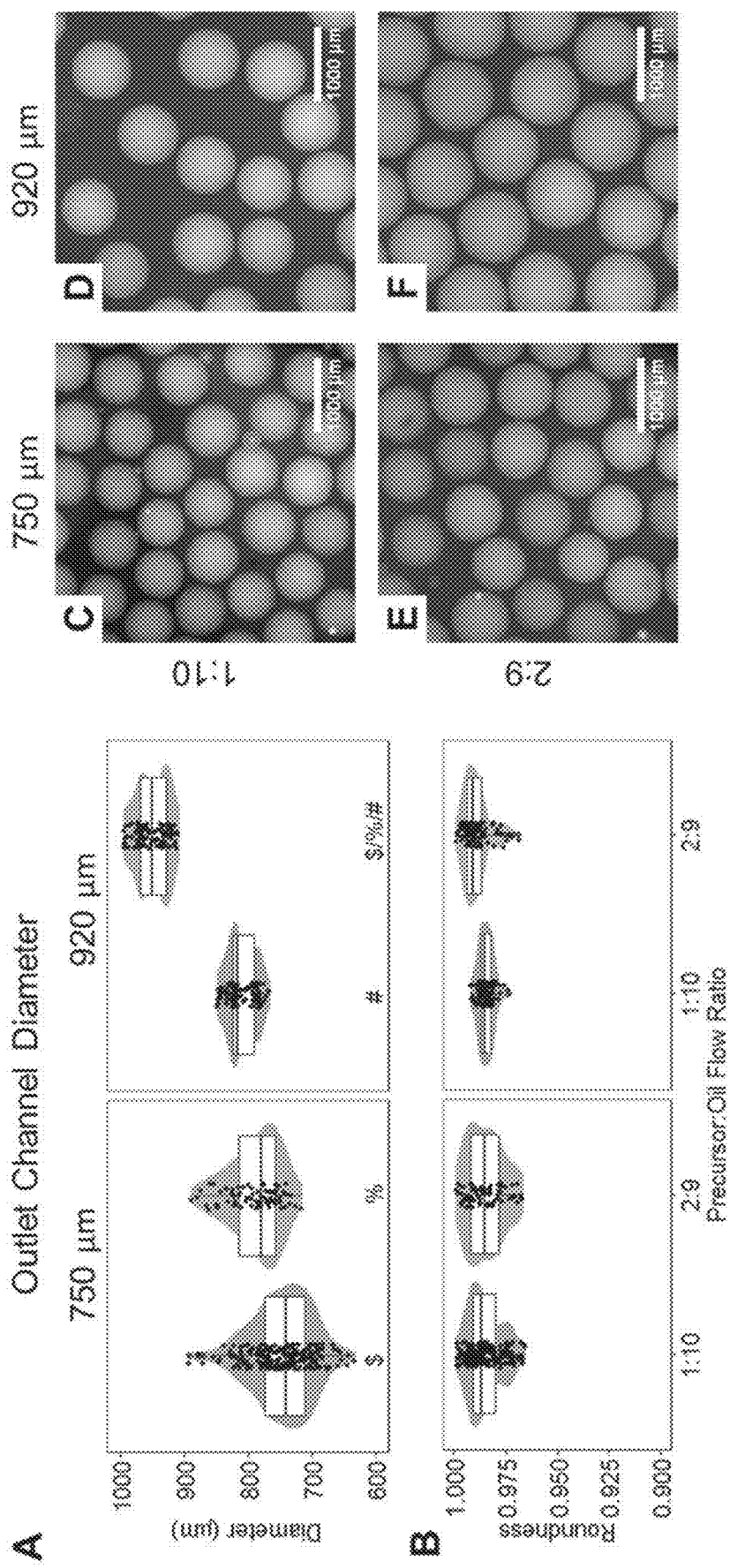
FIGS. 8A-8F. Encapsulation device provides tight control over microsphere diameter.

Straightforward Control of Microsphere Diameters by Varying Inlet Flowrates and Outlet Channel Diameter:

Besides fabricating microspheres with various materials, this encapsulation device also provides tight control in microsphere diameter. Based on extensive testing during platform development using multiple microfluidic device designs, the ratio of precursor to oil flow rate and outlet channel diameter were found to be important parameters in controlling microsphere diameter. For example, by changing the precursor:oil flow rate ratio from 1:10 to 2:9 in an encapsulation device with 750 µm outlet channel diameter, the microsphere diameter increased from 746±46 µm to 788±40 µm (FIG. 8A). Similarly, microspheres increased in diameter from 811±22 µm to 951±25 µm when changing the precursor: oil flow rate ratio from 1:10 to 2:9 in the encapsulation device with 920 µm outlet channel diameter (FIG. 8A). These results demonstrate the diameters of microspheres can be changed by just varying the precursor: oil flow rate ratio without changing the outlet channel diameter. On the other hand, when employing the same flow rate ratio, the resulting microspheres were bigger in size as the outlet channel diameter increased (FIG. 8A). Roundness were found to be above 0.95 for all microspheres (FIG. 8B). Representative images are shown in FIG. 8C-8F.

By employing the molding technique used here in microfluidic device fabrication, the outlet channel diameter can be altered simply by selecting a different wire size for molding. The metal wire used as a channel mold for molding the outlet channel is commercially available in a wide range of diameters (250-25000 µm). This wide range of options is highly advantageous for maximizing microsphere diameter selection for specific applications, which provides much greater flexibility than microfabrication. Together, these results suggest that the microsphere diameters can be readily controlled by adjusting inlet flowrates and altering outlet channel diameter.

Figure 9:
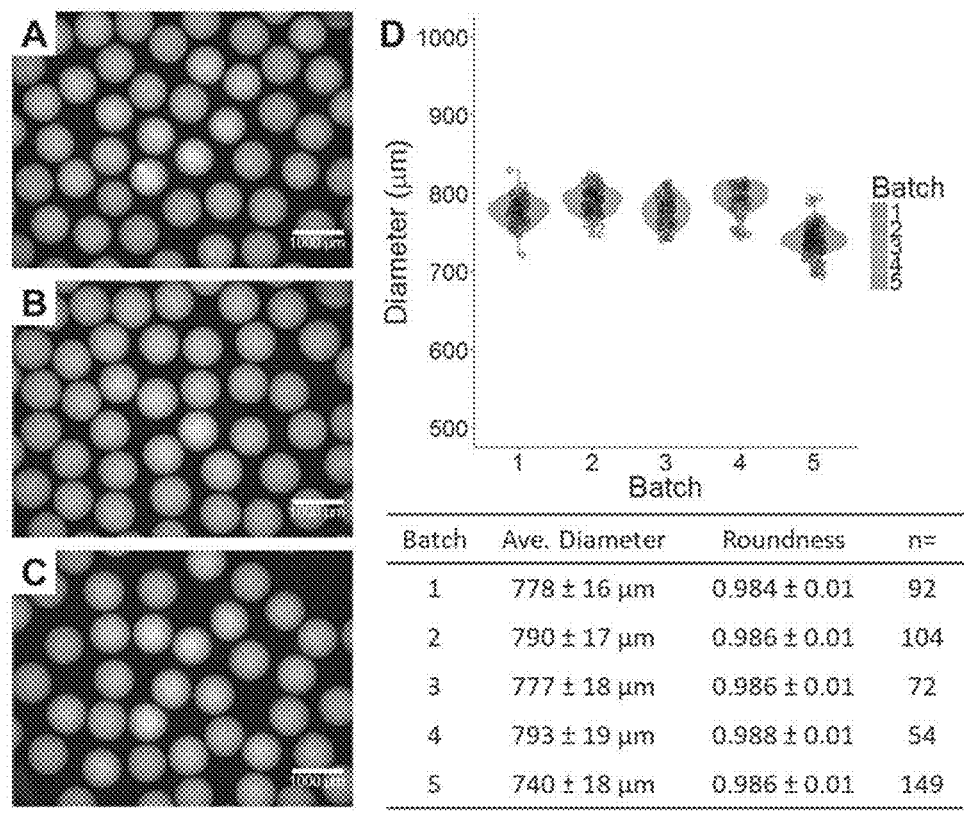
FIGS. 9A-9D. Microfluidic encapsulation platform enables high uniformity of microspheres both between and within batches.
Figure 10A:
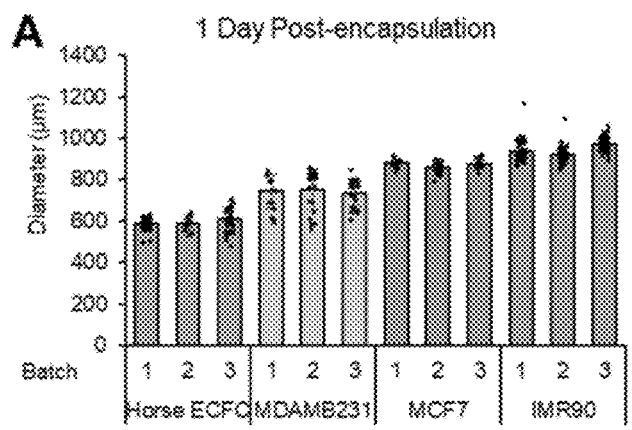
FIGS. 10A-10C show batch-to-batch comparisons of multiple microsphere batches for each cell type.
Figure 10B:
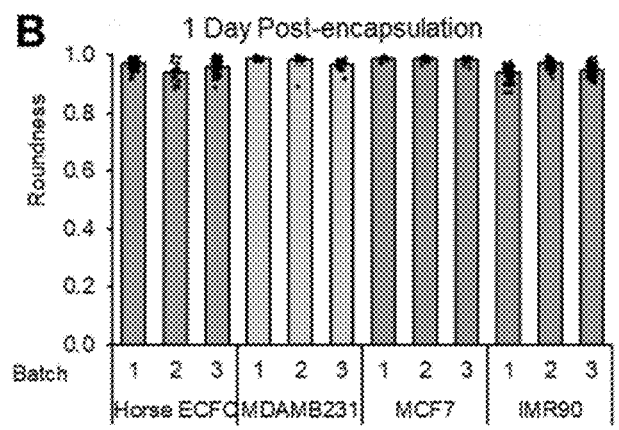

High Uniformity of Microspheres within and Between Batches:

It is important to tightly control the size and shape of microspheres in various applications. For clinical applications involving injections of the cell-laden microspheres (which require a large number of cell-laden microspheres for therapeutic effect) high microsphere uniformity over multiple batches helps to ensure a smooth injection. For high-throughput drug screening, tight control over size and shape of microspheres enables better comparison of the drug effects. To show the microfluidic encapsulation platform presented in this study enables high uniformity of microspheres both between and within batches, horse ECFCs were encapsulated within PF hydrogel microspheres. As shown in FIG. 9A-9C, ECFCs-laden microspheres, which are shown in fluorescent green, were highly consistent. A quantitative analysis (FIG. 9D) compared 5 batches of ECFCs-laden microspheres that were prepared individually, the average diameter ranged from 740 µm to 793 µm between batches with low variance within each batch. The roundness was above 0.980 with the standard deviation of 0.01 for all 5 batches. Collectively, these results show that the microfluidic encapsulation platform has a tight control on microsphere diameter and roundness both within and between batches. Additional data demonstrating uniformity in diameter and roundness across batches with varying cell types is shown in FIGS. 10A and 10B.

Figure 11:
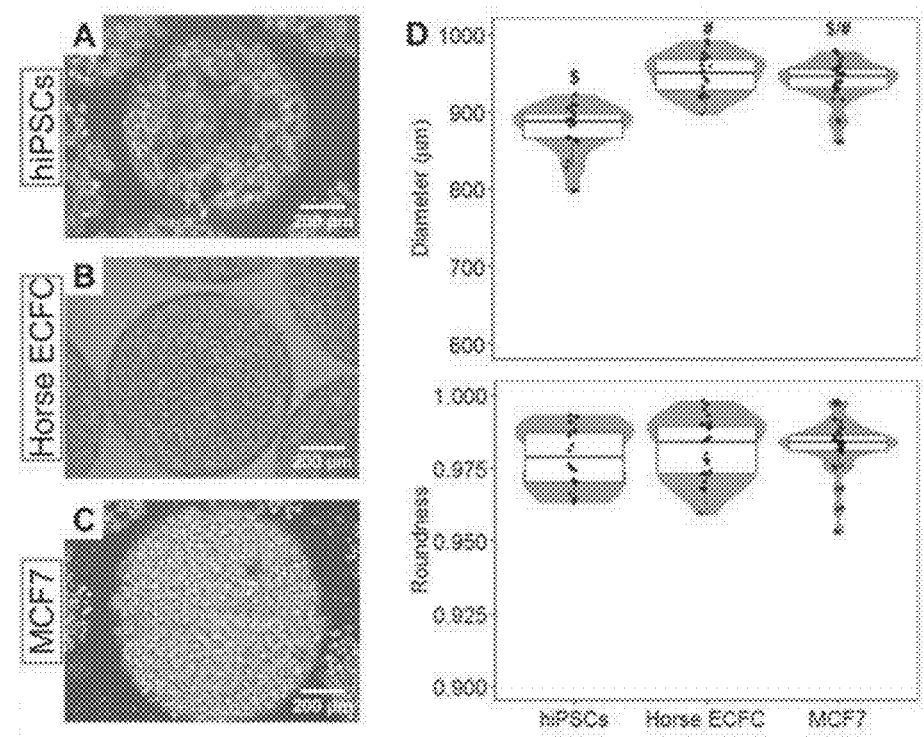
FIGS. 11A-11D Uniform microspheres with high cell densities can be fabricated for a range of cell types using the microfluidic encapsulation platform. Phase contrast images of (FIG. 11A) horse ECFC (10 million cells/ml) (FIG. 11B) MCF7 breast cancer cells (20 million cells/ml), and (FIG. 11C) hiPSCs (25 million cells/ml) encapsulated in PF microspheres. Encapsulation of single cells (ECFCs, MCF7 cells) and cell clusters (hiPSCs) was readily achievable.

The Microfluidic Platform Enables Encapsulation with High Cell Density:

Encapsulation of cells at high densities and in clusters, rather than as single cells, typically poses great challenges when attempting to form uniform microspheres. This is either due to the junction becoming clogged or changes in the precursor viscosity. In order to show that the encapsulation device presented in this study operates robustly even under these challenging situations, microspheres were formed using PF precursor solution with high cell densities. The results of this study are summarized in Table 1. Horse ECFCs, MCF7, MDA-MB-231, and hiPSC clusters were encapsulated at 10 million cells/ml, 20 million cells/ml, 20 million cells/ml, and 25 million cells/ml respectively. The cell clusters did not clog the junction. Resulting microspheres were found to have similar diameters post-encapsulation as shown in FIGS. 11A-11C. Diameters of hiPSCs, horse ECFC, and MCF7 microspheres are 878±29 µm, 957±31 µm, and 939±26 µm (n>20 microspheres for each cell type), which all show low standard deviation. High degree of roundness (above 0.95) was maintained for all cell types (FIG. 11D). Furthermore, cancer cells with 60 million cells/mL can be encapsulated without clogging the encapsulation device and no significant effect was observed on both microsphere geometry and shape (data not shown). The results indicate that the microfluidic platform enables encapsulation with high cell densities. This sheds light on broadening the applications of cell-laden microspheres, including cell delivery, stem cell differentiation, and cancer tissue modeling.

TABLE 1

High cell density

| Cell Type | Initial Cell Concentration Used [×10⁶ cells/mL] | Diameter (µm) (COV) | Roundness (COV) | Potential Applications | Evaluation Time Points [Day] |
| --- | --- | --- | --- | --- | --- |
| ECFC | 10 | 957 ± 31 (0.03) | 0.98 ± 0.01 (0.01) | Cell delivery | 1, 3 |
| hiPSC | 25 | 878 ± 29 (0.03) | 0.98 ± 0.01 (0.01) | Stem cell differentiation | −2, 5, 10 |
| Non-metastatic breast Cancer (MCF7) | 20 | 939 ± 26 (0.03) | 0.98 ± 0.01 (0.01) | Non-metastatic cancer tissue model | 1, 7, 14 |
| Metastatic breast Cancer (MDA-MB-231) | 20 | No data | No data | Metastatic cancer tissue model | 1, 7, 14 |

Figure 12:
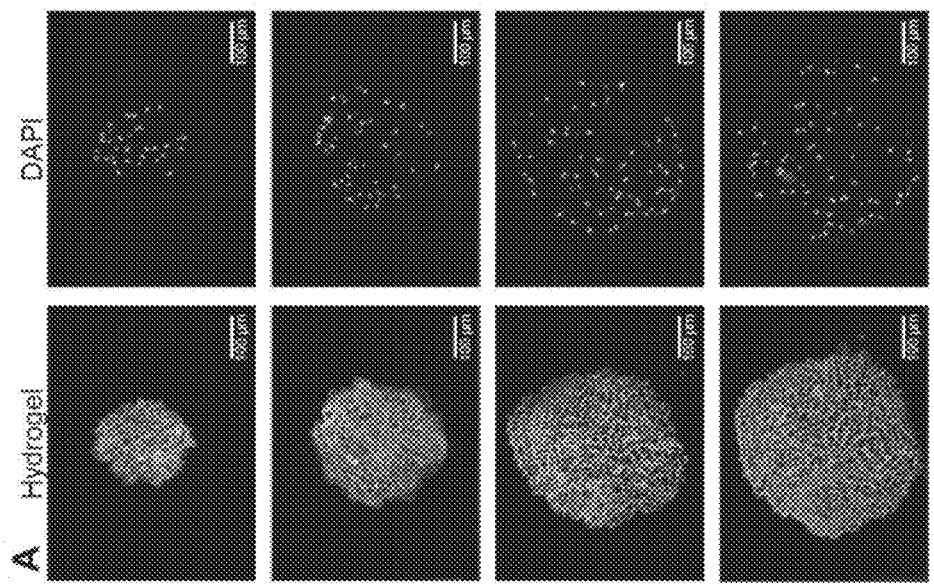
FIGS. 12A-B. Cells were distributed evenly throughout the microsphere volume and high cell viability was maintained post-encapsulation.
Figure 12:
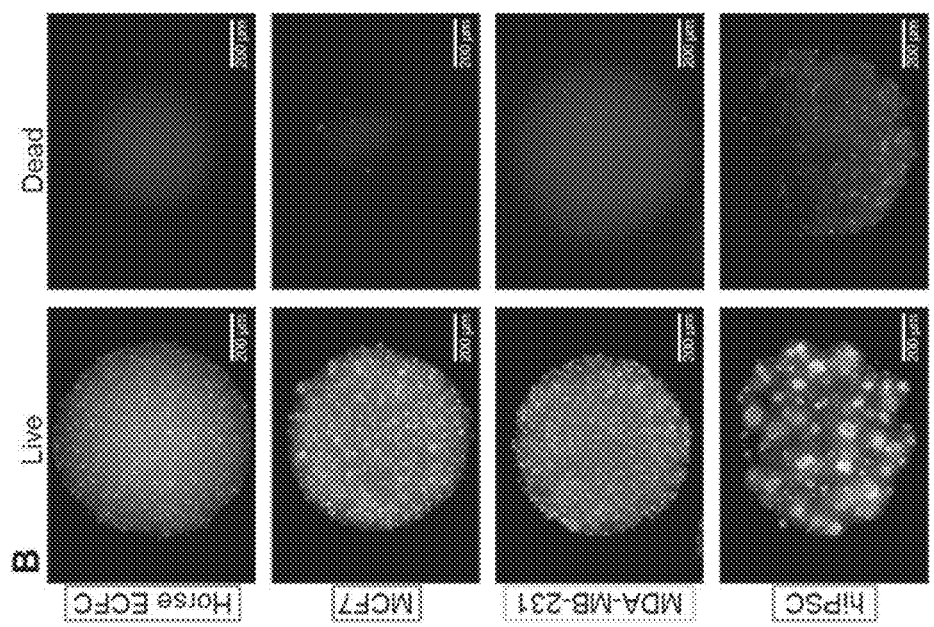
Figure 12:
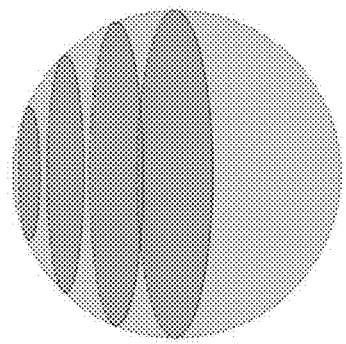

Even Cell Distribution with High Cell Viability Post Encapsulation:

Cell distribution within the microspheres was assessed to ensure the cells were evenly distributed. Horse ECFCs microspheres were prepared and cryosectioned after encapsulation. Cells were found to be distributed evenly throughout the microsphere volume as shown in FIG. 12A.

Cell viability was evaluated post-encapsulation to assess the effect of device-associated shear stress and light exposure on the cells during encapsulation with this platform. Horse ECFCs, MCF7, and MDA-MB-231 were found to have a high post-encapsulation viability of 97±1%, 98±1%, and 97±1%, respectively. Clusters of hiPSC encapsulated in microspheres were also found to have high viability, as shown in FIG. 12B (numeric quantification of hiPSC viability requires dissociation of the cell clusters, which inherently reduces viability). Collectively, these results show that the cells can be encapsulated with even cell distribution as well as high cell viability using the established microfluidic encapsulation system.

Figure 10C:
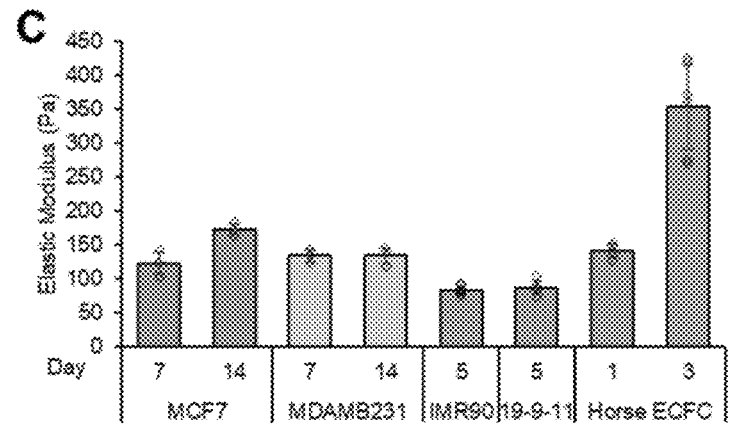
Figure 13:
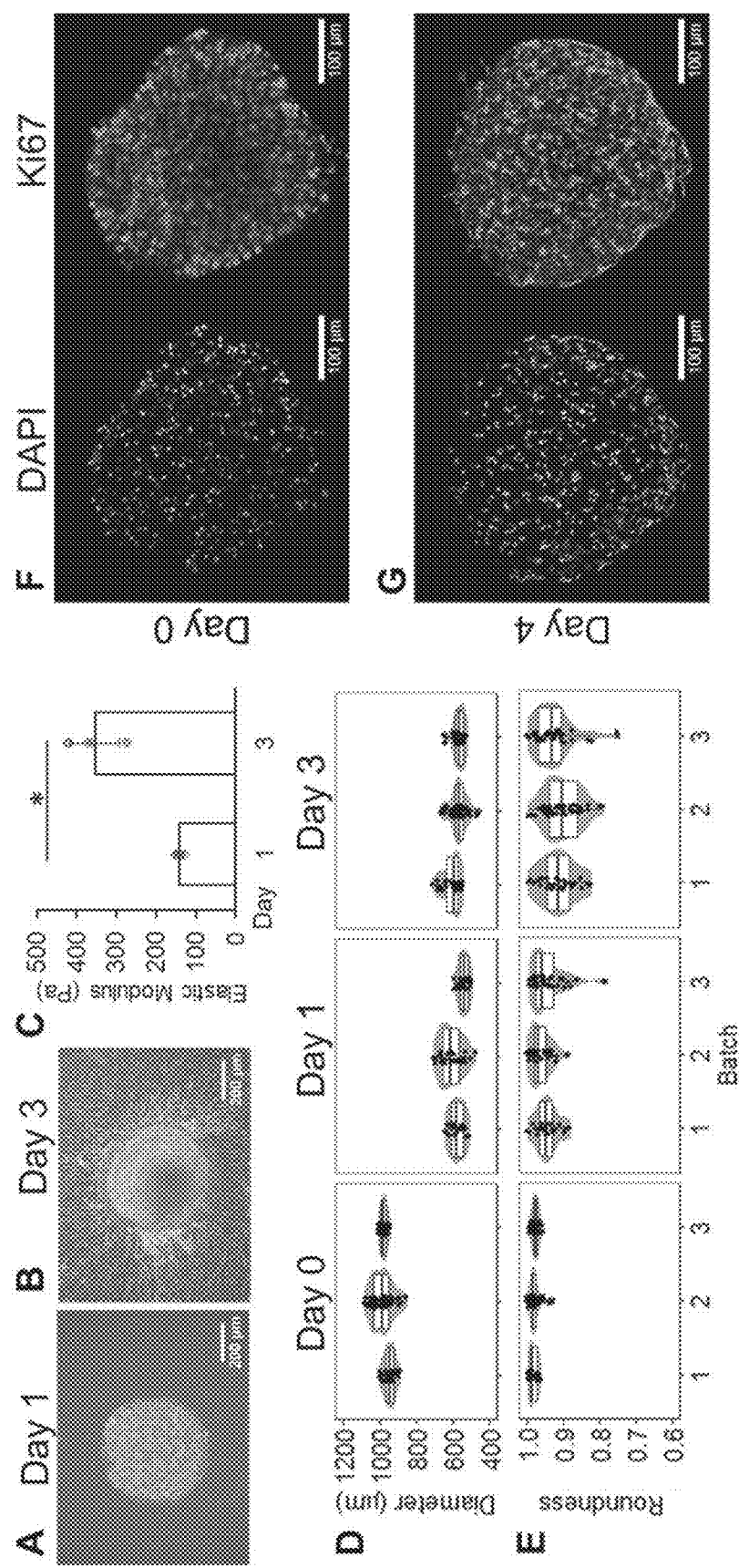
FIGS. 13A-13G Cells maintained high proliferative capability post-encapsulation in PF microspheres.
Figure 14:
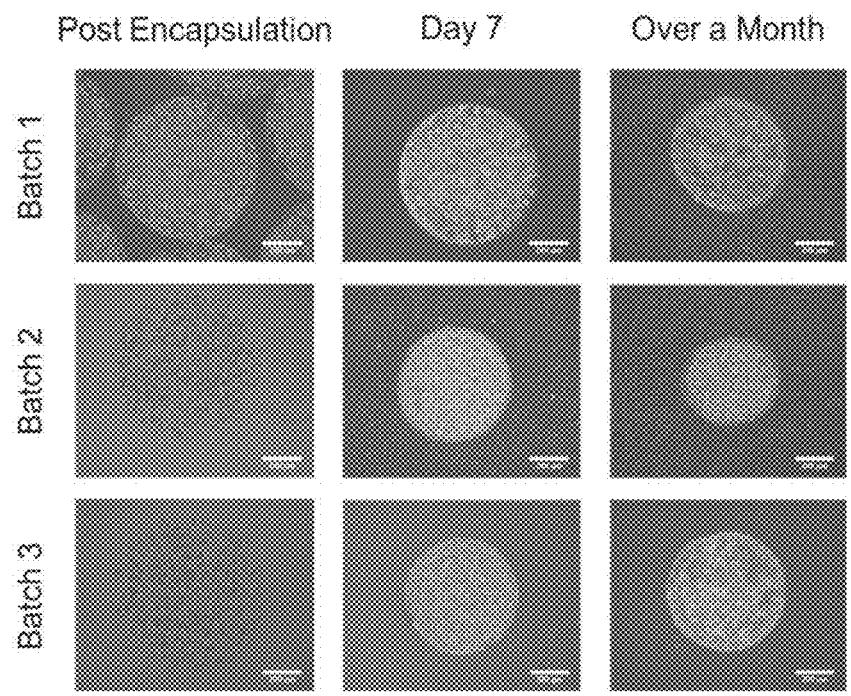
FIG. 14 shows images of ECFCs thriving in microspheres that have been cultured for over a month.

Cells Maintain Active Cellular Activities Post Encapsulation:

Cells maintain active cellular activities such as proliferation and migration after being encapsulated. In order to demonstrate this, horse ECFCs were encapsulated in PF hydrogel microspheres and assessed for their proliferative capability. When culturing the ECFC-laden microspheres in collagen-coated well plate, ECFCs were seen to align along the edge of the hydrogel microspheres 1 day after encapsulation (FIG. 13A). On day 3, cell outgrowth from the microsphere was observed, and these cells formed a confluent layer (FIG. 13B). The stiffness of the microspheres was also assessed in terms of elastic modulus on both day 1 and 3 (FIG. 13C). The elastic modulus of the ECFC-laden microspheres increased significantly from day 1 to day 3, indicating the encapsulated cells were actively remodeling the microspheres. The assessment of elastic modulus on microspheres with other cell types is shown in FIG. 10C. Additionally, size and shape of the microspheres from 3 batches were quantified on day 0, 1, and 3 FIGS. 13D-13E). Both the diameter and roundness of the microspheres decreased along with time, demonstrating the active cellular activities of encapsulated cells. The microspheres were cultured over a month and more data is shown in FIG. 14. In order to directly show that the encapsulation system did not affect cell proliferation in PF, cell proliferation marker Ki67 was stained and quantified. As shown in FIG. 13F-13G almost all cells were stained positive for Ki67 on both day 0 and day 4 post-encapsulation. Taken together, these results show that the cells can maintain active cellular activities after being encapsulated using the microfluidic platform.

Figure 15:
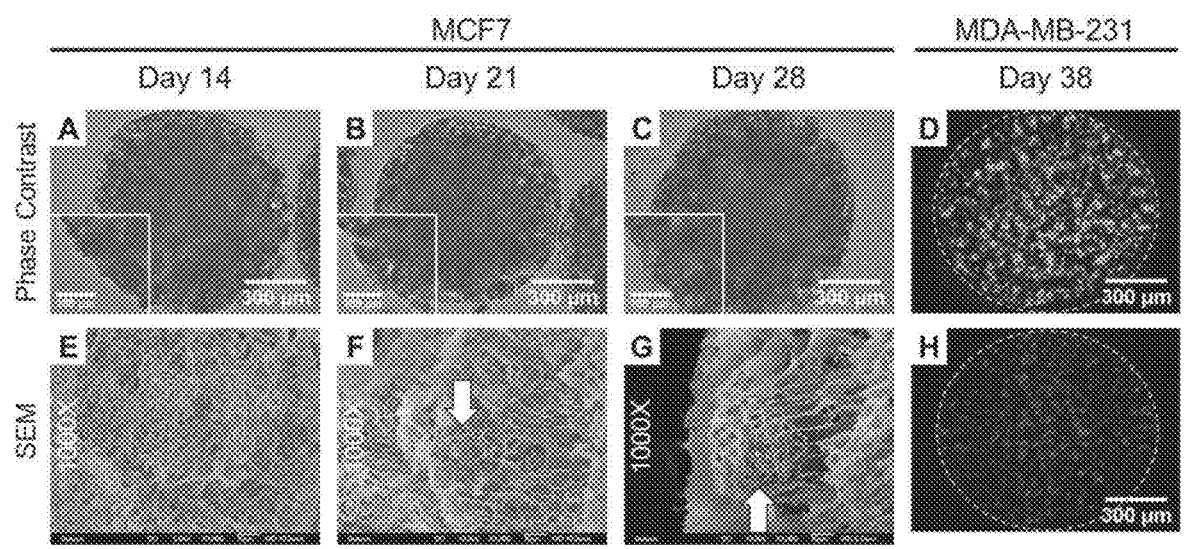
FIGS. 15A-15H Encapsulated cells were able to be cultured for a long term.

Microspheres for Long Term Cell Culture:

Encapsulated cells can be cultured long-term within the microspheres. To demonstrate the capability of the established encapsulation platform to support long-term culture, MCF7 breast cancer cells and MDA-MB-231 breast cancer cells were separately encapsulated in PF hydrogel microspheres (20 million cells/ml) and cultured for at least a month. MCF7 with rounded morphology, grew as distinct local colonies with tight cell packing and were distributed uniformly within microspheres. Colony outgrowth of MCF7 cells was observed under phase contrast microscope from day 14 to day 28 after encapsulation as shown in FIG. 15A-15C. From more detailed SEM images, outgrowth of MCF7 cell colonies from the hydrogel materials were seen clearly (FIG. 15E-15G), indicating the proliferation of cancer cells in long-term culture. Encapsulated MDA-MB-231 cells were cultured longer for 38 days, and majority of the cells were found to be alive by conducting a cell viability assay (FIG. 15D, 15H). Together, these results suggest that microspheres produced using the microfluidic encapsulation platform can be used for long term cell culture.

REFERENCES CITED IN THIS EXAMPLE

Almany, L. and Seliktar, D. Biosynthetic hydrogel scaffolds made from fibrinogen and polyethylene glycol for 3D cell cultures. *Biomaterials* 2005; 26(15):2467-2477.

Annabi, N., et al. Controlling the Porosity and Microarchitecture of Hydrogels for Tissue Engineering. *Tissue Engineering Part B-Reviews* 2010; 16(4):371-383.

DeLong, S. A., Gobin, A. S. and West, J. L. Covalent immobilization of RGDS on hydrogel surfaces to direct cell alignment and migration. *Journal of Controlled Release* 2005; 109(1-3): 139-148.

Nichol, J. W., et al. Cell-laden microengineered gelatin methacrylate hydrogels. *Biomaterials* 2010; 31(21):5536-5544

Nguyen, K. T. and West, J. L. Photopolymerizable hydrogels for tissue engineering applications. *Biomaterials* 2002; 23(22):4307-4314.

Odian, G. Principles of polymerization. John Wiley & Sons; 2004.

Salter, M. M., et al. Characterization of endothelial colony-forming cells from peripheral blood samples of adult horses. *American Journal of Veterinary Research* 2015; 76(2):174-187.

Van Den Bulcke, A. I., et al. Structural and rheological properties of methacrylamide modified gelatin hydrogels. *Biomacromolecules* 2000; 1(1):31-38.

Velasco, D., Tumarkin, E. and Kumacheva, E. Microfluidic Encapsulation of Cells in Polymer Microgels. *Small* 2012; 8(11): 1633-1642.

Example 2

Encapsulation of Equine ECFCs in Uniform, Injectable Hydrogel Microspheres for Local In Vivo Cell Delivery The importance of cell-based therapies such as endothelial colony forming cells (ECFCs) for treating ischemic disease has been increasingly recognized due to studies showing improved outcome (1-3). ECFCs, a subtype of endothelial progenitor cells (EPCs), directly participate in new blood vessel formation (4). Despite the promising results of many in vitro studies, the outcome of the cell-based therapies in vivo is often unconvincing. This is largely associated with the use of a direct cell injection method which causes insignificant cell accumulation or low retention at the targeted injection site (5, 6). Studies have shown that as few as 1% of the injected cells are retained after direct cell injection, with typical retention being less than 10% (7-11). In addition, exposure to ischemia and inflammation also compromises the function and fate of the injected cells (12-14).

Encapsulation of stem or progenitor cells in hydrogels has been shown to support cell proliferation and long-term survival (15). In addition, hydrogels can act as semi-permeable media to protect the transplanted or delivered cells from the host immune system (16). Cell retention at the desired location can be significantly improved by encapsulating cells in a hydrogel matrix prior to delivery (17). Therefore, cell encapsulation in hydrogel scaffolds could advance the potential of cell-based therapies.

The natural-synthetic hybrid hydrogel poly(ethylene glycol) (PEG)-fibrinogen (PF) has been shown to support a range of tissue engineering applications (18-22), including angiogenesis. While the acrylated-PEG enables rapid formation of a supportive structure through photocrosslinking, the fibrinogen provides adhesive anchorage and degradability for cellular activity. A wide variety of cell types including SMC, induced pluripotent stem cells, and chondrocytes have been encapsulated in PF with minimal impact in cell viability (23-27). Furthermore, injection of cells encapsulated within PF has been shown to enhance cell survival and differentiation compared to injection of cells suspended in aqueous saline solution (28), making PF a suitable biomaterial for cell delivery.

Encapsulation of cells into hydrogel microspheres increases the flexibility use of resulting engineered tissues for clinical applications, because of the ability to deliver microspheres by injection. However, typical cell encapsulation in microspheres using microfluidic devices is limited by low cell density which makes delivery of sufficient cell numbers in reasonable volumes for therapeutic applications challenging (16).

In this Example, encapsulation of ECFCs in PF hydrogel microspheres is accomplished at a high concentration of 10 million cells/mL using a custom-built microfluidic device. The microspheres are highly uniform in shape and size. The encapsulated ECFCs were shown to have high viability post-encapsulation and their phenotype was preserved compared to cells in typical cell culture conditions. As a proof of concept for utilizing microspheres produced by the microfluidic device as clinical cell delivery vehicles, an in vivo cell delivery study was also performed by encapsulating and injecting autologous equine ECFCs into a distal limb wound model in adult horses. The outcome of this study was demonstration of a cell encapsulation platform and examination of its potential for supporting therapeutic cell delivery by injection.

An equine wound model was used in this Example to study in vivo cell delivery. This is the first study to use PF hydrogels for cell delivery/tissue healing/regenerative studies in veterinary medicine. These horses were part of a larger, ongoing study on wound healing, first step of which was to confirm that cells were delivered and retained at the site of interest as reported here. Full thickness skin wounds of the distal limb that heal by second intention are common injuries in horses, and delayed healing and formation of exuberant granulation tissue (EGT) are frequent complications. At the time of the wound, cutaneous blood flow is disrupted, leading to altered tissue perfusion and reduced oxygen delivery. The decrease in blood flow is more pronounced and longer in duration in equine distal limb wounds than in body wall wounds (37). The extent and duration of loss of blood supply after the initial wound may determine the amount of hypoxia and tissue inflammation that leads to formation of EGT rather than normal healing. Although once EGT forms it is highly vascular, not all of the blood vessels that form are equally functional, and many occluded microvessels have been identified in leg wounds with EGT (35). Ideally a healing wound regains vascular supply as soon as possible and the vessels that form need to be functional so that local hypoxia and subsequent inflammation do not occur.

Promoting rapid vascularization is one of the biggest challenges in using engineered tissues for enhancing wound healing and treating disease. While ECFCs, or late EPCs, have been described as the only subtype of EPC that is responsible in building vessels, evidence have also shown that early EPCs promote angiogenesis through a paracrine mechanism (4). Recent studies have also suggested that adult stem cell therapy provides the majority of benefits through paracrine effects rather than direct tissue replacement (53, 54). The presented method of combining ECFCs with engineered biomaterials allows the direct delivery and retention of ECFCs, as well as the appropriate growth factors and signaling molecules needed, in the area of interest.

Encapsulation of ECFCs in PF hydrogels has strong potential in tissue engineering and clinical applications. PF was developed to create a controllable, degradable, and biofunctional 3D scaffold for cell culture (26). While PEG provides high biocompatibility and versatile physical structure, fibrinogen provides biological functionality including protease degradation capability (55) and cell-adhesion motifs (56). The studies described below are the first to encapsulate autologous ECFCs in PF and demonstrate the support of ECFC survival, maintenance of phenotype and outgrowth for use in injectable cell therapy for tissue regeneration applications.

Methods for this Example

Equine cell isolation and culture: All procedures involving animals were approved by the Auburn University Animal Care and Use Committee. Isolation and culture of equine endothelial colony forming cells (ECFCs) from equine peripheral blood were performed based on a previously published method (29). ECFCs were cultured in Endothelial Cell Basal Medium-2 (Lonza) containing 10% horse serum (HyClone) and SingleQuots Kit (Lonza) at 37° C. and 5% $CO_2$. The SingleQuots Kit contained hydrocortisone, hFGF-VEGF, R3-IGF-1, ascorbic acid, hEGF, GA-1,000, and heparin. The ECFCs were seeded and expanded on collagen coated tissue culture polystyrene flasks. When ECFCs reached 90% confluency, cells were subcultured using trypsin/EDTA (Lonza) to detach the cells at 37° C. for 50 s, followed by neutralization with fresh medium and centrifugation at 200 g for 5 min. ECFCs were resuspended in medium and then subcultured at a ratio of 1:6 or immediately used for experiments. Cells between passage 2-7 were used for all experiments.

PEGDA and PEG-Fibrinogen Synthesis:

PEG-diacrylate (PEGDA) and PEG-Fibrinogen (PF) were synthesized as outlined in the methods section of Example 1.

Cell Encapsulation in PEG-Fibrinogen Microspheres and Cell Viability Assay:

Cell encapsulation in PF microspheres was performed as outlined in the methods section of Example 1. A schematic of the process is shown again as FIG. 16A. After encapsulation, cell viability was assessed using the Live/Dead viability/cytotoxicity kit (Invitrogen) as described in Example 1. After passage through a syringe, cell viability was assessed using XTT Cell Viability Assay Kit (Biotium) as described in Example 1.

Characterization of Microsphere Geometry and Stiffness:

Microsphere geometry and stiffness were characterized as outlined in Example 1.

Outgrowth Cells Phenotypic Characterization:

To assess the phenotype of the encapsulated cells, microspheres were cultured on collagen coated well-plates, and cells growing out from microspheres onto the well-plate were harvested and sub-cultured once to obtain sufficient cells for characterization. In order to ensure the ECFC phenotype was not impacted by the number of subcultures, ECFCs that had the same passage number in culture but did not go through encapsulation were used for comparison.

Uptake of DiI-Ac-LDL:

The ability of ECFCs to take up 1,1'-Dioctadecyl-3,3,3',3'-tetramethylindocarbocyanine perchlorate-labeled acetylated low density lipoprotein (DiI-Ac-LDL) was evaluated. 10 µg/mL of DiI-Ac-LDL (Biomedical Technologies) in pre-warmed medium was added to the ECFCs followed by incubation for 6 hours at 37° C. and 5% $CO_2$. After incubation, uptake of DiI-Ac-LDL by ECFCs was imaged using fluorescent microscopy.

In Vitro Tubule Formation Assay:

ECFCs were seeded onto a 96-well plate (30,000 cells/well) containing Matrigel (Corning, 50 μL/well), which had been incubated for 15 min before cell seeding. Tubule formation was assessed after 5 hours of incubation at 37° C. and 5% $CO_2$ by light microscopy.

Immunofluorescence Analysis:

Equine ECFCs pre- and post-encapsulation were evaluated for the expression of cell markers von Willebrand Factor (vWF), CD14, and CD105 with indirect immunofluorescence assay (IFA) as previously published (32). ECFCs were fixed with 4% paraformaldehyde (PFA) solution and rinsed with PBS solution. For analysis of expression of the intracellular protein vWF, ECFCs were permeabilized with PBS-T containing 0.2% Triton X 100 (Sigma) in PBS for 30 minutes, and then blocked with 3% horse serum at 4° C. overnight. The fixed cells were then incubated at room temperature for 1 hour with primary antibodies diluted in 3% horse serum as follows: rabbit anti-human vWF (Dako) at 1:100, mouse anti-horse CD14 at 1:200 (Wagner Laboratory, Cornell University, (33)), mouse anti-human CD105 at 1:200 (AbD Serotec). After incubation, cells were washed with PBS-T before the application of secondary antibodies. Secondary antibodies were diluted in 3% horse serum and incubated with cells at room temperature in the dark for 1 hour as follows: Alexa Fluor 488-conjugated goat anti-rabbit IgG at 1:400 for vWF and Alexa Fluor 488-conjugated goat anti-mouse IgG at 1:400 for CD14 and CD105. Cells were counter stained with DAPI, washed with PBS, mounted on glass slides with ProLong Gold antifade reagent (Life Technologies), and imaged with fluorescent microscopy.

Flow Cytometry:

To assess the influence of the encapsulation process on ECFC phenotype, flow cytometry was used to quantify expression of vWF, CD14, CD105, and uptake of DiI-Ac-LDL. For DiI-Ac-LDL uptake, cells were incubated with medium containing 10 μg/mL of DiI-Ac-LDL at 37° C. for 6 hours. After incubation, cells were rinsed with medium and PBS, detached, centrifuged, and fixed in suspension with 4% PFA for 20 min at room temperature, followed by a rinse with PBS. The cells were then stored in 3% horse serum in PBS.

For vWF staining, detached cells were fixed, permeabilized, and blocked with 10% horse serum at 4° C. overnight. Then cells were incubated with primary antibodies at room temperature for 1 hour, rinsed with blocking solution, and incubated in secondary antibodies at room temperature for 1 hour in the dark. For CD14 and CD105 staining, detached cells were incubated with primary antibodies at 4° C. for 1 hour, rinsed with blocking solution, incubated in secondary antibodies at room temperature for 1 hour in the dark, rinsed with blocking solution, and then fixed. The same concentrations of the primary and secondary antibodies were used as for IFA. Cells that were incubated with the secondary antibody only were used to measure the background staining. Cells were resuspended in 3% horse serum in PBS and filtered using Flowmi tip strainers (Bel-Art) before flow analysis. A total of 10,000 events were collected for each sample which were analyzed using a BD Accuri C6 flow cytometer (BD Biosciences).

Cell Viability after Injection Through a Syringe and Needle:

To further assess the potential of the microspheres as vehicles for injectable cell delivery, the effect of shear stress during injection on cell viability was studied. Microspheres were suspended in cold equine serum, with a viscosity of 1.909 centiPoise at 14° C., loaded into 1 mL Luer lock syringes, and sheared through 18 gauge, 20 gauge, and 23 gauge needles respectively at 1 mL/min (34). The XTT Cell Viability Assay Kit (Biotium) was then used to evaluate cell viability and proliferation. Following the injection simulation, microspheres containing ECFCs were aliquoted into a 96-well-plate with one microsphere per well. 100 μl of pre-warmed medium and 25 μl of XTT working solution were then added to each well. After incubation for 18 hours at 37° C., absorbance signal of the sample was measured with a microplate reader (BioTek). Four separate trials were performed; viability was assessed for five microspheres per condition per trial and data for each trial normalized with respect to control optical density.

Ex Vivo Cell Delivery and Survival of Encapsulated ECFCs:

A cadaver limb from an adult horse collected immediately after euthanasia was used to evaluate cell delivery ex vivo. The hair of the dorsomedial aspect of the metacarpus was clipped and two 6.25 $cm^2$ square, full-thickness wounds were created using a surgical template. Trypan blue stained PEGDA microspheres in saline or ECFCs encapsulated into PF microspheres in serum were injected (600 μL) subcutaneously at the wound edge. Injections were made through an 18-gauge x 1" needle on a 1 mL luer lock syringe. Trypan blue stained PEGDA microspheres were directly visualized. A full thickness section of skin and subcutaneous tissue surrounding the area of injection was removed using a scalpel blade and placed in cell culture media and incubated over night at 37° C. Subcutaneous tissue was bluntly dissected at 24 hours and visualized with fluorescent and phase contrast microscopy.

In Vivo Injection and Cell Tracking of Autologous ECFCs Encapsulated in PF Microspheres:

A timeline of the in vivo study is shown in FIG. 16B. Three, adult horses were used to evaluate delivery of encapsulated, autologous ECFCs labeled with Qtracker 655 (Invitrogen) to full thickness wounds created on the distal limb. Autologous ECFCs were labeled with 4 microMolar Qtracker 655 according to the manufacturer's instructions prior to encapsulation. The equine distal limb wound model was created in a similar manner to previous studies (35-37). Horses were kept free in individual box stalls for the duration of the study and allowed ad libitum access to grass hay and water. For the surgical procedure, analgesia and sedation were provided with detomidine hydrochloride (0.01 mg/kg; IV) and butorphanol tartrate (0.04 mg/kg; IV), and local anesthesia was performed using 2% mepivacaine hydrochloride. The surgical sites were clipped and aseptically prepared, and two 6.25 $cm^2$ square, full thickness wounds were created on the dorsal aspect of each metacarpus and metatarsus using a sterile wound template and a #15 scalpel blade. 24 hours after surgery, the edges of 2 wounds per horse were injected subcutaneously using 18 gauge 1" needles on 1 mL luer lock syringes with autologous ECFCs encapsulated in PF microspheres diluted into equine serum (600 microliters). Each injection of cell-laden microspheres contained approximately $2 \times 10^6$ ECFCs in PF microspheres. All 4 edges of the wound were injected for a total of $8 \times 10^6$ ECFCs in PF microspheres per wound. As the wound model was also being utilized for a larger, ongoing treatment trial with ECFCs, the remaining wounds were treated in duplicate with autologous ECFCs ($2 \times 10^6$), PF microspheres, and equine serum only and evaluated weekly until complete healing (approximately 6 weeks). One week after injection, the horses were sedated, local anesthesia performed, and then the lateral leading edge of each was biopsied using a 6 mm punch biopsy instrument. One biopsy sample was placed in OCT freezing media and snap frozen in liquid $N_2$ cooled isopentane and the other sample was formalin fixed and paraffin embedded for immunohistochemical analysis as part of the wound healing study. Frozen tissues were cryo-sectioned (20 micrometers), placed on glass slides, fixed in 4% PFA, stained with DAPI, and imaged with confocal microscopy.

Statistical Analysis:

Data are represented as means±SD. All statistical analysis was performed using Minitab 17 Statistical Software (Minitab Inc.). After verifying equal variances using the F-test, the Student's t-test was used for comparisons between two groups. After checking for normality of distribution, one-way ANOVA followed by the Tukey-Kramer HSD test for multiple comparisons was used to evaluate statistical significance between multiple groups. Unless otherwise indicated, $p<0.05$ was considered statistically significant.

Results for this Example

High Cell Viability and Uniform Microsphere Geometry Post-Encapsulation:

Microspheres formed using the custom built PDMS molded microfluidic device were highly uniform and provided a suitable microenvironment for cell proliferation and survival. Following microsphere encapsulation, ECFC viability was very high (96.8±1.4%) as shown in FIGS. 17A-17D. The microspheres produced were highly uniform in both size and roundness. The diameters were 598±45 μm on Day 1 and 584±22 μm on Day 3; while the roundness was 0.95±0.001 on Day 1 and 0.91±0.001 on Day 3 as shown in FIGS. 17E-17H.

Figure 17:
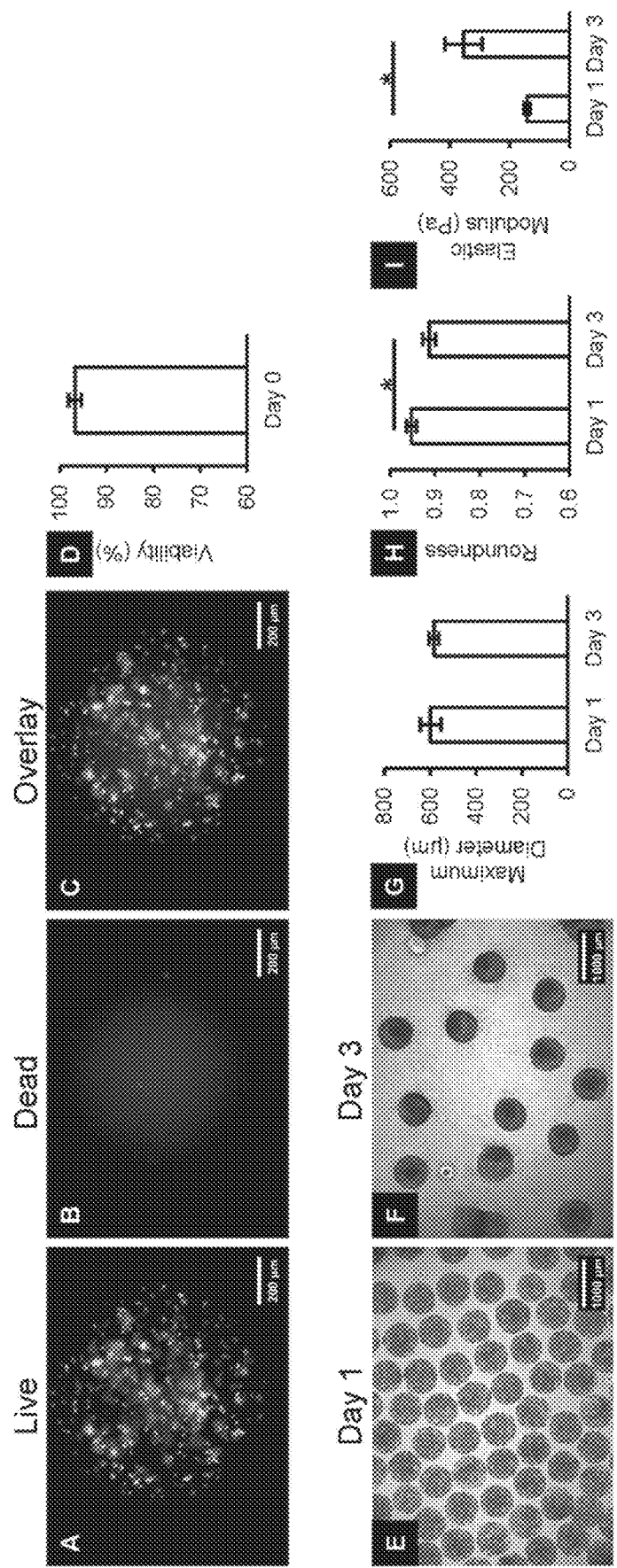
(FIGS. 17A-17D) Immediately post encapsulation (Day 0), ECFC viability was 96.8% as quantified using Live (green)/Dead (red) staining (n=3 separate encapsulations with >3 microspheres evaluated per encapsulation).
(FIG. 17E and FIG. 17F) Phase contrast images showing ECFC encapsulated microspheres on Day 1 and Day 3. Similar maximum diameter (FIG. 17G) and high roundness (FIG. 17H) of the microspheres on Day 1 and Day 3 (n=3 separate encapsulations with 30-100 microspheres evaluated per encapsulation). Roundness significantly decreased by Day 3 (p<0.05).
(FIG. 17I) Elastic modulus of microspheres significantly increased from Day 1 to Day 3 (p<0.01, n=4 microspheres per condition).

Increased Elastic Modulus and Outgrowth from Microspheres Indicating Cell Proliferation Post-Encapsulation in PEG Fibrinogen Microspheres:

The stiffness of the microspheres was assessed in terms of elastic modulus. The elastic modulus of the microspheres with encapsulated ECFCs increased significantly from 141±10 Pa on Day 1 to 354±62 Pa on Day 3 (FIG. 17I). This increase in modulus correlated with a visual increase in total cell number and re-organization of the ECFCs within the microspheres (FIG. 17F, FIGS. 18A-18C).

Figure 18:
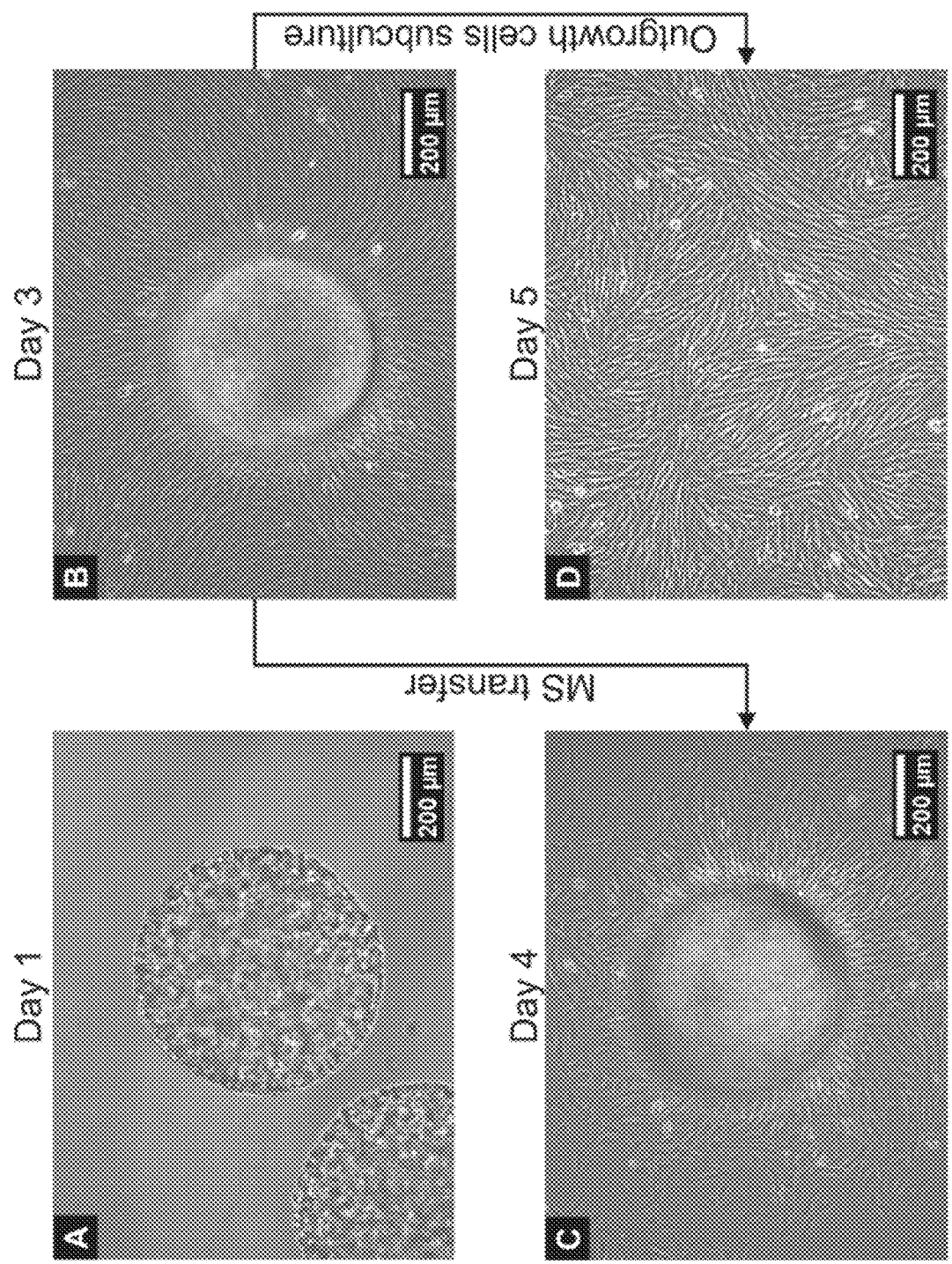
FIGS. 18A-18D. Phase contrast images showing ECFC migration and proliferation phenotypes were maintained post encapsulation.

In addition to maintaining a high level of viability, the ECFCs also remained highly proliferative post-encapsulation. On Day 1, the encapsulated ECFCs were observed to align and cover the surface of the microspheres (FIG. 18A). As ECFCs continued to remodel the microspheres, a confluent monolayer of ECFCs was observed on the bottom of the well plate by Day 3 indicating active cell migration and proliferation (FIG. 18B). After the ECFCs and microspheres were trypsinized and transferred to a new well plate, ECFCs were again observed on the bottom of the well plate around the re-plated microspheres after just one day (FIG. 18C). In addition, the confluent monolayer of outgrowth ECFCs observed on Day 3 was passaged, and the passaged outgrowth ECFCs again formed a confluent monolayer at an equivalent rate to encapsulated control ECFCs, indicating that the ECFCs maintained their highly proliferative nature following microsphere encapsulation of the ECFCs (FIG. 18D).

Figure 19:
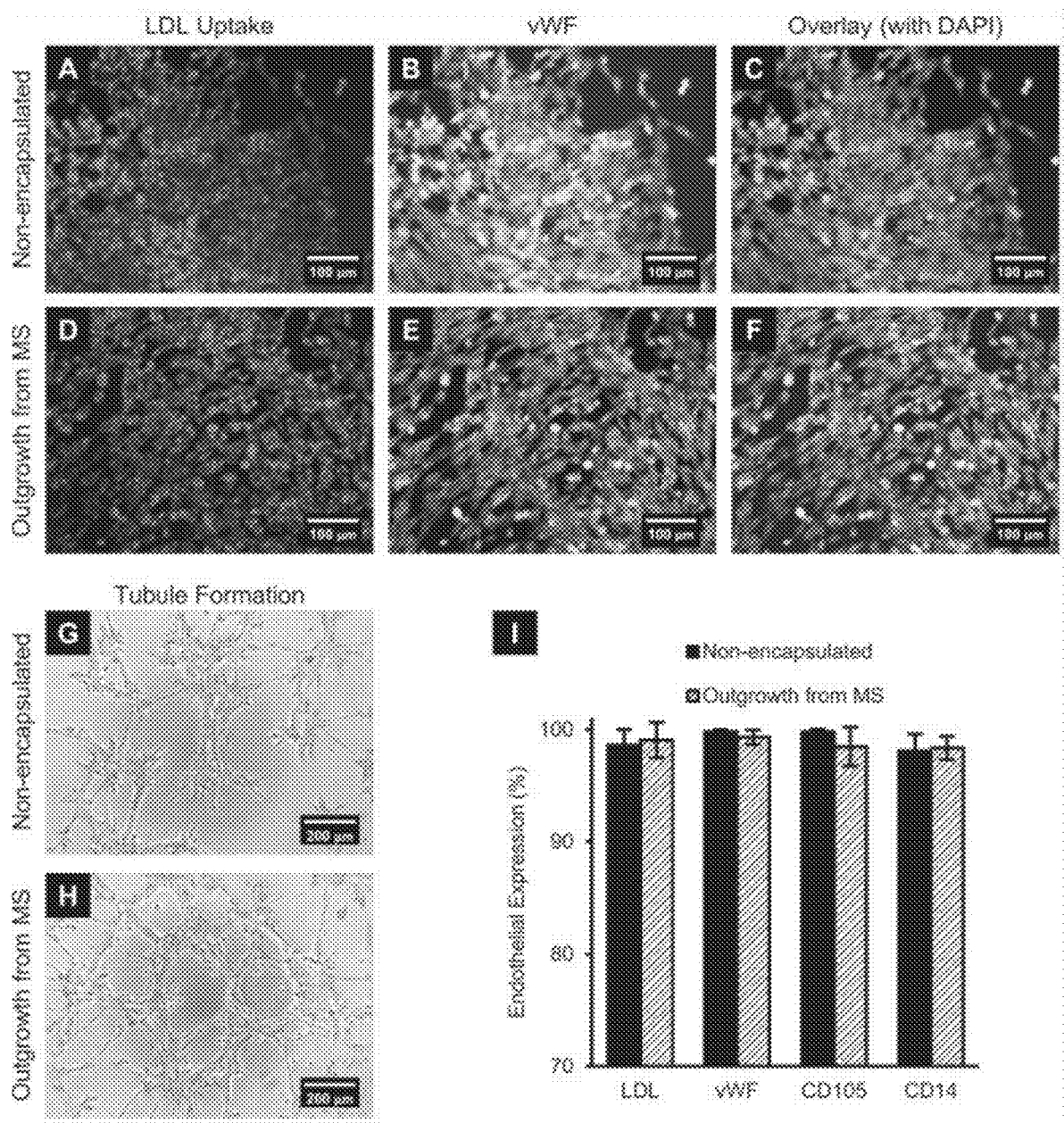
FIGS. 19A-19I. ECFCs maintained their endothelial phenotype alter encapsulation and culture in PF microspheres. Outgrowth ECFCs from microspheres showed similar endothelial phenotype as compared to nonencapsulated ECFCs in terms of Dil-Ac-LDL uptake, vWF expression (FIGS. 19A-19F), and tubule formation (FIG. 19G and FIG. 19H).

Outgrowth ECFCs Maintain their Phenotype:

ECFCs have the same phenotypic characteristics pre- and post-encapsulation. Both outgrowth ECFCs and non-encapsulated ECFCs (only cultured on tissue culture polystyrene (TCPS) flasks) were able to form tubular networks on Matrigel, take up DiI-Ac-LDL, and express vWF as shown in FIG. 19A-19H. Endothelial function and expression of markers previously used to characterize equine ECFCs (32) were evaluated quantitatively in both groups of ECFCs using flow cytometry. For ECFCs that were only cultured on TCPS flasks (non-encapsulated), 98.6±1.4% of cells demonstrated uptake of DiI-Ac-LDL, 99.8±0.2% of cells expressed vWF, 99.8±0.2% expressed CD105, and 98.1±1.5% expressed CD14 (FIG. 19I). In outgrowth ECFCs from the microspheres, 99.0±1.6% of cells demonstrated uptake of DiI-Ac-LDL, 99.3±0.6% of cells expressed vWF, 98.5±1.7% expressed CD105, and 98.4±1.0% expressed CD14 (FIG. 19I). No significant differences were found between the two groups.

Figure 20:
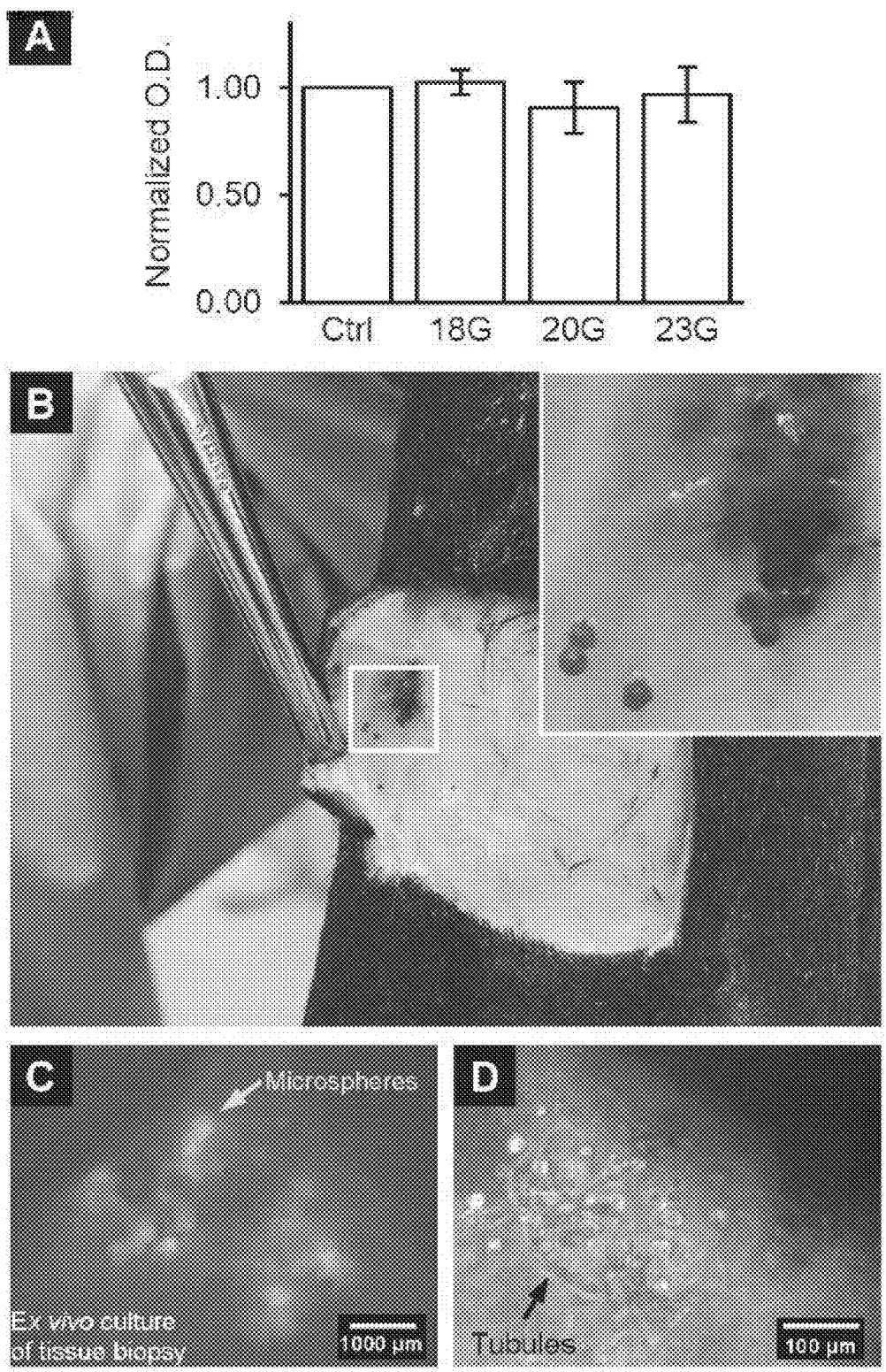
FIGS. 20A-20D. Injected microspheres supported cell delivery.

Microspheres are Retained and Encapsulated Cells are Viable in Tissue after Subcutaneous Injection and Shear Through Different Gauge Needles:

To evaluate the potential of using hydrogel microspheres for cell injection therapy, the retention of microspheres in tissue and the viability of encapsulated ECFCs after shear through different needle gauges was examined ex vivo. There was no statistical difference in viability of encapsulated ECFCs as quantified by XTT assay after shear through 18, 20, and 23 gauge needles (FIG. 20A). Cell-free microspheres that were created with PEGDA and stained with trypan blue were injected subcutaneously into the edge of a wound created on an equine cadaver limb using 18 gauge 1" needles. The injected microspheres remained in the subcutaneous tissue at the wound edge without any visually obvious breakdown or deformation of the microspheres (FIG. 20B).

An ex vivo experiment was then performed to evaluate viability and migration from the microspheres of the encapsulated cells when injected into and surrounded by host tissue. After one day of ex vivo culture at 37° C., subcutaneously injected microspheres remained present as a group within the tissue as indicated by the green autofluorescence of eosin Y (FIG. 20C). Furthermore, encapsulated ECFCs became elongated and formed tubules along the surface of the microspheres (FIG. 20D). This observation was similar compared to the in vitro study shown in FIGS. 18A-18D.

Figure 21:
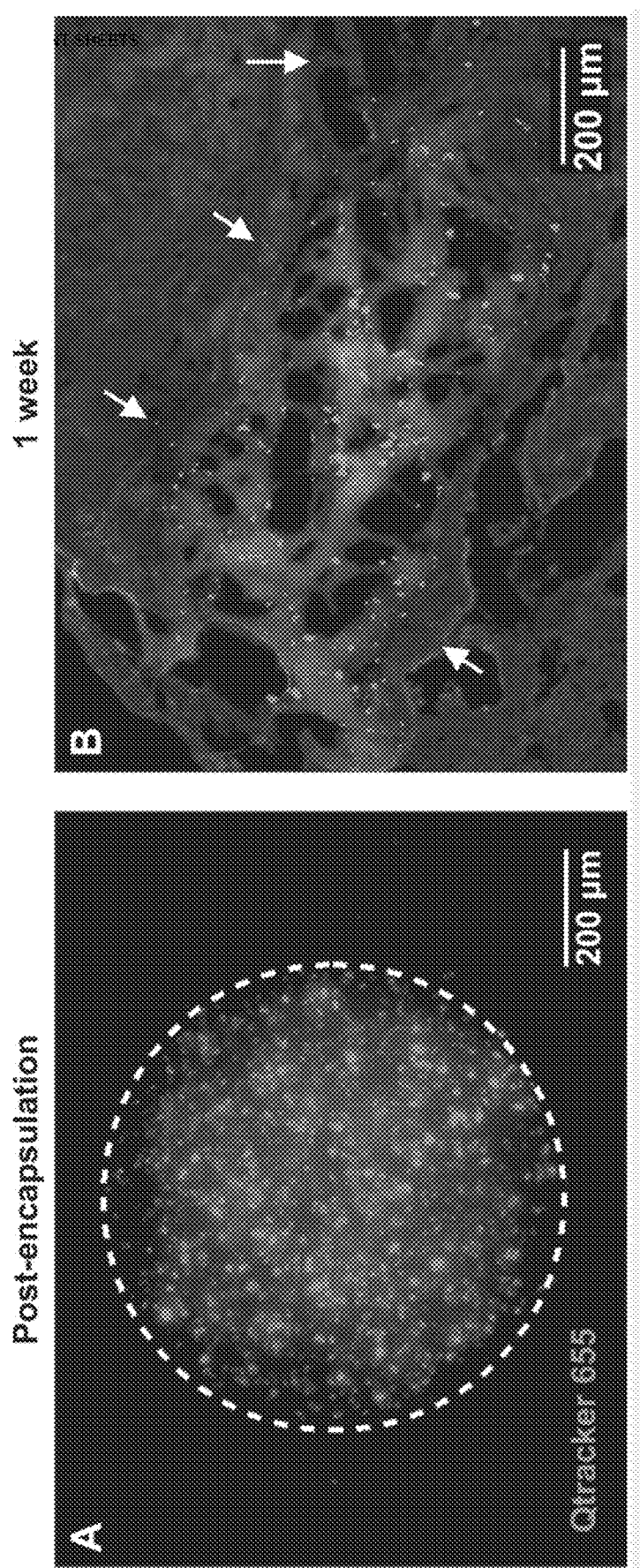
FIGS. 21A-21B. Q-tracker labeled ECFCs remained visible for cell tracking post-encapsulation and 1 week after in vivo injection.

PEG Fibrinogen Encapsulated ECFCs are Retained at the Injection Site and Beginning to Migrate Out of PF 7 Days after In Vivo Subcutaneous Injection:

An in vivo study was performed in 3 horses to evaluate cell retention and outgrowth of the encapsulated ECFCs to the surrounding host tissue. Autologous ECFCs were labeled with Q-tracker 655 (red, FIG. 21A) and then encapsulated at a concentration of 10 million cells per mL of PF precursor solution to achieve the desired dose of 2 million cells for each injection. For each horse, ECFCs were encapsulated for 4 injections per wound with two wounds per animal plus an in vitro control, meaning that 24 million cells were encapsulated. After microfluidic system setup, encapsulation took approximately 12 minutes per 2 million cell injection.

Following rinsing and resuspension, cell-laden microspheres were injected into the edges of distal limb wounds in 3 adult horses. One week post-injection of the microspheres into the edge of a wound, the Q-tracker labeled ECFCs (red) were identified in the biopsy of all 3 horses as shown in a representative biopsy sample in FIG. 21B. The injected microspheres were still present in 1 horse as shown by the green autofluorescence. There was evidence of migration of some ECFCs from the microspheres to the surrounding host tissue suggesting viable cells as indicated by the white arrows. The PF encapsulated ECFCs were verified to be retained at the injection site and demonstrating outgrowth 1 week after subcutaneous injection.

REFERENCES CITED IN THIS EXAMPLE

1. Perin, E. C., Assad, J. A., Silva, G. V., Coulter, S., Ober, J., Lin, J., Sousa, A. L., Litowski, S., Geng, Y., Martin, B. J., Vaughn, W. K., and Willerson, J. T. Comparison between intracoronary infusion and direct transendocardial injection of mesenchymal stem cells in a dog acute ischemia model. *Journal of the American College of Cardiology* 43, 63A, 2004.
2. Wang, C. C., Chen, C. H., Lin, W. W., Hwang, S. M., Hsieh, P. C. H., Lai, P. H., Yeh, Y. C., Chang, Y., and Sung, H. W. Direct intramyocardial injection of mesenchymal stem cell sheet fragments improves cardiac functions after infarction. Cardiovascular Research 77, 515, 2008.
3. Chin, S. P., Poey, A. E., Chang, S. K., Wong, C. Y., Lam, K. H., and Cheong, S. K. Safety and efficacy of autologous mesenchymal stem cells for the treatment of end-stage dilated cardiomyopathy—a comparison of intracoronary and direct intramyocardial injection. European Heart Journal 31, 79, 2010.
4. Medina, R. J., Barber, C. L., Sabatier, F., Dignat-George, F., Melero-Martin, J. M., Khosrotehrani, K., Ohneda, O., Randi, A. M., Chan, J. K., Yamaguchi, T., Van Hinsbergh, V. W., Yoder, M. C., and Stitt, A. W. Endothelial Progenitors: A Consensus Statement on Nomenclature. Stem cells translational medicine 62017.
5. Qian, H., Yang, Y., Huang, J., Gao, R., Dou, K., Yang, G., Li, J., Shen, R., He, Z., Lu, M., andZha, S. Intracoronary delivery of autologous bone marrow mononuclear cells radiolabeled by 18F-fluoro-deoxy-glucose: Tissue distribution and impact on post-infarct swine hearts. *Journal of Cellular Biochemistry* 102, 64, 2007.
6. Gaffey, A. C., Chen, M. H., Venkataraman, C. M., Trubelja, A., Rodell, C. B., Dinh, P. V., Hung, G., MacArthur, J. W., Soopan, R. V., and Burdick, J. A. Injectable shear-thinning hydrogels used to deliver endothelial progenitor cells, enhance cell engraftment, and improve ischemic myocardium. The *Journal of thoracic and cardiovascular surgery* 150, 1268, 2015.
7. Sheikh, A. Y., Huber, B. C., Narsinh, K. H., Spin, J. M., van der Bogt, K., de Almeida, P. E., Ransohoff, K. J., Kraft, D. L., Fajardo, G., Ardigo, D., Ransohoff, J., Bernstein, D., Fischbein, M. P., Robbins, R. C., and Wu, J. C. In Vivo Functional and Transcriptional Profiling of Bone Marrow Stem Cells After Transplantation Into Ischemic Myocardium. Arteriosclerosis Thrombosis and Vascular Biology 32, 92, 2012.
8. Hofmann, M., Wollert, K. C., Meyer, G. P., Menke, A., Arseniev, L., Hertenstein, B., Ganser, A., Knapp, W. H., and Drexler, H. Monitoring of bone marrow cell homing into the infarcted human myocardium. Circulation 111, 2198, 2005.
9. Schaechinger, V., Aicher, A., Doebert, N., Roever, R., Diener, J., Fichtlscherer, S., Assmus, B., Seeger, F. H., Menzel, C., Brenner, W., Dimmeler, S., and Zeiher, A. M. Pilot trial on determinants of progenitor cell recruitment to the infarcted human myocardium. Circulation 118, 1425, 2008.
10. Li, S. H., Lai, T. Y. Y., Sun, Z., Han, M., Moriyama, E., Wilson, B., Fazel, S., Weisel, R. D., Yau, T., Wu, J. C., and Li, R. K. Tracking cardiac engraftment and distribution of implanted bone marrow cells: Comparing intra-aortic, intravenous, and intramyocardial delivery. *Journal of Thoracic and Cardiovascular Surgery* 137, 1225, 2009.
11. Dow, J., Simkhovich, B. Z., Kedes, L., and Kloner, R. A. Washout of transplanted cells from the heart: A potential new hurdle for cell transplantation therapy. Cardiovascular Research 67, 301, 2005.
12. Wang, H., Zhou, J., Liu, Z., and Wang, C. Injectable cardiac tissue engineering for the treatment of myocardial infarction. *Journal of Cellular and Molecular Medicine* 14, 1044, 2010.
13. Laflamme, M. A., Chen, K. Y., Naumova, A. V., Muskheli, V., Fugate, J. A., Dupras, S. K., Reinecke, H., Xu, C., Hassanipour, M., Police, S., O'Sullivan, C., Collins, L., Chen, Y., Minami, E., Gill, E. A., Ueno, S., Yuan, C., Gold, J., and Murry, C. E. Cardiomyocytes derived from human embryonic stem cells in pro-survival factors enhance function of infarcted rat hearts. Nature Biotechnology 25, 1015, 2007.
14. Robey, T. E., Saiget, M. K., Reinecke, H., and Murry, C. E. Systems approaches to preventing transplanted cell death in cardiac repair. *Journal of Molecular and Cellular Cardiology* 45, 567, 2008.
15. Rafii, S., and Lyden, D. Therapeutic stem and progenitor cell transplantation for organ vascularization and regeneration. Nature Medicine 9, 702, 2003.
16. Velasco, D., Tumarkin, E., and Kumacheva, E. Microfluidic Encapsulation of Cells in Polymer Microgels. Small 8, 1633, 2012.
17. Bidarra, S. J., Barrias, C. C., and Granj a, P. L. Injectable alginate hydrogels for cell delivery in tissue engineering. *Acta* Biomaterialia 10, 1646, 2014.
18. Lu, Q. Q., Pandy a, M., Rufaihah, A. J., Rosa, V., Tong, H. J., Seliktar, D., and Toh, W. S. Modulation of Dental Pulp Stem Cell Odontogenesis in a Tunable PEG-Fibrinogen Hydrogel System. Stem Cells International 2015.
19. Fuoco, C., Salvatori, M. L., Biondo, A., Shapira-Schweitzer, K., Santoleri, S., Antonini, S., Bernardini, S., Tedesco, F. S., Cannata, S., Seliktar, D., Cossu, G., and Gargioli, C. Injectable polyethylene glycol-fibrinogen hydrogel adjuvant improves survival and differentiation of transplanted mesoangioblasts in acute and chronic skeletal-muscle degeneration. Skelet Muscle 2, 24, 2012.
20. Peled, E., Boss, J., Bejar, J., Zinman, C., and Seliktar, D. A novel poly(ethylene glycol)-fibrinogen hydrogel for tibial segmental defect repair in a rat model. J *Biomed Mater* Res A 80, 874, 2007.
21. Pradhan, S., Clary, J. M., Seliktar, D., and Lipke, E. A. A three-dimensional spheroidal cancer model based on PEG-fibrinogen hydrogel microspheres. Biomaterials 115, 141, 2017.
22. Kerscher, P., Turnbull, I. C., Hodge, A. J., Kim, J., Seliktar, D., Easley, C. J., Costa, K. D., and Lipke, E. A. Direct hydrogel encapsulation of pluripotent stem cells enables ontomimetic differentiation and growth of engineered human heart tissues. Biomaterials 83, 383, 2016.
23. Peyton, S. R., Kim, P. D., Ghajar, C. M., Seliktar, D., and Putnam, A. J. The effects of matrix stiffness and RhoA on the phenotypic plasticity of smooth muscle cells in a 3-D biosynthetic hydrogel system. Biomaterials 29, 2597, 2008.
24. Bearzi, C., Gargioli, C., Baci, D., Fortunato, O., Shapira-Schweitzer, K., Kossover, O., Latronico, M. V., Seliktar, D., Condorelli, G., and Rizzi, R. PlGF-MMP9-engineered iPS cells supported on a PEG-fibrinogen hydrogel scaffold possess an enhanced capacity to repair damaged myocardium. Cell Death Dis 5, e1053, 2014.
25. Appelman, T. P., Mizrahi, J., Elisseeff, J. H., and Seliktar, D. The influence of biological motifs and dynamic 25. mechanical stimulation in hydrogel scaffold systems on the phenotype of chondrocytes. Biomaterials 32, 1508, 2011.
26. Almany, L., and Seliktar, D. Biosynthetic hydrogel scaffolds made from fibrinogen and polyethylene glycol for 3D cell cultures. Biomaterials 26, 2467, 2005.
27. Frisman, I., Seliktar, D., and Bianco-Peled, H. Nanostructuring biosynthetic hydrogels for tissue engineering: a cellular and structural analysis. Acta Biomater 8, 51, 2012.
28. Fuoco, C., Cannata, S., Bottinelli, R., Seliktar, D., Cossu, G., and Gargioli, C. Autologous progenitor cells in a hydrogel form a supernumerary and functional skeletal muscle in vivo. *Journal of Tissue Engineering and Regenerative Medicine* 6, 116, 2012.
29. Sharpe, A. N., Seeto, W. J., Winter, R. L., Zhong, Q., Lipke, E. A., and Wooldridge, A. A. Isolation of endothelial colony-forming cells from blood samples collected from the jugular and cephalic veins of healthy adult horses. *American journal of veterinary research* 77, 1157, 2016.
30. Stroncek, J. D., Grant, B. S., Brown, M. A., Povsic, T. J., Truskey, G. A., and Reichert, W. M. Comparison of Endothelial Cell Phenotypic Markers of Late-Outgrowth Endothelial Progenitor Cells Isolated from Patients with Coronary Artery Disease and Healthy Volunteers. Tissue Engineering Part A 15, 3473, 2009.
31. Franco, C. L., Price, J., and West, J. L. Development and optimization of a dual-photoinitiator, emulsion-based technique for rapid generation of cell-laden hydrogel microspheres. *Acta Biomaterialia* 7, 3267, 2011.
32. Salter, M. M., Seeto, W. J., DeWitt, B. B., Hashimi, S. A., Schwartz, D. D., Lipke, E. A., andWooldridge, A. A. Characterization of endothelial colony-forming cells from peripheral blood samples of adult horses. *American Journal* of Veterinary Research 76, 174, 2015.
33. Kabithe, E., Hillegas, J., Stokol, T., Moore, J., and Wagner, B. Monoclonal antibodies to equine CD14. Vet Immunol Immunopathol 138, 149, 2010.
34. Aguado, B. A., Mulyasasmita, W., Su, J., Lampe, K. J., and Heilshorn, S. C. Improving Viability of Stem Cells During Syringe Needle Flow Through the Design of Hydrogel Cell Carriers. Tissue Engineering Part A 18, 806, 2012.
35. Celeste, C. J., Deschene, K., Riley, C. B., and Theoret, C. L. Regional differences in wound oxygenation during normal healing in an equine model of cutaneous fibroproliferative disorder. Wound Repair and Regeneration 19, 89, 2011.
36. Deschene, K., Celeste, C., Boerboom, D., and Theoret, C. L. Constitutive expression of hypoxia-inducible factor-1 alpha in keratinocytes during the repair of skin wounds in horses. Wound Repair and Regeneration 19, 250, 2011.
37. Celeste, C. J., Deschesne, K., Riley, C. B., and Theoret, C. L. Skin Temperature during Cutaneous Wound Healing in an Equine Model of Cutaneous Fibroproliferative Disorder: Kinetics and Anatomic-Site Differences. Veterinary Surgery 42, 147, 2013.
38. Rufaihah, A. J., and Seliktar, D. Hydrogels for therapeutic cardiovascular angiogenesis. *Advanced* Drug Delivery Reviews 96, 31, 2016.
39. Klouda, L. Thermoresponsive hydrogels in biomedical applications: A seven-year update. European *journal of pharmaceutics and biopharmaceutics: official journal of* Arbeitsgemeinschaft fur Pharmazeutische Verfahrenstechnik eV 97, 338, 2015.
40. Hacker, M. C., and Nawaz, H. A. Multi-Functional Macromers for Hydrogel Design in Biomedical Engineering and Regenerative Medicine. Int J Mol Sci 16, 27677, 2015.
41. Olabisi, R. M. Cell microencapsulation with synthetic polymers. *Journal of Biomedical Materials Research Part* a 103, 846, 2015.
42. Barron, C., and He, J. Q. Alginate-based microcapsules generated with the coaxial electrospray method for clinical application. J Biomater Sci Polym Ed, 1, 2017.
43. Jiang, W., Li, M., Chen, Z., and Leong, K. W. Cell-laden microfluidic microgels for tissue regeneration. Lab Chip 16, 4482, 2016.
44. Williams, C. G., Malik, A. N., Kim, T. K., Manson, P. N., and Elisseeff, J. H. Variable cytocompatibility of six cell lines with photoinitiators used for polymerizing hydrogels and cell encapsulation. Biomaterials 26, 1211, 2005.
45. Tumarkin, E., and Kumacheva, E. Microfluidic generation of microgels from synthetic and natural polymers. Chemical Society Reviews 38, 2161, 2009.
46. Ferris, D., Frisbie, D., Kisiday, J., and McIlwraith, C. W. In vivo healing of meniscal lacerations using bone marrow-derived mesenchymal stem cells and fibrin glue. Stem Cells Int 2012, 691605, 2012.
47. Youngstrom, D. W., Barrett, J. G., Jose, R. R., and Kaplan, D. L. Functional characterization of detergent-decellularized equine tendon extracellular matrix for tissue engineering applications. *PLoS One* 8, e64151, 2013.
48. Watts, A. E., Ackerman-Yost, J. C., and Nixon, A. J. A comparison of three-dimensional culture systems to evaluate in vitro chondrogenesis of equine bone marrow-derived mesenchymal stem cells. Tissue Eng Part A 19, 2275, 2013.
49. Drela, E., Stankowska, K., Kulwas, A., and Rosc, D. Endothelial Progenitor Cells in Diabetic Foot Syndrome. Advances in Clinical and Experimental Medicine 21, 249, 2012.
50. Asai, J., Takenaka, H., Ii, M., Asahi, M., Kishimoto, S., Katoh, N., and Losordo, D. W. Topical application of ex vivo expanded endothelial progenitor cells promotes vascularisation and wound healing in diabetic mice. International Wound Journal 10, 527, 2013.
51. Moon, J. J., Saik, J. E., Poche, R. A., Leslie-Barbick, J. E., Lee, S. H., Smith, A. A., Dickinson, M. E., and West, J. L. Biomimetic hydrogels with pro-angiogenic properties. Biomaterials 31, 3840, 2010.
52. Urbich, C., Aicher, A., Heeschen, C., Dembach, E., Hofmann, W. K., Zeiher, A. M., and Dimmeler, S. Soluble factors released by endothelial progenitor cells promote migration of endothelial cells and cardiac resident progenitor cells. *Journal of Molecular and Cellular Cardiology* 39, 733, 2005.
53. Luo, L., Tang, J., Nishi, K., Yan, C., Dinh, P. U., Cores, J., Kudo, T., Zhang, J., Li, T. S., and Cheng, K. Fabrication of Synthetic Mesenchymal Stem Cells for the Treatment of Acute Myocardial Infarction in Mice. Circulation Research 1202017.
54. Tang, J. A., Shen, D. L., Caranasos, T. G., Wang, Z. G., Vandergriff, A. C., Allen, T. A., Hensley, M. T., Dinh, P. U., Cores, J., Li, T. S., Zhang, J. Y., Kan, Q. C., and Cheng, K. Therapeutic microparticles functionalized with biomimetic cardiac stem cell membranes and secretome. Nature Communications 82017.
55. Werb, Z. ECM and cell surface proteolysis: Regulating cellular ecology. Cell 91, 439, 1997.
56. Herrick, S., Blanc-Brude, O., Gray, A., and Laurent, G. Fibrinogen. Int J Biochem Cell Biol 31, 741, 1999.

Example 3

Rapid Production of Engineered Cardiac Tissue Microspheres from Encapsulated Human Induced Pluripotent Stem Cells (hiPSCs)

Cardiovascular disease is the leading cause of death in the world due to the limited ability of damaged myocardium to efficiently regenerate[1, 2]. Following a myocardial infarction, approximately 1 billion cells are lost, and it has been estimated that 1-10 billion cells will be needed for treatment to restore function in the myocardium[26]. In order for these cell therapy treatments to replace the current treatments for cardiovascular disease, the production of engineered cardiac tissue should be reproducible, cost-effective, and scalable. Currently, large quantities of human CMs for myocardial repair are difficult to obtain, deliver efficiently through transplantation, and achieve the necessary integration with the host myocardium[27]. Due to insufficient numbers of human CMs for use in regenerative medicine and in the pharmaceutical industry for candidate drug testing, stem cell-derived cardiomyocytes (SC-CMs) are a desired cell type to produce in vitro[6].

Human induced pluripotent stem cell (hiPSC)-based cell therapies are an emerging treatment option to facilitate an enhanced and autologous approach to personalized medicine[3, 4]. New advancements in the field of regenerative medicine and stem cell engineering allow for the isolation and reprogramming of patient-specific somatic cells to produce hiPSCs. Following isolation, hiPSCs can then be cultured, expanded, and differentiated into cell types from all three germ layers, including specialized cells, such as cardiomyocytes (CMs), that are difficult to obtain from native tissue and cannot be cultured long-term in vitro[5]. Advancements in the scalable production of stem cell-derived cardiomyocytes (SC-CMs) are needed to revolutionize their application in regenerative medicine including treatment of heart failure patients, preclinical drug-testing, and studying disease mechanisms while overcoming interspecies and donor variations.

Cardiac differentiation protocols historically use the formation of embryoid bodies (EBs), small groups of self-aggregated pluripotent stem cells grown in suspension culture, while optimizing media components that enhance reproducibility, differentiation efficiency, and eliminate serum-based culture conditions. The size and shape of embryoid bodies can be difficult to control, and there is high variability in efficiency of cardiac differentiation between pluripotent stem cell lines[7-10]. An alternative 2D monolayer approach with fully-defined media components has also been used to produce contracting cardiac sheets[11]. This approach, however, requires larger surface areas during in vitro culture and has limitations in its scalability. CMs produced in these 2D monolayers are typically dissociated into single cells for further processing and assembly into 3D tissues[12], a requirement for their applicability in regenerative medicine and drug-testing applications. 3D tissues can be formed from 2D monolayers by a variety of methods including the self-assembly of cell aggregates generated by centrifugation[9, 13] or the stacking of multiple cell monolayers to create a 3D architecture[14, 15]. These tissue fabrication approaches create challenges during clinical translation due to the loss of cells and disruption of cell-cell junctions caused by the multiple cell-handling steps and the need for complex instrumentation and protocols.

New strategies to differentiate hiPSCs into CMs involve bioreactors that allow the scalable production of suspension EBs[16, 17]. Although these strategies possess great potential, incorporating hiPSCs within a photocrosslinkable biomaterial can be used to enhance spheroid uniformity, provide a uniform cellular microenvironment, guide stem cell differentiation, and provide physiological and biological cues to cells. Biomaterials are beneficial for use in tissue engineering due to the ability to tune their mechanical, chemical, and biological properties as well as promote cell adhesion and engraftment in the body and provide protection to the cells. The most common biomaterials used in cardiac tissue engineering to produce 3D tissues are natural materials Matrigel[18], collagen, gelatin[19], alginate[20], and fibrin[21] due to their low host response, enzymatically degradable sites, and ligands that support cell growth and adhesion. A hybrid biomaterial consists of natural and synthetic components to combine the advantages of these biomaterials to create a reproducible, biocompatible, cost-effective material that promotes cell adhesion and growth while also providing tunable properties. Previously, the hybrid biomaterial, PEG-fibrinogen, has proven successful in the encapsulation and direct differentiation of hiPSCs to form 3D cardiac tissues[22]. PEG-fibrinogen provides structural and biological components for the production of 3D cardiac tissues from hiPSCs while providing the capability for rapid photocrosslinking which allows for scale-up and the development of an automatable process.

Stem cell encapsulation and direct cardiac differentiation within supporting biomaterial scaffolds would advance the field by offering reproducible and scalable production of the functional human tissues needed in regenerative medicine and drug-testing applications. Producing cardiac tissues directly from pluripotent stem cells rather than assembling tissues using pre-differentiated CMs can eliminate multiple cell-handling steps that otherwise limit the potential for process automation and production scale-up. Previously, 3D cardiac tissues have been produced from hiPSCs in an ontomimetic manner through hiPSC encapsulation and direct differentiation in PEG-fibrinogen microislands[23]. Whereas there are multiple advantages to this platform over 2D monolayer differentiation, the cylindrical tissue geometry is not the optimal tissue shape for use in suspension bioreactor culture, high-throughput drug screening, or injectable cell therapy. The rapid hiPSC microsphere encapsulation system disclosed herein meets these needs, and can be used to directly produce functional cardiac tissue microspheres in a single unit operation.

Once large quantities of CMs are produced for cell therapy, the engineered cardiac tissue must be successfully delivered and engrafted to the infarcted myocardium, which has proven challenging. It is believed that the "ideal" cell type for the repair of a chronically damaged myocardium is a cell phenotypically similar to the host tissue[33-35]. Several cell sources have been investigated for the regeneration of function to the damaged heart including cardiosphere-derived cells (CDCs), which are composed of cardiac stem cells[36]. Clinical studies in animals[37, 38] and humans[39-41] showed that injected CDCs improved cardiac function and reduced scar tissue. Similarly, hPSCs have also successfully been used alone[42] and in combination with fibrin[43] or collagen[44], to produce SC-CMs for non-human primates and small animal models as well as for cardiac progenitors for human clinical trials. Ongoing clinical trials that infused or transplanted cells showed the positive effect of cell therapy; although the mechanisms of improvement are unclear, it is thought to involve paracrine signaling[45].

Described in this Example is a reproducible one-step approach for encapsulating hiPSCs within a PEG-fibrinogen hydrogel to form microspheres using a modified microfluidic oil-and-water emulsion technique. The described custom microfluidic system can produce approximately 75 hiPSC-encapsulated microspheres per minute with a cell density of 25 million cells/mL, an approximate diameter of 900 µm, and great control over roundness (0.96). Encapsulated hiPSCs remained viable in a PEG-fibrinogen hydrogel and continued to proliferate and grow to form larger and more dense microspheres. Microspheres consistently showed initial areas of contraction on day 8 of differentiation, with high cardiac differentiation efficiency by day 20 (>70%). Cardiac microspheres showed appropriate functional responses to pharmaceutical stimuli isoproterenol and propranolol. Furthermore, microsphere CMs responded to outside pacing frequencies up to 6.0 Hz. Microspheres were maintained in culture long term and developed cell-cell junctions and displayed aligned myofibrils. These results demonstrate the ability to reproducibly fabricate hiPSC-laden microspheres in an automatable manner with high CM yield and functionality for future applications in cell-therapy.

Methods for this Example

Figure 22:
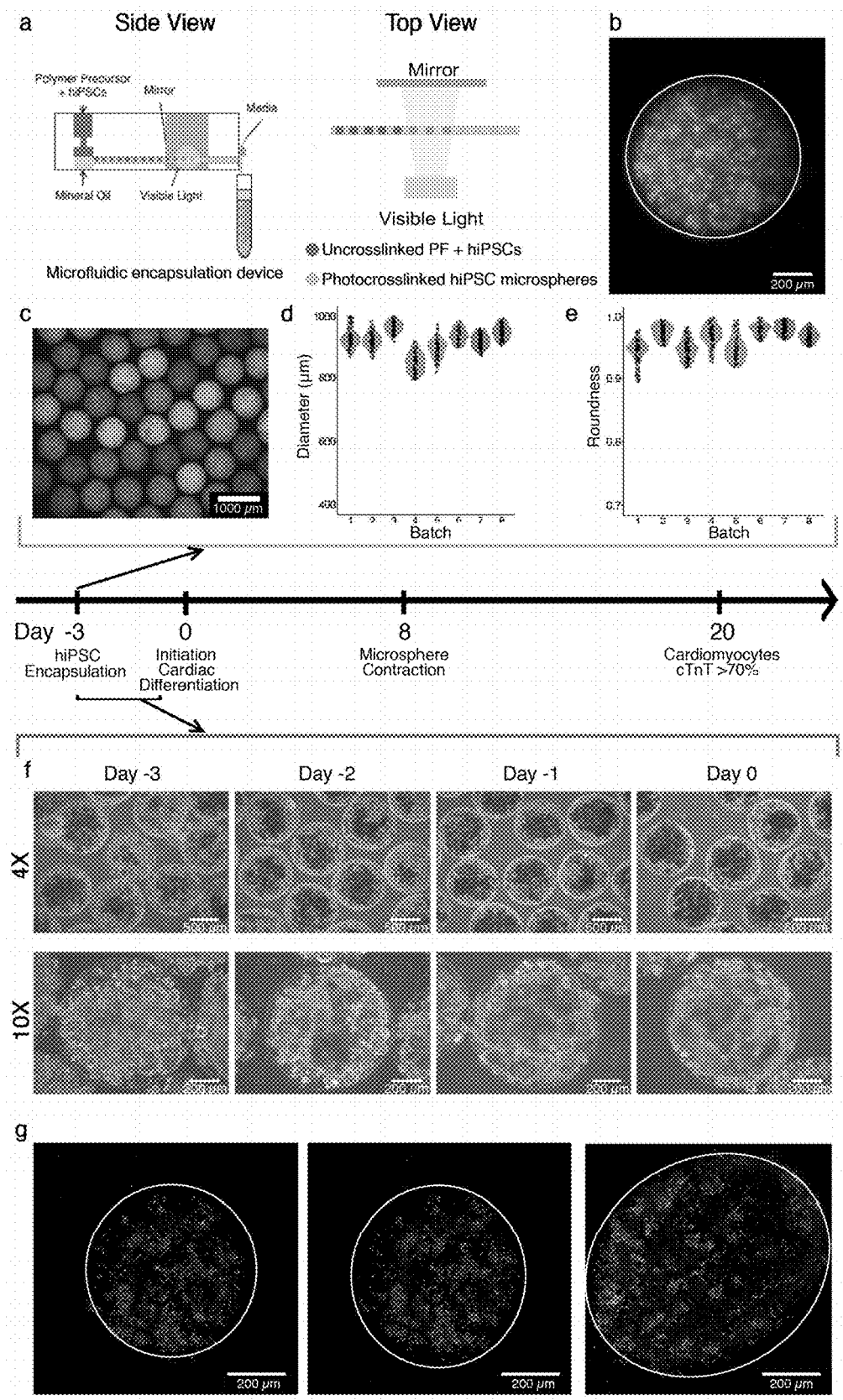
FIGS. 22A-22G. Rapid, highly reproducible hiPSC-encapsulation process to produce uniform cardiac tissue microspheres.

PEG-Fibrinogen Synthesis, PDMS Microfluidic Mold Fabrication, and XTT Viability Assay:
These methods are described in Example 1.
HiPSC Expansion and Maintenance:
IMR-90 Clone 1 and 19-9-11(WiCell) hiPSCs were cultured on hESC qualified Matrigel (Corning) using mTeSR-1 medium (Stem Cell Technologies) and passaged using Versene (Invitrogen). 24 h after passaging, hiPSCs were maintained in mTeSR-1 medium supplemented with 5 or 10 µM ROCK inhibitor (RI, Y-27632, Stem Cell Technologies).
HiPSC Microspheres Production and Cardiac Differentiation:
Liquid PEG-fibrinogen precursor solution was prepared by combining PEG-fibrinogen with 1.5 v/v % triethanolamine (TEOA), 3.9 µl/ml N-vinyl pyrrolidone (NVP), and 0.1 mM eosin Y (Fisher Scientific) photoinitiator (in PBS). HiPSCs were resuspended in PEG-fibrinogen precursor solution at 25 million cells/ml. The PEG-fibrinogen-cell mixture was added to one inlet of the custom built microfluidic system. In parallel, mineral oil was added to the other inlet of the microfluidic system which, when combined with the PEG-fibrinogen-cell mixture, causes the formation of spherical structures (FIG. 22A). Flowrates for the PEG-fibrinogen-cell mixture and mineral oil were set at 1 ml/h and 10 ml/h, respectively. A light source (Prior) was used to photocrosslink the liquid PEG-fibrinogen-cell mixture to form cell-laden microspheres. Microspheres were collected, washed with mTeSR-1 medium, and cultured in mTeSR-1 medium +5-10 µM RI for 24 h (day −3). Microspheres were then cultured for an additional 48 h in mTeSR-1 medium with daily media changes (days −2 and −1).
Three days after microsphere production (day 0), cardiac differentiation[59] was initiated by changing medium from mTeSR-1 to 4 ml RPMI/B27 w/o insulin (RPMI/B27-I, Thermo Fisher) supplemented with 12 µM CHIR (Stem Cell Technologies) per well. On day 1 (24 h after CHIR addition), medium was changed to 4 ml RPMI/B27-I. 48 h after that (day 3), 2 ml old media was combined with 2 ml fresh RPMI/B27-I supplemented with 5 µM IWP2 (Stem Cell Technologies). On day 5, media was replaced with 4 ml RPMI/B27-I and on day 7, RPMI/B27-I was changed to RPMI/B27 medium (Thermo Fisher). RPMI/B27 medium was replaced every three to four days following differentiation.

Microsphere Diameter, Roundness, and Early Growth Quantification:
Daily phase contrast images of microspheres were taken from the time of encapsulation (day −3) until initiation of cardiac differentiation (day 0). Microsphere diameter and size of eight individual batches were determined 24 h after encapsulation. Autofluorescence of the photoinitiator eosin Y in PEG-fibrinogen microspheres was captured on a fluorescence microscope at low magnification. Images were analyzed using ImageJ with standard plugins.
Microsphere growth prior to the initiation of spontaneous contraction was determined by analyzing phase contrast images on days −3, 0, 3, and 7 of differentiation by manual outlining of microspheres using ImageJ (n=10).
HiPSC Viability and Immunofluorescence Staining:
24 h after encapsulation, hiPSC viability within PEG-fibrinogen microspheres was assessed using a LIVE/DEAD® viability kit (Invitrogen) and images were taken using a fluorescent microscope (Nikon). Alexa Fluor 568-Phalloidin (Invitrogen) was used as described by the manufacture protocol to visualize actin filaments in encapsulated cells. Whole or dissociated cell-laden microspheres were immunostained with α-sarcomeric actinin (αSA, Sigma Aldrich), cardiac troponin T (cTnT, Invitrogen), and connexin 43 (Cx43, Sigma Aldrich). Microspheres were first rinsed with PBS and fixed in 4% paraformaldehyde (Electron Microscopy Sciences) or 50/50 ice cold acetone/ethanol (Cx43) for 20 min at room temperature or −20° C., respectively. Samples were rinsed with PBS and blocked with 3% FBS overnight at 4° C. or 1 hour at RT. Then, the cardiac microsphere samples were incubated in primary antibodies overnight at 4° C. or 1 hour at RT followed by the addition of Alexa Fluor 488 and Alexa Fluor 568 secondary antibodies (1:200). Nuclei were counterstained with 4',6-diamidino-2-phenylindole (DAPI, Molecular Probes) or Bisbenzimide H 3342 (MilliporeSigma). All samples were visualized using an Alsi confocal microscope (Nikon).
Microsphere Cardiomyocyte Dissociation:
Microspheres were washed with PBS followed by the incubation in dissociation solution containing collagenase type 2 (1 mg/ml, Worthington) at 37° C. for 2 h. The dissociation solution contained 120 mM NaCl, 5.4 mM KCl, 5 mM $MgSO_4$, 5 mM Na-pyruvate, 20 mM glucose, 20 mM taurine, and 10 mM HEPES (pH 6.9) supplemented with 30 µM $CaCl_2$) and 5 µM ROCK inhibitor. Microspheres were centrifuged, resuspended in 0.25% trypsin EDTA (Corning) and incubated at 37° C. for 5 min. Trypsin was neutralized using RPMI20 (20% FBS in RPMI1640 medium); cells were resuspended in RPMI20 with 5 µM ROCK inhibitor. Dissociated cells were plated on fibronectin coated (25 µg/ml, ThermoFisher) substrates (PDMS-coated glass coverslips or MEA) and incubated for three days.
Scanning Electron Microscopy:
For SEM, microspheres were rinsed with PBS and fixed in 4% paraformaldehyde and 2% glutaraldehyde in PBS for 15 min. The microspheres were rinsed with PBS and then 2% osmium tetraoxide was added for 1.5 h. After further PBS rinses, the microspheres were subjected to quick freeze with liquid nitrogen and then lyophilized. Dried microspheres were mounted on aluminum stubs, sputter-coated with gold (Pelco SC-6 sputter coater) and imaged using JEOL JSM-7000F scanning electron microscope.
Parallel Plate Mechanical Testing:
Day 5 microspheres were compressed to determine their mechanical properties. Using a micron-scale mechanical testing system (Microsquisher, CellScale)[63], microspheres were compressed using a Tungsten cantilever beam (modulus=411 GPa, diameter=203.2 μm). All microsphere samples were compressed in PBS at 37° C. Stress-strain characteristics of day 5 microspheres were obtained and the elastic modulus was determined within the linear 5-20% strain regime (n=3 samples).

Multielectrode Array:

Day 20 and 50 dissociated microsphere CMs were seeded onto a fibronectin coated S2 type MEA200/30-Ti-gr (Multichannel Systems) and cultured for at least 24 h. Adhering microsphere CMs were perfused with Tyrode's solution, composed of 1.8 mM $CaCl_2$), 5 mM glucose, 5 mM HEPES, 1 mM $MgCl_2$, 5.4 mM KCl, 135 mM NaCl, and 0.33 mM $NaH_2PO_4$ at pH 7.4 and 37° C. Once stabilized, field potentials of spontaneous contractions were recorded at a sampling frequency of 10 kHz. Drug response of day 20 microsphere CMs was tested by adding the β-adrenergic agonist isoproterenol (1 μM) and antagonist propranolol (1 μM). Day 50 microsphere CMs were exogenously paced from 0.5-6.0 Hz.

Results for this Example

Rapid, One-Step Microfluidic Encapsulation Device Produced Uniform and Round hiPSC Microspheres:

Within the microfluidic device, the combination of liquid PEG-fibrinogen precursor solution and hiPSCs was pumped into a custom made PDMS mold opposite an oil phase where spheroids were formed at the junction of the PDMS mold and then photocrosslinked as they traveled through the outlet channel (FIG. 22A). The precursor solution moved with a constant flow rate through the microfluidic device while achieving sufficient crosslinking of approximately 1.6 seconds to form each microsphere. Encapsulated hiPSCs (25× $10^6$ cells/ml PEG-fibrinogen) displayed high viability (FIG. 22B) and a round morphology with some cells being exposed beyond the PEG-fibrinogen hydrogel boundary (FIG. 22F). Approximately 75 microsphere-encapsulated hiPSCs were produced every minute with tight control over size and circularity (FIG. 22C-22E). On the day of encapsulation (day −3, FIG. 22C), the initial microsphere diameter was 908±40 μm (FIG. 22D) and roundness was 0.96±0.02 (FIG. 22E, n=485 microspheres, 8 independent batches). Microsphere-encapsulated hiPSCs displayed well-defined boundaries with cells being distributed within the PEG-fibrinogen hydrogel. Following encapsulation, cells first grew within the original hydrogel boundaries, maintaining the fabricated initial microsphere diameter. HiPSCs were cultured in their pluripotent state for three days before cardiac differentiation was initiated on day 0 (three days being sufficient for hiPSCs to adjust to their new, 3D hydrogel microenvironment and to initiate cell growth within the hydrogel, forming a continuous tissue over time). Microsphere-encapsulated hiPSCs followed the same time course, with cells initially growing within the borders of the PEG-fibrinogen hydrogel, occupying the majority of the spherical volume (FIG. 22F). The microspheres displayed high cell density throughout the spheroids as shown by immunofluorescent labeling of the nuclei in cryosections (FIG. 22G).

Encapsulated hiPSCs Grew to Form Continuous Cell-Laden Microspheres:

Before culture medium was switched to initiate cardiac differentiation on day 0, hiPSCs grew within the initial microsphere boundaries (FIGS. 22F-22G). After day 0, differentiating cells continued to grow within and then beyond the initial microsphere boundaries to produce denser and larger tissues with decreasing circularity (FIG. 23A).

Figure 23:
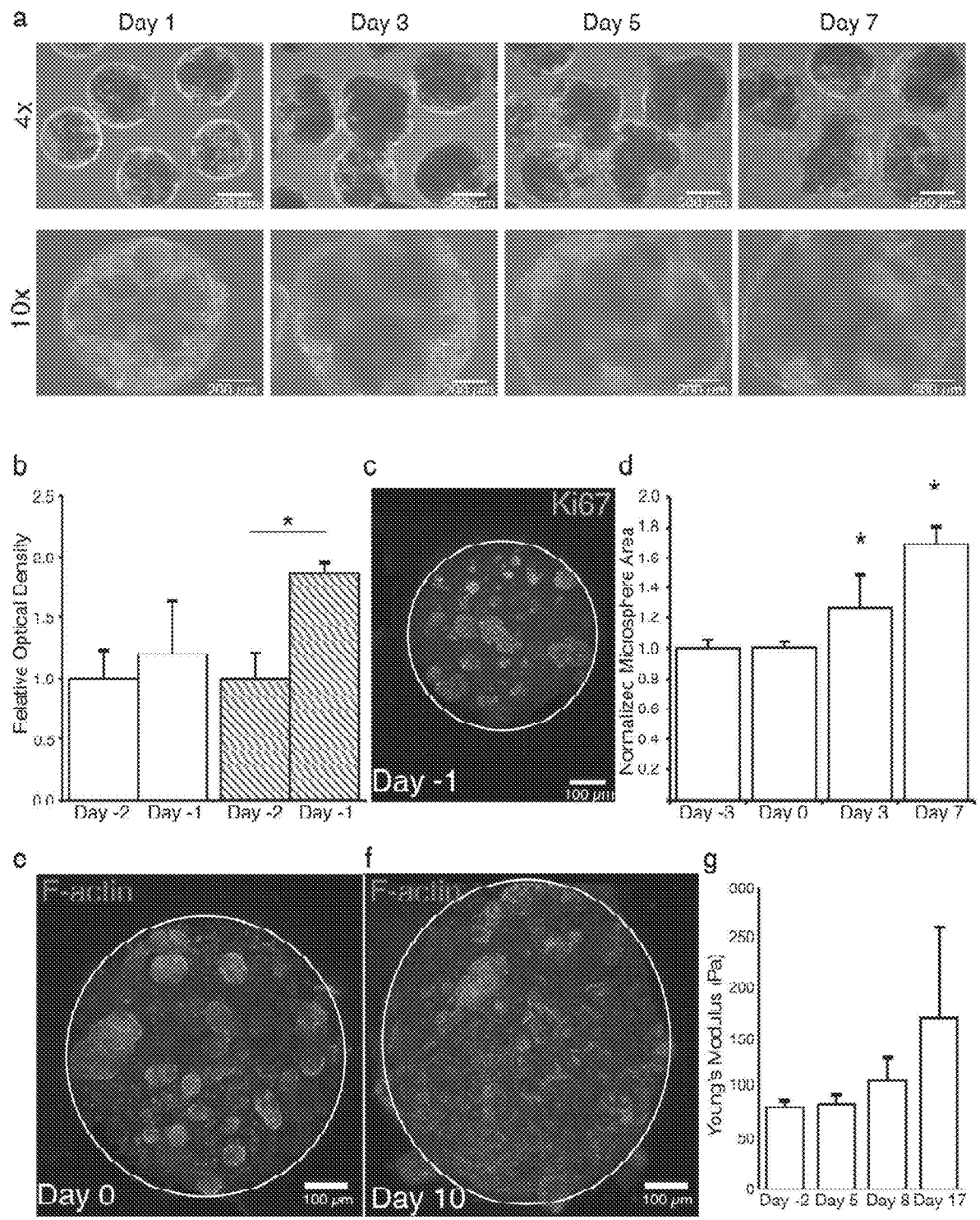
FIGS. 23A-23G. PEG-fibrinogen encapsulated hiPSC microspheres grew to form uniform tissues.

For two different hiPSC lines, IMR90 and 19-9-11, XTT assay confirmed higher metabolic activity on day −1 than on day −2 for encapsulated hiPSC-microspheres (FIG. 23B), which combined with visual phase contrast data (FIG. 23A and Ki67 staining (FIG. 23C), confirms an increase in the number of viable and proliferative cells. By day 3, microsphere diameter increased 1.27 times when compared to day 0, and further increased to 1.7 times by day 7 of differentiation (FIG. 23D). One factor influencing stem cell differentiation is the mechanical stiffness of the cellular microenvironment. For 2D culture on polystyrene tissue culture flask, the substrate is stiffer than conditions during embryonic development, which range in the order of 100 to 1,000 Pa. For that reason, prior to and during differentiation microspheres were tested for their stiffness for encapsulated hiPSCs. During compression testing, the elastic modulus was 81±7 Pa, 85±8, 107±23, and 170±91 Pa, respectively, on days −2, 5, 8, and 17 (FIG. 23G), providing a soft microenvironment for the cells during differentiation. The morphology of the cells in the microspheres changed from the rounded morphology of hiPSCs on day 0 (FIG. 23E) to elongated cells following differentiation (day 10, FIG. 23F), indicative of cardiac differentiation.

Figure 24:
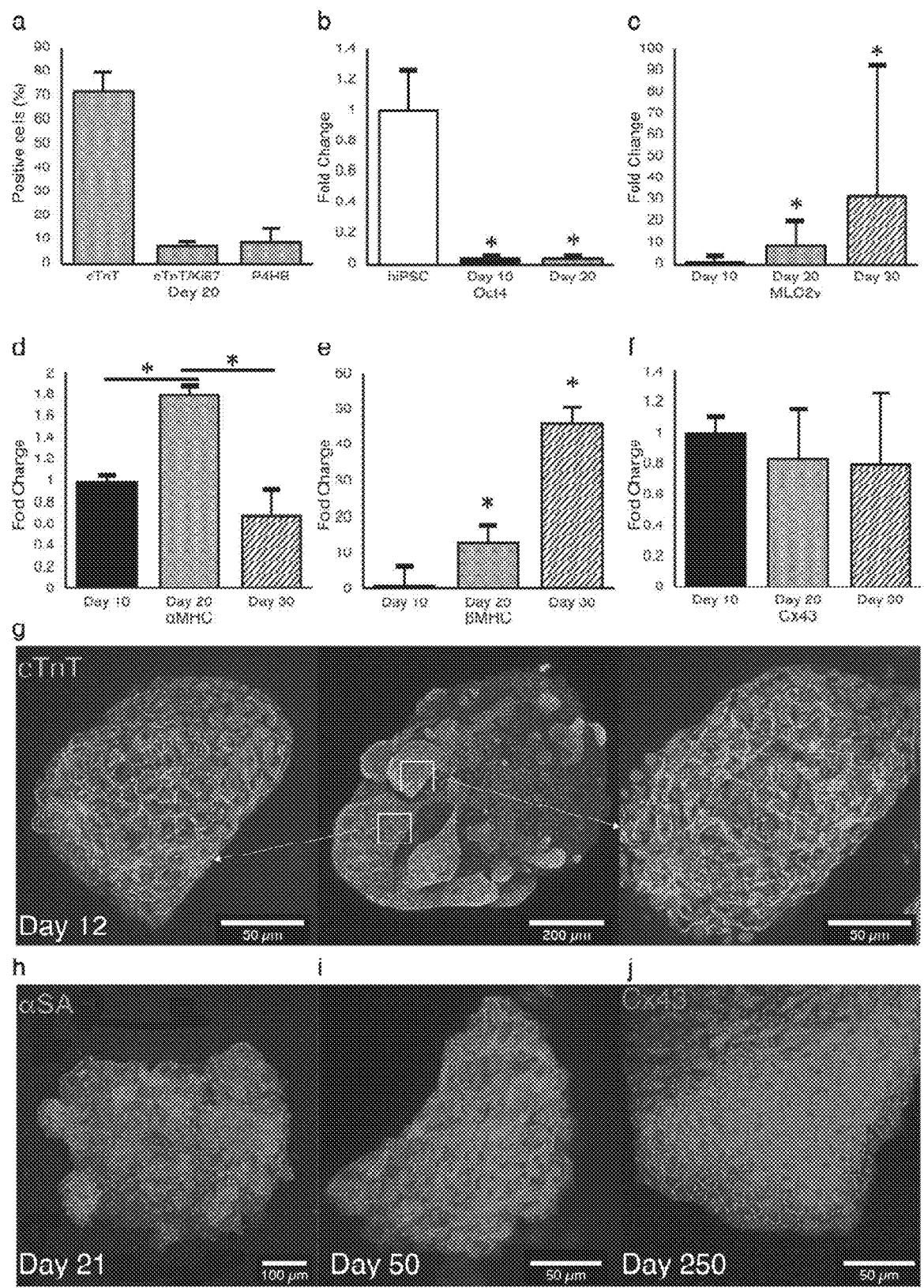
FIGS. 24A-24J. 3D cardiac differentiation enabled high CM yield and appropriate gene expression in microspheres.

3D hiPSC-Laden Hydrogels Become Cardiac Microspheres:

The microfluidic device was successfully used to produce hiPSC encapsulated microspheres in a rapid manner that resulted in spontaneously contracting cardiac microspheres over time. Microspheres were cultured in suspension and stagnant conditions; as a result of the spherical architecture, internal cell alignment and uniform cell growth was difficult to achieve with increasing culture time, which was seen when studying the shape and cell arrangement within cardiac microspheres. Dense microspheres consistently started to spontaneously contract on day 8 of differentiation, with approximately 78% contracting microspheres by day 10 (n=90 microspheres). Differentiation efficiency was consistently high between batches, with 71.6±8.4% total CMs (cTnT+), 7.1±1.7% proliferating CMs (cTnT+/Ki67+), and 8.41±6.5% fibroblasts (P4HB+) (n=3 individual batches, FIG. 24A). Microspheres displayed appropriate changes in gene expression measured using RT-qPCR including a significant decrease in the fold change of pluripotent gene OCT4 from hiPSCs to day 10 and 20 of differentiation (FIG. 24B). The expression of ventricular CM subtype, MLC2v, significantly increased from day 10 to day 30 (FIG. 24C). Cardiac gene, αMHC, significantly increased from day 10 to day 20 and then decreased from day 20 to day 30 while MHC continued to increase from day 10 to day 30 (FIGS. 24D-24E). The presence of functional protein Cx43 was also detected on days 10, 20, and 30 (FIG. 24F). Immunofluorescent staining demonstrated the presence of functional cardiac markers cardiac troponin T (cTnT) at day 12 (FIG. 24G), demonstrating differentiation throughout the spheroid. From day 21 to day 50, sections labeled with sarcomeric alpha-actinin (αSA) show the sarcomeres becoming more aligned, a feature of maturing CMs (FIGS. 24H and 24I). The cells exhibit cell-cell interactions as shown by the labeling of connexin 43 (Cx43) in day 250 sections (FIG. 24J).

Figure 25:
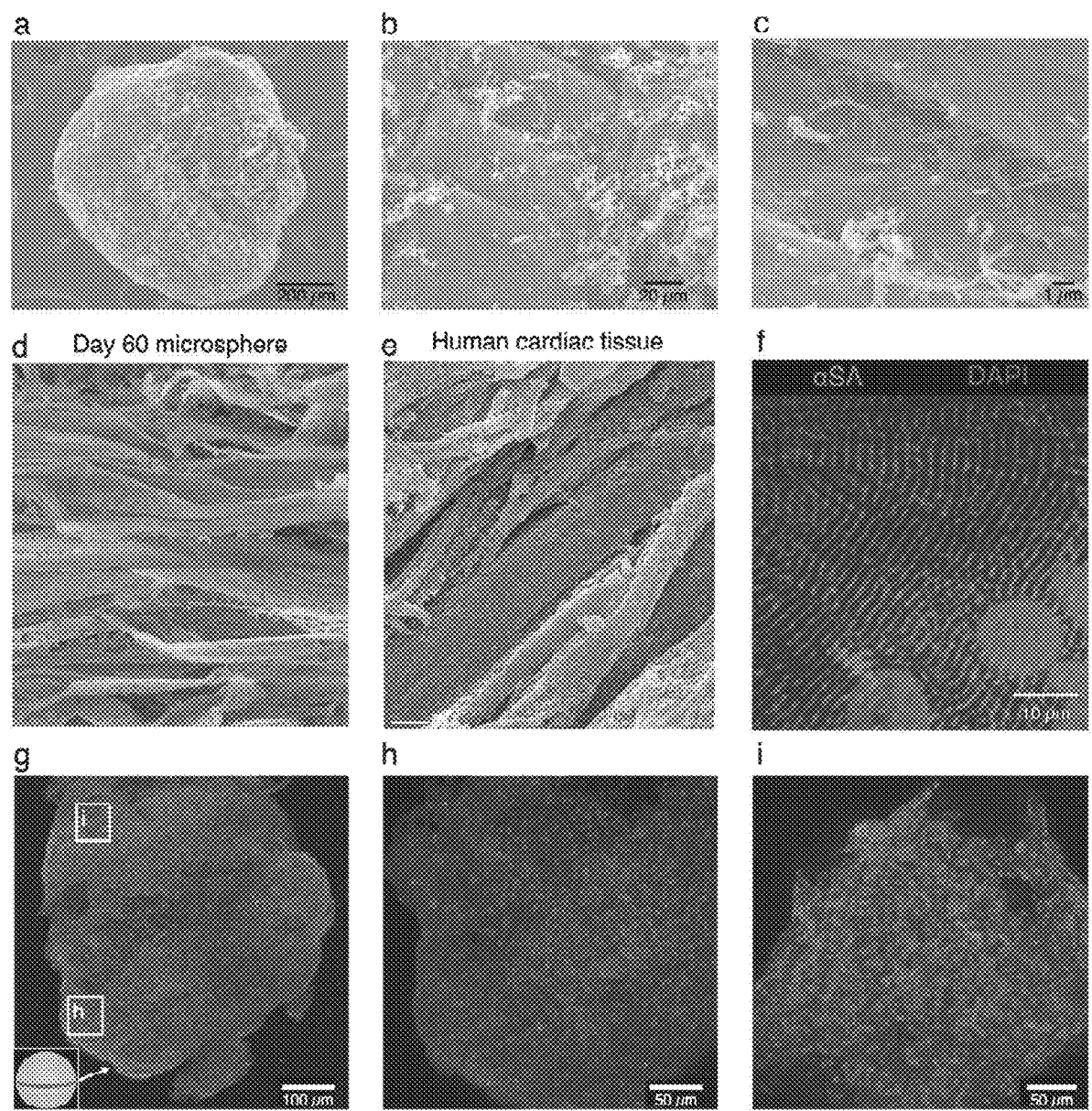
FIGS. 25A-25I. Cardiac tissue spheroids displayed features of maturing cells.

Cardiac Microspheres Showed Dynamic Remodeling of their PEG-Fibrinogen Microenvironment:

With progressing culture time, encapsulated cells remodeled their PEG-fibrinogen microenvironment by producing ECM proteins and differentiating into contracting cardiac tissues. Scanning electron microscopy (SEM) of microspheres showed a smooth cell-based surface (FIG. 25A). At higher magnification, a combination of tightly-connected cells and ECM deposition was revealed to be present on the microsphere surface (FIG. 25B). Day 60 microspheres cells showed some aligning cells (FIG. 25B), with neighboring cells forming cell-cell junctions (FIG. 25C). Additionally, day 60 microspheres contained aligned myofibril arrangement (FIG. 25D), similar to SEM images of native human heart tissue (FIG. 25E)[24]. Understanding CM functionality on a tissue and single-cell level is often desired. We have successfully dissociated cardiac microspheres into single CMs, with CMs spontaneously contracting after dissociation. CMs attached to unpatterned PDMS surfaces with elongated cell morphology, which is normal for maturing CMs[23]. Dissociated cells were also immunofluorescently stained with the cardiac marker αSA to visualize and quantify developed sarcomeres (FIG. 25F). CMs displayed defined sarcomere structures with internal alignment and uniform spacing of 1.85 μm. Organized sarcomere arrangement influences the mechanical contractile output and is indicative of cardiomyocyte maturation. To ensure successful cardiac differentiation throughout the spheroid, a cryostat was used to section the spheres. The cryosections were immunofluorescently labeled with cardiac marker, αSA, and DAPI for the nuclei. Sections varying in size confirm positive cardiac differentiation throughout the entire spheroid; a representative section from the middle of the spheroid is shown in FIG. 25F with zoomed in regions from the section shown in FIGS. 25H-25I.

Figure 26:
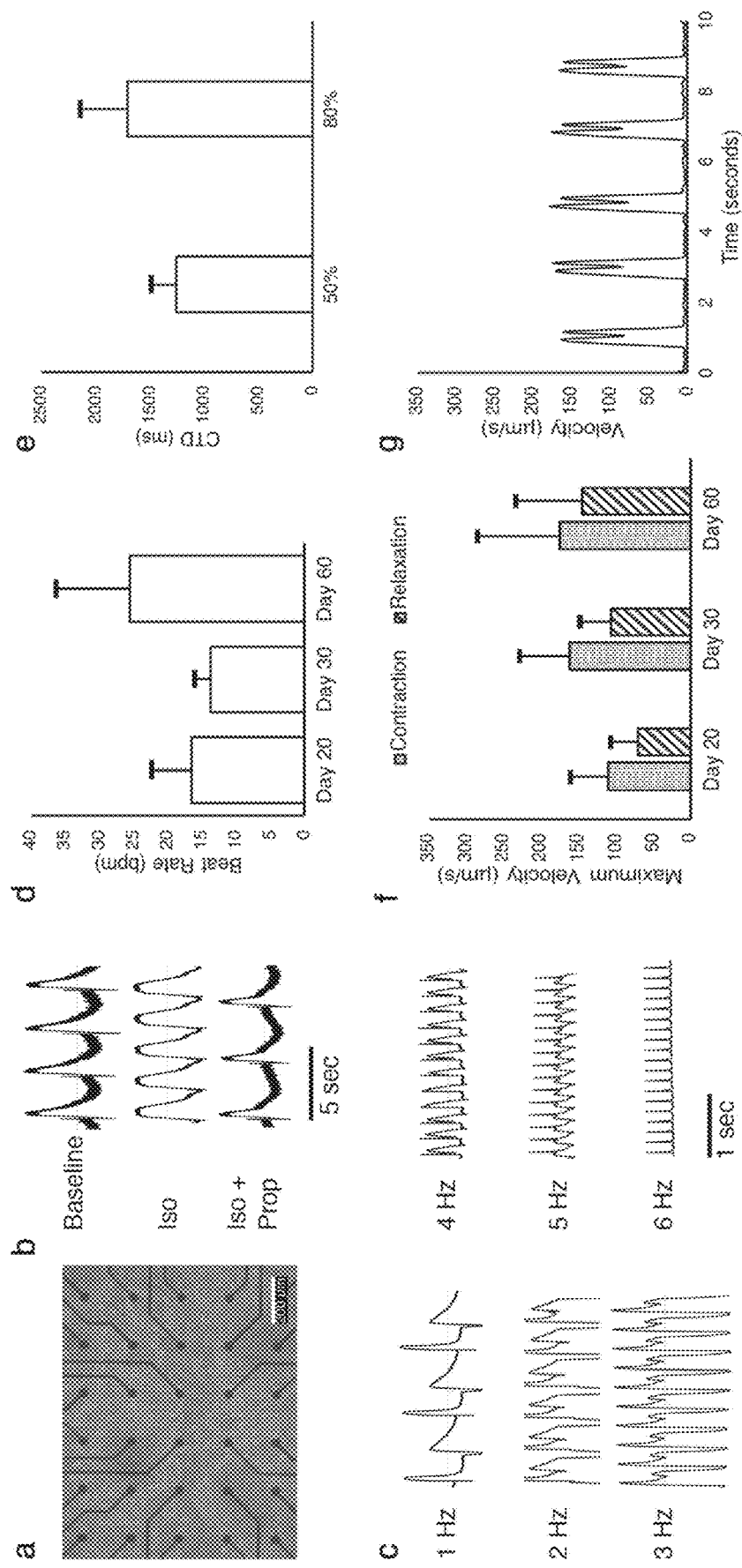
FIGS. 26A-26G. Microsphere CMs responded to pharmacological and electrical stimuli indicating functionality.

Microsphere CMs Responded to Drug Treatment and Electrical Stimuli:

Response to these pharmacological and electrical stimuli indicate functionality and maturity of the resulting CMs—an important step for the successful translation of engineered cardiac tissues towards regenerative medicine and drug-screening. Using MEA analysis (FIGS. 26A-26C), the response of day 20 cardiac microspheres to pharmacologic stimuli was evaluated (including the β-adrenergic agonist, isoproterenol, and the β-adrenergic antagonist, propranolol). Isoproterenol increases the frequency of contraction, while the subsequent addition of propranolol slowed down the rate of contraction (FIG. 26B). In addition to drug-testing, the response of cardiac microspheres to electrical pacing was also evaluated. Day 50 microsphere CMs exhibited 1:1 capture up to 6.0 Hz when paced on the MEA. Contraction analysis was done using a custom MATLAB script[25] in which videos were converted into a set of tiff files and then macroblock tracing was done to detect the frequency of contraction as well as the contraction and relaxation velocities. Microspheres contracted at a frequency of 16.6±5.9, 13.8±2.3, and 25.6±10.8 beats per minute on days 20, 30, and 60 respectively (FIG. 26D). The cardiac spheroids had a calcium transient duration (CTD) at 50% repolarization of 1256 ms and 1713 ms at 80% repolarization (FIG. 26E). The contraction and relaxation velocities were 110±49, 161±69, and 175±112 μm/s on days 20, 30, and 60 with relaxation velocities of 70±36, 106±42, and 146±88 μm/s, respectively (FIG. 26F-26G).

REFERENCES CITED IN THIS EXAMPLE

1. Mercola M, Ruiz-Lozano P and Schneider M D. Cardiac muscle regeneration: lessons from development. *Genes Dev.* 2011; 25:299-309.
2. Zhang Y, Mignone J and MacLellan W R. Cardiac Regeneration and Stem Cells. *Physiol Rev.* 2015; 95:1189-204.
3. Zhao T, Zhang Z N, Westenskow P D, Todorova D, Hu Z, Lin T, Rong Z, Kim J, He J, Wang M, Clegg D O, Yang Y G, Zhang K, Friedlander M and Xu Y. Humanized Mice Reveal Differential Immunogenicity of Cells Derived from Autologous Induced Pluripotent Stem Cells. *Cell Stem Cell.* 2015; 17:353-9.
4. Garbern J C and Lee R T. Cardiac stem cell therapy and the promise of heart regeneration. *Cell Stem Cell.* 2013; 12:689-98.
5. Rajamohan D, Matsa E, Kalra S, Crutchley J, Patel A, George V and Denning C. Current status of drug screening and disease modelling in human pluripotent stem cells. *Bioessays.* 2013; 35:281-98.
6. Gwathmey J K, Tsaioun K and Hajjar R J. Cardionomics: a new integrative approach for screening cardiotoxicity of drug candidates. *Expert Opin Drug Metab Toxicol.* 2009; 5:647-60.
7. Rajala K, Pekkanen-Mattila M and Aalto-Setala K. Cardiac differentiation of pluripotent stem cells. *Stem Cells Int.* 2011; 2011: 383-709.
8. Kehat I, Kenyagin-Karsenti D, Snir M, Segev H, Amit M, Gepstein A, Livne E, Binah O, Itskovitz-Eldor J and Gepstein L. Human embryonic stem cells can differentiate into myocytes with structural and functional properties of cardiomyocytes. *J Clin Invest.* 2001; 108: 407-14.
9. Burridge P W, Anderson D, Priddle H, Barbadillo Munoz M D, Chamberlain S, Allegrucci C, Young L E and Denning C. Improved human embryonic stem cell embryoid body homogeneity and cardiomyocyte differentiation from a novel V-96 plate aggregation system highlights interline variability. *Stem Cells.* 2007; 25:929-38.
10. Osafune K, Caron L, Borowiak M, Martinez R J, Fitz-Gerald C S, Sato Y, Cowan C A, Chien K R and Melton D A. Marked differences in differentiation propensity among human embryonic stem cell lines. *Nat Biotechnol.* 2008; 26:313-5.
11. Burridge P W, Matsa E, Shukla P, Lin Z C, Churko J M, Ebert A D, Lan F, Diecke S, Huber B, Mordwinkin N M, Plews J R, Abilez O J, Cui B, Gold J D and Wu J C. Chemically defined generation of human cardiomyocytes. *Nat Methods.* 2014; 11:855-60.
12. Jenkins M J and Farid S S. Human pluripotent stem cell-derived products: advances towards robust, scalable and cost-effective manufacturing strategies. *Biotechnol J.* 2015; 10:83-95.
13. Burridge P W, Thompson S, Millrod M A, Weinberg S, Yuan X, Peters A, Mahairaki V, Koliatsos V E, Tung L and Zambidis E T. A universal system for highly efficient cardiac differentiation of human induced pluripotent stem cells that eliminates interline variability. *PLoS One.* 2011; 6:e18293.
14. Shimizu T, Yamato M, Kikuchi A and Okano T. Cell sheet engineering for myocardial tissue reconstruction. *Biomaterials.* 2003; 24:2309-16.
15. Nagase K, Kobayashi J and Okano T. Temperature-responsive intelligent interfaces for biomolecular separation and cell sheet engineering. *J R Soc Interface.* 2009; 6 Suppl 3:S293-309.
16. Fonoudi H, Ansari H, Abbasalizadeh S, Larijani M R, Kiani S, Hashemizadeh S, Zarchi A S, Bosman A, Blue G M, Pahlavan S, Perry M, Orr Y, Mayorchak Y, Vandenberg J, Talkhabi M, Winlaw D S, Harvey R P, Aghdami N and Baharvand H. A Universal and Robust Integrated Platform for the Scalable Production of Human Cardiomyocytes From Pluripotent Stem Cells. *Stem Cells Transl Med.* 2015; 4:1482-94.

17. Kempf H, Olmer R, Kropp C, Ruckert M, Jara-Avaca M, Robles-Diaz D, Franke A, Elliott D A, Wojciechowski D, Fischer M, Roa Lara A, Kensah G, Gruh I, Haverich A, Martin U and Zweigerdt R. Controlling expansion and cardiomyogenic differentiation of human pluripotent stem cells in scalable suspension culture. *Stem Cell Reports.* 2014; 3:1132-46.
18. Laflamme M A, Chen K Y, Naumova A V, Muskheli V, Fugate J A, Dupras S K, Reinecke H, Xu C, Hassanipour M, Police S, O'Sullivan C, Collins L, Chen Y, Minami E, Gill E A, Ueno S, Yuan C, Gold J and Murry C E. Cardiomyocytes derived from human embryonic stem cells in pro-survival factors enhance function of infarcted rat hearts. *Nat Biotechnol.* 2007; 25:1015-24.
19. Huyer L D, Montgomery M, Zhao Y, Xiao Y, Conant G, Korolj A and Radisic M. Biomaterial based cardiac tissue engineering and its applications. *Biomed Mater.* 2015; 10: 034004.
20. Landa N, Miller L, Feinberg M S, Holbova R, Shachar M, Freeman I, Cohen S and Leor J. Effect of injectable alginate implant on cardiac remodeling and function after recent and old infarcts in rat. *Circulation.* 2008; 117: 1388-96.
21. Wendel J S, Ye L, Zhang P, Tranquillo R T and Zhang J J. Functional consequences of a tissue-engineered myocardial patch for cardiac repair in a rat infarct model. *Tissue Eng Part A.* 2014; 20:1325-35.
22. Kerscher P, Turnbull I C, Hodge A J, Kim J, Seliktar D, Easley C J, Costa K D and Lipke E A. Direct hydrogel encapsulation of pluripotent stem cells enables ontomimetic differentiation and growth of engineered human heart tissues. *Biomaterials.* 2016; 83:383-95.
23. Kerscher P, Turnbull I C, Hodge A J, Kim J, Seliktar D, Easley C J, Costa K D and Lipke E A. Direct hydrogel encapsulation of pluripotent stem cells enables ontomimetic differentiation and growth of engineered human heart tissues. *Biomaterials.* 2015; 83:383-395.
24. Saunders R and Amoroso M. SEM investigation of heart tissue samples. *J Phys: Conf Ser* 2010; 241
25. Huebsch N, Loskill P, Mandegar M A, Marks N C, Sheehan A S, Ma Z, Mathur A, Nguyen T N, Yoo J C, Judge L M, Spencer C I, Chukka A C, Russell C R, So P L, Conklin B R and Healy K E. Automated Video-Based Analysis of Contractility and Calcium Flux in Human-Induced Pluripotent Stem Cell-Derived Cardiomyocytes Cultured over Different Spatial Scales. *Tissue Eng Part C Methods.* 2015; 21:467-79.
26. Zweigerdt R, Olmer R, Singh H, Haverich A and Martin U. Scalable expansion of human pluripotent stem cells in suspension culture. *Nat Protocols.* 2011; 6:689-700.
27. Hartman M E, Dai D F and Laflamme M A. Human pluripotent stem cells: Prospects and challenges as a source of cardiomyocytes for in vitro modeling and cell-based cardiac repair. *Adv Drug Deliv Rev.* 2016; 96:3-17.
28. Li Z, Guo X, Matsushita S and Guan J. Differentiation of cardiosphere-derived cells into a mature cardiac lineage using biodegradable poly(N-isopropylacrylamide) hydrogels. *Biomaterials.* 2011; 32:3220-32.
29. Shao Y, Sang J and Fu J. On human pluripotent stem cell control: The rise of 3D bioengineering and mechanobiology. *Biomaterials.* 2015; 52:26-43.
30. Guyette J P, Charest J M, Mills R W, Jank B J, Moser P T, Gilpin S E, Gershlak J R, Okamoto T, Gonzalez G, Milan D J, Gaudette G R and Ott H C. Bioengineering Human Myocardium on Native Extracellular Matrix. *Circ Res.* 2016; 118:56-72.
31. Young J L and Engler A J. Hydrogels with time-dependent material properties enhance cardiomyocyte differentiation in vitro. *Biomaterials.* 2011; 32:1002-9.
32. Hazeltine L B, Badur M G, Lian X, Das A, Han W and Palecek S P. Temporal impact of substrate mechanics on differentiation of human embryonic stem cells to cardiomyocytes. *Acta Biomater.* 2014; 10:604-12.
33. Li T S, Cheng K, Malliaras K, Smith R R, Zhang Y, Sun B, Matsushita N, Blusztajn A, Terrovitis J, Kusuoka H, Marban L and Marban E. Direct comparison of different stem cell types and subpopulations reveals superior paracrine potency and myocardial repair efficacy with cardiosphere-derived cells. *J Am Coll Cardiol.* 2012; 59:942-53.
34. Oskouei B N, Lamirault G, Joseph C, Treuer A V, Landa S, Da Silva J, Hatzistergos K, Dauer M, Balkan W, McNiece I and Hare J M. Increased potency of cardiac stem cells compared with bone marrow mesenchymal stem cells in cardiac repair. *Stem Cells Transl Med.* 2012; 1:116-24.
35. Citro L, Naidu S, Hassan F, Kuppusamy M L, Kuppusamy P, Angelos M G and Khan M. Comparison of human induced pluripotent stem-cell derived cardiomyocytes with human mesenchymal stem cells following acute myocardial infarction. *PLoS One.* 2014; 9:e116281.
36. Sousonis V, Nanas J and Terrovitis J. Cardiosphere-derived progenitor cells for myocardial repair following myocardial infarction. *Curr Pharm Des.* 2014; 20:2003-11.
37. Cheng K, Malliaras K, Smith R R, Shen D, Sun B, Blusztajn A, Xie Y, Ibrahim A, Aminzadeh M A, Liu W, Li T S, De Robertis M A, Marban L, Czer L S, Trento A and Marban E. Human cardiosphere-derived cells from advanced heart failure patients exhibit augmented functional potency in myocardial repair. *JACC Heart Fail.* 2014; 2:49-61.
38. Suzuki G, Weil B R, Leiker M M, Ribbeck A E, Young R F, Cimato T R and Canty J M, Jr. Global intracoronary infusion of allogeneic cardiosphere-derived cells improves ventricular function and stimulates endogenous myocyte regeneration throughout the heart in swine with hibernating myocardium. *PLoS One.* 2014; 9: e113009.
39. Makkar R R, Smith R R, Cheng K, Malliaras K, Thomson L E, Berman D, Czer L S, Marban L, Mendizabal A, Johnston P V, Russell S D, Schuleri K H, Lardo A C, Gerstenblith G and Marban E. Intracoronary cardiosphere-derived cells for heart regeneration after myocardial infarction (CADUCEUS): a prospective, randomised phase 1 trial. *Lancet.* 2012; 379:895-904.
40. Welt F G, Gallegos R, Connell J, Kajstura J, D'Amario D, Kwong R Y, Coelho-Filho O, Shah R, Mitchell R, Leri A, Foley L, Anversa P and Pfeffer M A. Effect of cardiac stem cells on left-ventricular remodeling in a canine model of chronic myocardial infarction. *Circ Heart Fail.* 2013; 6:99-106.
41. Tarui S, Ishigami S, Ousaka D, Kasahara S, Ohtsuki S, Sano S and Oh H. Transcoronary infusion of cardiac progenitor cells in hypoplastic left heart syndrome: Three-year follow-up of the Transcoronary Infusion of Cardiac Progenitor Cells in Patients With Single-Ventricle Physiology (TICAP) trial. *J Thorac Cardiovasc Surg.* 2015; 150:1198-1207, 1208 el-2.
42. Chong J J, Yang X, Don C W, Minami E, Liu Y W, Weyers J J, Mahoney W M, Van Biber B, Cook S M, Palpant N J, Gantz J A, Fugate J A, Muskheli V, Gough G M, Vogel K W, Astley C A, Hotchkiss C E, Baldessari A, Pabon L, Reinecke H, Gill E A, Nelson V, Kiem H P, Laflamme M A and Murry C E. Human embryonic-stemcell-derived cardiomyocytes regenerate non-human primate hearts. *Nature.* 2014; 510:273-7.
43. Menasche P, Vanneaux V, Hagege A, Bel A, Cholley B, Cacciapuoti I, Parouchev A, Benhamouda N, Tachdjian G, Tosca L, Trouvin J H, Fabreguettes J R, Bellamy V, Guillemain R, Suberbielle Boissel C, Tartour E, Desnos M and Larghero J. Human embryonic stem cell-derived cardiac progenitors for severe heart failure treatment: first clinical case report. *Eur Heart J.* 2015; 36:2011-7.
44. Joanne P, Kitsara M, Boitard S E, Naemetalla H, Vanneaux V, Pernot M, Larghero J, Forest P, Chen Y, Menasche P and Agbulut O. Nanofibrous clinical-grade collagen scaffolds seeded with human cardiomyocytes induces cardiac remodeling in dilated cardiomyopathy. *Biomaterials.* 2016; 80:157-68.
45. Mirotsou M, Jayawardena T M, Schmeckpeper J, Gnecchi M and Dzau V J. Paracrine mechanisms of stem cell reparative and regenerative actions in the heart. *Journal of Molecular and Cellular Cardiology.* 2011; 50:280-289.
46. Pettinato G, Wen X and Zhang N. Formation of well-defined embryoid bodies from dissociated human induced pluripotent stem cells using microfabricated cell-repellent microwell arrays. *Sci Rep.* 2014; 4:7402.
47. Ng E S, Davis R P, Azzola L, Stanley E G and Elefanty A G. Forced aggregation of defined numbers of human embryonic stem cells into embryoid bodies fosters robust, reproducible hematopoietic differentiation. *Blood.* 2005; 106:1601-3.
48. Beauchamp P, Moritz W, Kelm J M, Ullrich N D, Agarkova I, Anson B D, Suter T M and Zuppinger C. Development and Characterization of a Scaffold-Free 3D Spheroid Model of Induced Pluripotent Stem Cell-Derived Human Cardiomyocytes. *Tissue engineering Part C, Methods.* 2015; 21:852-61.
49. Jiang Z, Xia B, McBride R and Oakey J. A microfluidic-based cell encapsulation platform to achieve high long-term cell viability in photopolymerized PEGNB hydrogel microspheres. *J Mater Chem B Mater Biol Med.* 2017; 5:173-180.
50. Pradhan S, Clary J M, Seliktar D and Lipke E A. A three-dimensional spheroidal cancer model based on PEG-fibrinogen hydrogel microspheres. *Biomaterials.* 2017; 115:141-154.
51. El-Kirat-Chatel S, Beaussart A, Vincent S P, Abelian Flos M, Hols P, Lipke P N and Dufrene Y F. Forces in yeast flocculation. *Nanoscale.* 2015; 7:1760-7.
52. Kang H W, Lee S J, Ko I K, Kengla C, Yoo J J and Atala A. A 3D bioprinting system to produce human-scale tissue constructs with structural integrity. *Nat Biotechnol.* 2016; 34:312-9.
53. Ouyang L, Yao R, Mao S, Chen X, Na J and Sun W. Three-dimensional bioprinting of embryonic stem cells directs highly uniform embryoid body formation. *Biofabrication.* 2015; 7:044101.
54. Ma Y, Ji Y, Huang G, Ling K, Zhang X and Xu F. Bioprinting 3D cell-laden hydrogel microarray for screening human periodontal ligament stem cell response to extracellular matrix. *Biofabrication.* 2015; 7:044105.
55. Chan H F, Zhang Y and Leong K W. Efficient One-Step Production of Microencapsulated Hepatocyte Spheroids with Enhanced Functions. *Small.* 2016.
56. Zhao X, Liu S, Yildirimer L, Zhao H, Ding R, Wang H, Cui W and Weitz D. Injectable Stem Cell-Laden Photocrosslinkable Microspheres Fabricated Using Microfluidics for Rapid Generation of Osteogenic Tissue Constructs. *Advanced Functional Materials.* 2016:n/a-n/a.
57. Malliaras K, Li T S, Luthringer D, Terrovitis J, Cheng K, Chakravarty T, Galang G, Zhang Y, Schoenhoff F, Van Eyk J, Marban L and Marban E. Safety and efficacy of allogeneic cell therapy in infarcted rats transplanted with mismatched cardiosphere-derived cells. *Circulation.* 2012; 125:100-12.
58. Rossow T, Lienemann P S and Mooney D J. Cell Microencapsulation by Droplet Microfluidic Templating. *Macromolecular Chemistry and Physics.* 2017; 218: 1600380.
59. Lian X, Zhang J, Azarin S M, Zhu K, Hazeltine L B, Bao X, Hsiao C, Kamp T J and Palecek S P. Directed cardiomyocyte differentiation from human pluripotent stem cells by modulating Wnt/beta-catenin signaling under fully defined conditions. *Nat Protoc.* 2013; 8:162-75.
60. Kempf H, Kropp C, Olmer R, Martin U and Zweigerdt R. Cardiac differentiation of human pluripotent stem cells in scalable suspension culture. *Nat Protoc.* 2015; 10:1345-61.
61. DeLong S A, Moon J J and West J L. Covalently immobilized gradients of bFGF on hydrogel scaffolds for directed cell migration. *Biomaterials.* 2005; 26:3227-34.
62. Dikovsky D, Bianco-Peled H and Seliktar D. The effect of structural alterations of PEG-fibrinogen hydrogel scaffolds on 3-D cellular morphology and cellular migration. *Biomaterials.* 2006; 27:1496-506.
63. Kinney M A, Hookway T A, Wang Y and McDevitt T C. Engineering three-dimensional stem cell morphogenesis for the development of tissue models and scalable regenerative therapeutics. *Ann Biomed Eng.* 2014; 42:352-67.

Example 4

Droplet Microfluidics-Based Fabrication and Three-Dimensional Culture of PEG-Fibrinogen Breast Cancer Microspheres Three-dimensional (3D) culture of cells within biomimetic and cell-supportive hydrogel matrices provides physiological context and relevancy to encapsulated cells through close recapitulation of native cellular microenvironments.[1,2] Encapsulation of cells within macroscale hydrogel constructs presents certain limitations including macromolecular mass transfer resistance over millimeter-scale diffusion distances and subsequent undesired effects on cell viability and function.[3-5] Hence, various microencapsulation technologies have been developed for the fabrication of hydrogel micro-constructs and subsequent maintenance of cells in 3D culture with high viability and efficient function. Some common microfabrication techniques include droplet microfluidics,[6,7] emulsion-based[8,9] and spray-based[10,11] droplet generation, flow lithography,[12,13] 3D bioprinting,[14,15] amongst others. However, majority of these cellular microencapsulation techniques aim at the creation of hydrogel microparticles, microgels or microbeads of size ranging from sub-micron scale to a few hundred microns. Efficient generation of hydrogel microspheres in the sub-millimeter range is yet to be investigated in depth. Described in this Example is the high-throughput fabrication of uniform hydrogel microspheres (microspheres) comprised of the biosynthetic polymer, poly(ethylene glycol)-fibrinogen (PF) and subsequent 3D culture of encapsulated breast cancer cells.

Numerous biomimetic polymers have been previously employed for the controlled generation of hydrogel microstructures including collagen,[16] alginate,[17] poly(lactic-co-glycolic acid) (PLGA),[18] chitosan,[19] and peptide-conjugated poly(ethylene glycol) diacrylate (PEGDA)[8,20]. However, the use of PF as a potential ECM-mimicking matrix for microencapsulation of cells has not yet received wide attention. Previously, we have demonstrated the ability to encapsulate and culture MCF7 breast cancer cells within millimeter-scale PEGDA hydrogel millibeads obtained via a surface tension-based, dual-phase crosslinking technique.[4] However, PEGDA, being non-bioactive, is limited in providing physiological context to encapsulated cells and could potentially lead to low cell viability over time. As an improvement, PF hydrogel, being cell-permissive, facilitates closer recapitulation of native cellular presentation and function in 3D culture.[21-23]

In this Example, the ability to generate uniform PF hydrogel microspheres of considerably larger size range (compared to that reported in previous studies) and in a high-throughput manner is demonstrated. Further, the 3D culture of two breast cancer cell lines and subsequent investigation of cellular morphology, ultrastructure, bulk matrix stiffness and metabolic activity is also presented. The cancer microsphere platform established in this study has the potential to be translated to high-throughput platforms for testing efficacies of novel anticancer therapeutics and for eventual validation studies in the drug discovery process.

Results for this Example

Figure 27:
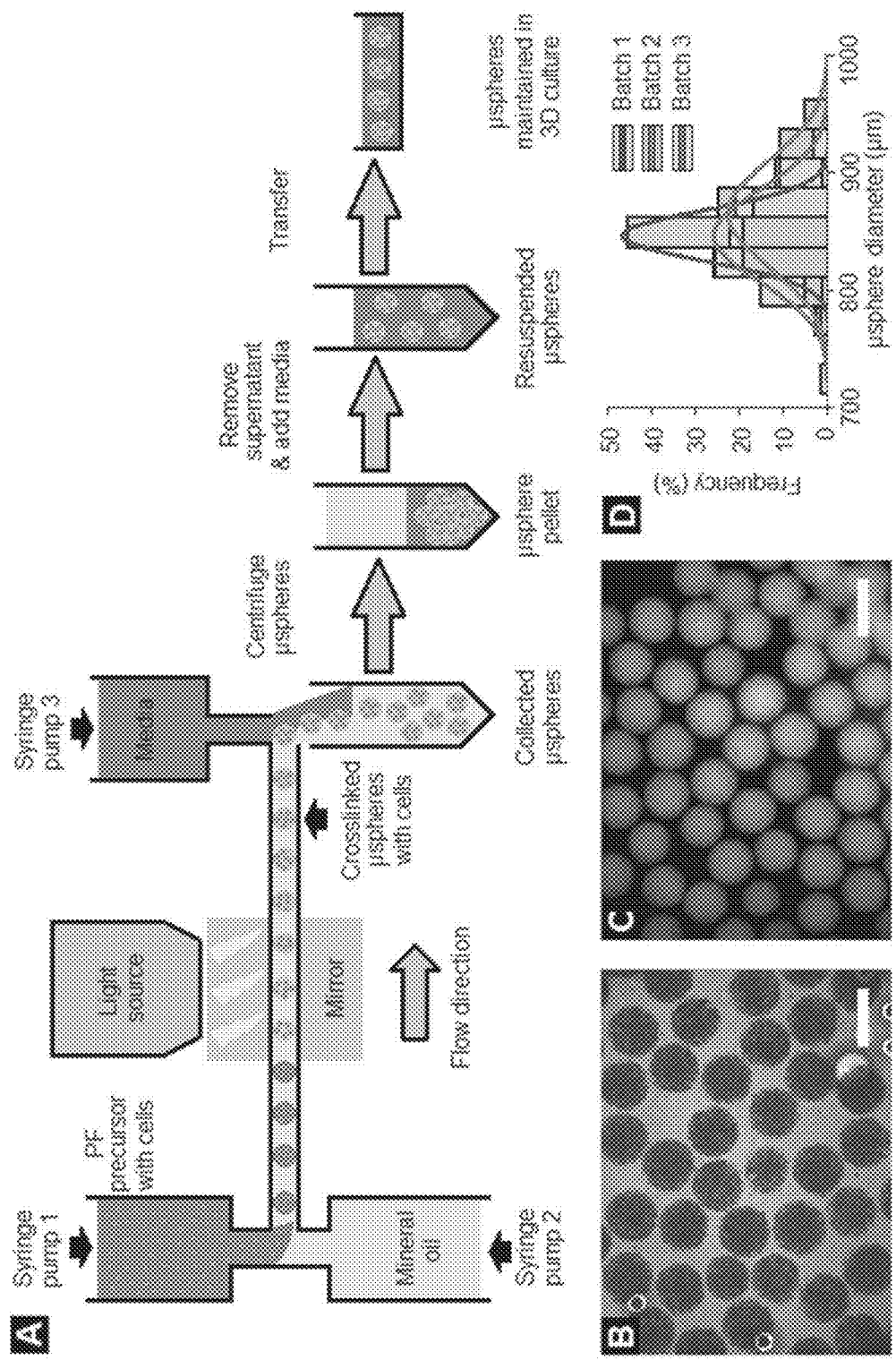
FIGS. 27A-27D. Microfluidic fabrication and size characterization of PF microspheres.

Fabrication of Cell-Laden PF Microspheres:

In order to fabricate uniform and consistent PEG-fibrinogen (PF) hydrogel microspheres, a microfluidic platform employing an aqueous-oil dual-phase system was established. Poly(dimethyl siloxane) (PDMS) was used to construct a T-junction with a channel diameter of 900 µm and a channel length of 10 cm. The two inlet ends of the T-junction were connected to syringes containing the cell-laden PF hydrogel precursor (syringe pump 1) and mineral oil (syringe pump 2) respectively. The hydrogel precursor was obtained by mixing the aqueous PF solution in phosphate buffered saline (PBS) with Eosin Y (1 mM) as the photoinitiator, triethanolamine (TEOA) (1.5% v/v) as co-initiator, 1-vinyl 2-pyrrolidinone (NVP) (37 mM) as co-monomer and Pluronic F68 (10% w/v in PBS) as surfactant for the generation of uniform microspheres. Cancer cells were resuspended in the precursor at $20 \times 10^6$ cells/ml. As an interesting operational feature, the initial cell encapsulation density within the hydrogel precursor can be varied from $5 \times 10^6$ cell/ml to $60 \times 10^6$ cells/ml without affecting the photocrosslinking efficiency of the polymer precursor or uniformity of hydrogel microsphere size distribution. A broad spectrum light source (2.7 W) was positioned midway over the channel and fitted with a mirror behind the channel for reflecting light within a distance of approximately 0.5 cm (FIG. 27A). Optimization of aqueous phase flowrate to 1 mL/hr and oil phase flowrate to 10 mL/hr resulted in uniformly crosslinked microspheres in the size range of 750-950 µm in diameter. The end of the microfluidic channel was connected to a third syringe pump containing media to collect and wash off crosslinked microspheres and to prevent them from accumulating at the channel end. The cell-laden PF microspheres were centrifuged and supernatant oil layer was aspirated. The microspheres were resuspended in media and maintained in 3D culture over 14 days.

Phase contrast and fluorescence visualization of crosslinked microspheres revealed an overall uniform appearance and size distribution of microspheres. Encapsulated cells were also observed to be uniformly distributed within individual microspheres (FIG. 27B, 27C). Further quantification of microspheres immediately post-fabrication revealed high degree of inter-batch and intra-batch uniformity and low coefficient of variation (COV) with majority of microspheres within 800-900 µm in diameter (Batch 1: Average diameter=847 µm, COV=2.51; Batch 2: Average diameter=866 µm, COV=5.05; Batch 3: Average diameter=847 µm, COV=4.53) (FIG. 27D). Overall, the established microfluidic system was able to facilitate the high-throughput generation of uniform cell-laden PF hydrogel microspheres for subsequent 3D breast cancer cell culture and investigation of 3D cell behavior.

Figure 28:
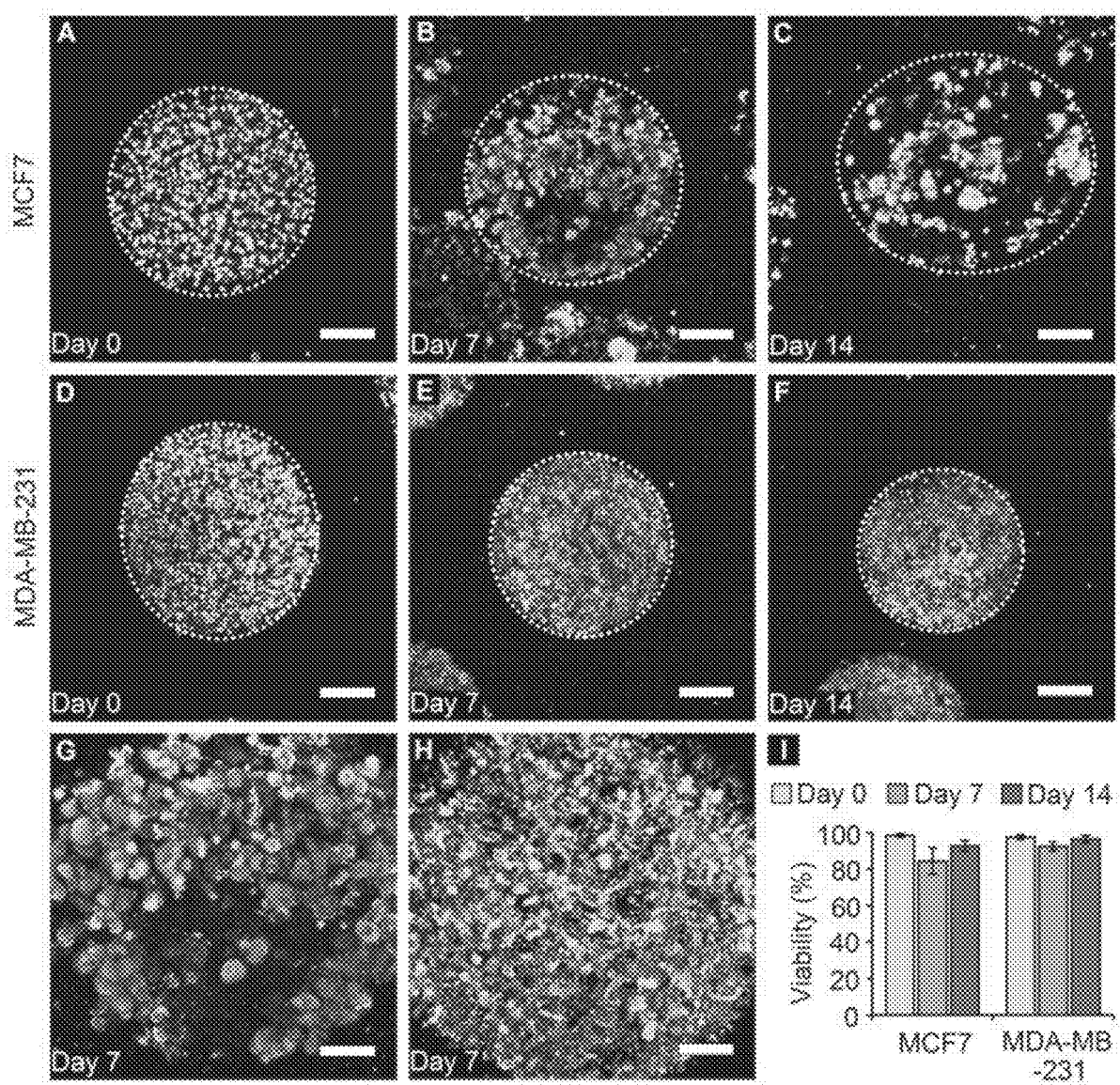
FIGS. 28A-28I. Cancer cell viability within PF microspheres.

Assessment of Cell Viability within PF Microspheres:

Post microsphere fabrication and cell encapsulation, the ability to maintain breast cancer cells in 3D culture within the PF hydrogel microspheres over 2 weeks was demonstrated. The cell viability for both MCF7 and MDA-MB-231 breast cancer cells was visualized and assessed via fluorescence staining and confocal imaging on day 0 (few hours post encapsulation), day 7 and day 14 (FIG. 28A-28F). Cell viability for both cell types on day 0 was found to be greater than 95% (FIG. 28A, 28D, 28I), indicating that the microfluidic fabrication technique (including the use of UV light source) did not have any significant impact on cell viability. In general, high viability was maintained for both cell types through 14 days in culture (>90%), except for MCF7 cells, which displayed a slight drop in viability to 84% on day 7 (FIG. 28I). Closer inspection of encapsulated cells revealed that MCF7 cells grew as local dense colonies or clusters within the microspheres (FIG. 28G) while MDA-MB-231 cells appeared to spread out and occupy the void space within the microspheres without any tendency of cluster formation (FIG. 28H). In all, the ability to encapsulate breast cancer cells within PF hydrogel microspheres and maintain them with high viability in 3D culture over time was demonstrated.

Figure 29:
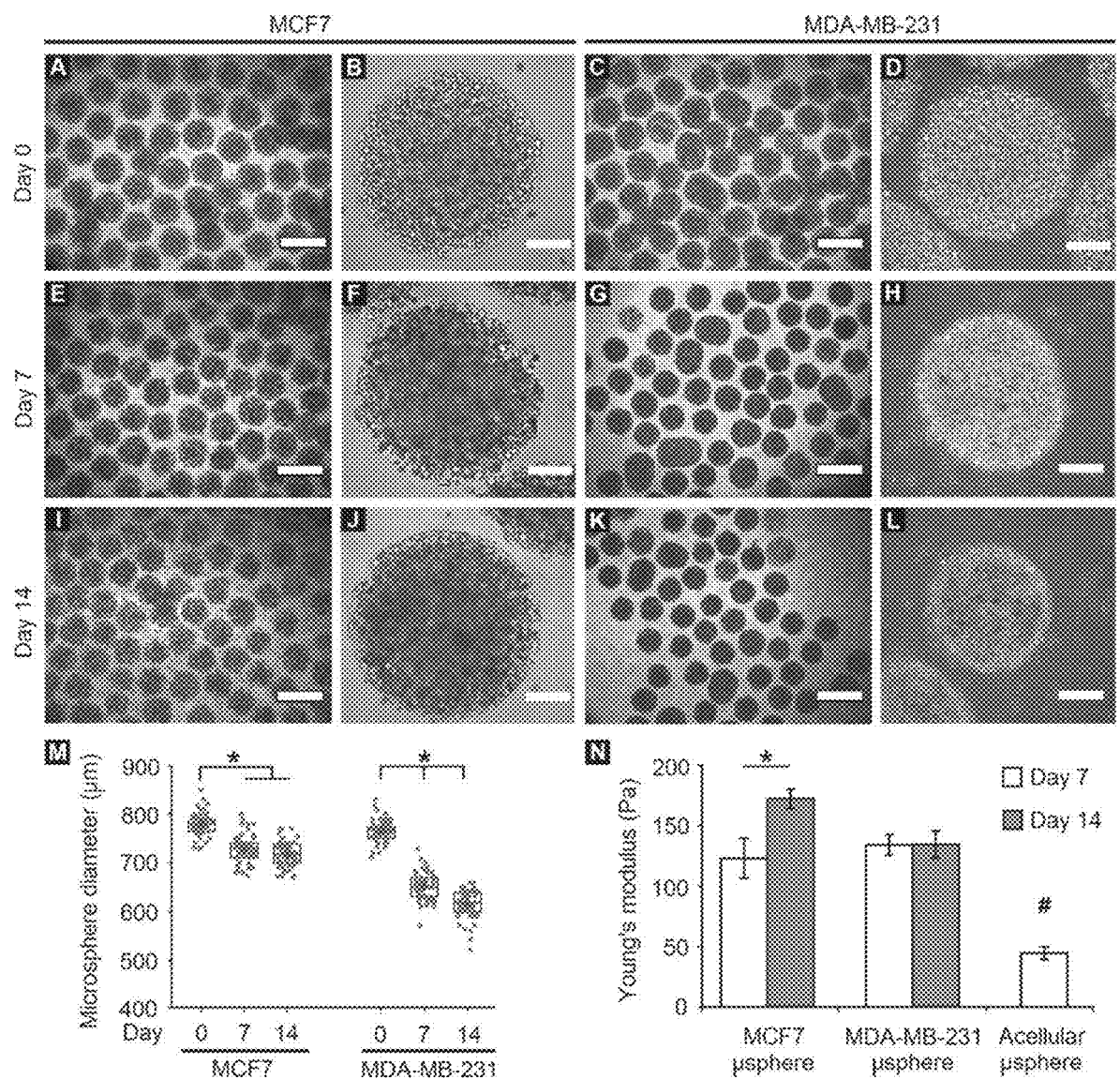

Characterization of PF Microsphere Diameter, Stiffness and Cellular Metabolic Activity:

Having established the ability to maintain cancer cells within PF hydrogel microspheres, further characterization of the changes in microsphere size and stiffness over time was conducted. When visualized through phase contrast microscopy, MCF7 cells (shown in FIGS. 29A, 29B, 29E, 29F, 29I, and 29J) appeared to form dense local colonies arising from single encapsulated cells; these colonies grew darker over time indicating progressional cell growth. In contrast, MDA-MB-231 cells (shown in FIGS. 29C, 29D, 29G, 29H, 29K, 29L) appeared to form elongated morphologies within the microspheres over time. Interestingly, a sharp decrease in diameter was observed for MDA-MB-231 microspheres through 14 days in culture, possibly due to contractile stresses exerted by elongated cells on the PF hydrogel matrix. Quantification of microsphere diameter confirmed these observations (FIG. 29M). In case of MCF7 cells, microsphere diameter was significantly reduced from 0 (Average: 779±23 µm) to day 7 (Average: 726±28 µm) and remained fairly steady thereafter. In case of MDA-MB-231 cells, microsphere diameter progressively decreased from day 0 (Average: 765±22 µm) to day 14 (Average: 613±28 µm) of culture.

In order to assess the effect of cell encapsulation and varying cellular morphology on the stiffness of PF hydrogel microspheres, the Young's moduli of cellular and acellular microspheres was quantified via parallel-plate compression testing. Young's moduli of MCF7 microspheres increased significantly from day 7 (123±16 Pa) to day 14 (172±8 Pa), while that of MDA-MB-231 microspheres remained constant over time (~134±10 Pa). Interestingly, the Young's moduli of acellular microspheres (45±5 Pa) was significantly less than cell-encapsulated microspheres for any given time point, indicating the influential role played by encapsulated cancer cells on the bulk stiffness of PF hydrogel microspheres (FIG. 29N).

Figure 30:
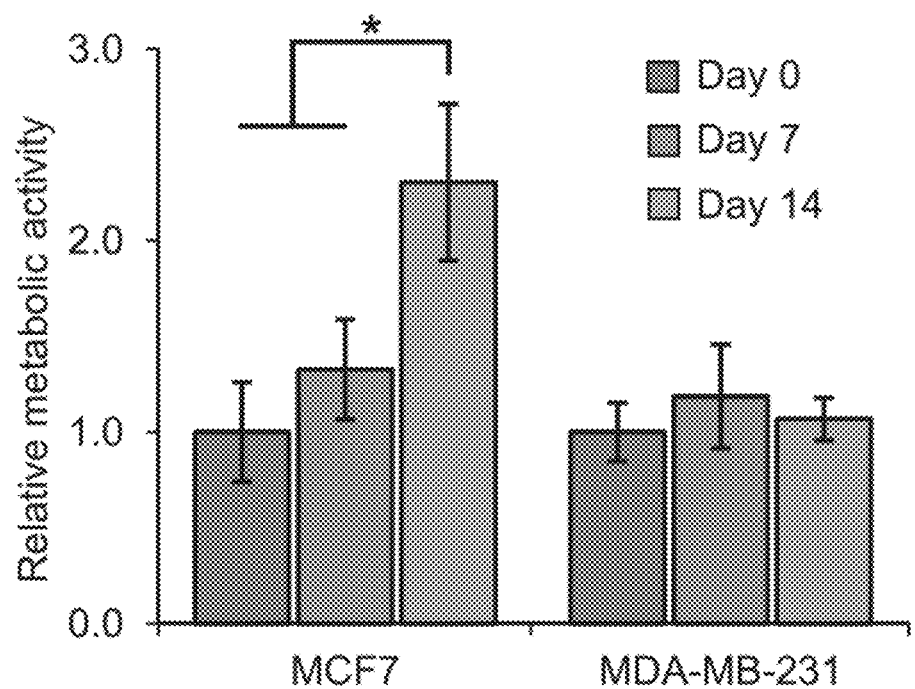
FIG. 30. Metabolic activity of cancer cells within PF microspheres. MCF7 cells display increasing metabolic activity through 14 days with significantly higher activity on day 14. MDA-MB-231 cells display fairly steady metabolic activity through 14 days in culture. All values are normalized to day 0 values for each cell type. (*p<0.05, n=5 microspheres per group).

Further assessment of the relative changes in metabolic activity of encapsulated cells within PF hydrogel microspheres through 14 days in culture was conducted using the XTT assay (FIG. 30). MCF7 cells displayed increasing relative metabolic activity through 14 days with significantly high activity on day 14, possibly due to cell proliferation and increasing local colony formation. However, metabolic activity of MDA-MB-231 cells remained fairly constant over time, indicating potential metabolic quiescent or non-proliferative behavior of this cell type within PF hydrogel microspheres.

Overall, the encapsulation of cancer cells within PF hydrogel microspheres resulted in gradual changes in microsphere size, stiffness and metabolic activity over time, which were modulated by cell-type dependent morphology, 3D cell behavior and potential cell-PF hydrogel matrix interactions.

Figure 31:
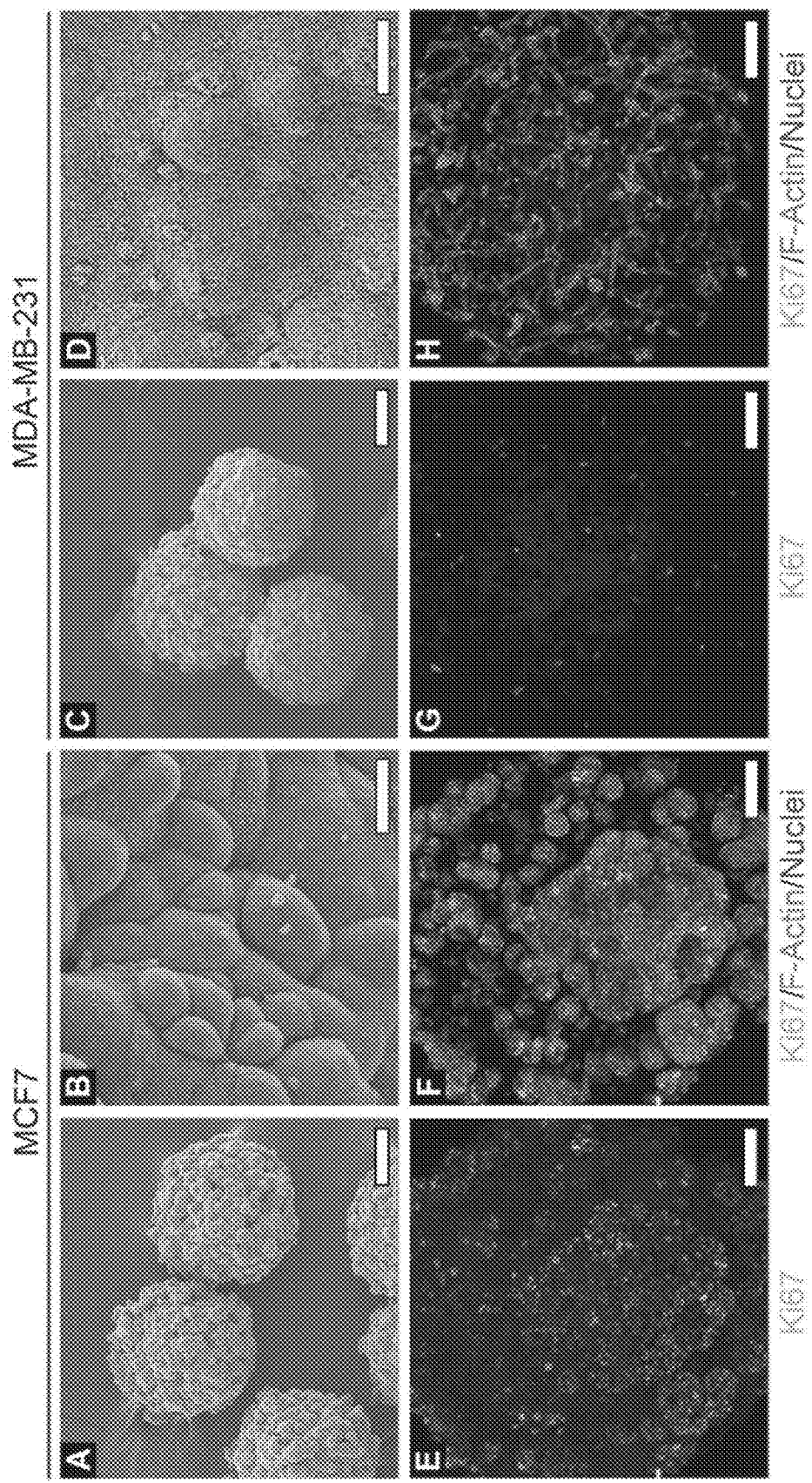
FIGS. 31A-31H. Ultrastructure and 3D morphology of cancer cells within PF microspheres.

Visualization of Cellular Ultrastructure and 3D Morphology in PF Microspheres:

In order to visualize the ultrastructural surface features of cancer cells encapsulated within PF hydrogel microspheres, scanning electron microscopy (SEM) imaging was conducted on cell-laden microspheres. SEM images of MCF7 microspheres revealed dense local colony formation with spherical shaped colonies being distributed throughout the microsphere surface (FIG. 31A). Closer inspection revealed the dense packing of MCF7 cells with tight cellular interactions within individual colonies and microvilli-like features present on the cell surface (FIG. 31B). MDA-MB-231 microspheres displayed different ultrastructural features compared to MCF7 microspheres (FIG. 31C). MDA-MB-231 cells appeared as individual cells and interspersed within the mesh-like PF hydrogel matrix (FIG. 31D).

The 3D morphology and cellular arrangement of cancer cells within PF hydrogel microspheres was further visualized by fluorescence staining and confocal imaging. MCF7 microspheres revealed a higher degree of Ki67 positive staining compared to MDA-MB-231 microspheres (FIG. 31E, 31G), indicating higher cell proliferation in MCF7 cells. This observation also correlates with the previous assessment of cellular metabolic activity in FIG. 30. MCF7 cells presented a rounded morphology (as observed through F-actin arrangement) and appeared to grow as distinct local colonies with tight cell packing and distributed uniformly within the microspheres (FIG. 31F). However, MDA-MB-231 cells presented elongated morphologies with high degree of cellular projections and filopodial extensions (FIG. 31H), reminiscent of their migratory and invasive behavior.

In general, breast cancer cells encapsulated within PF hydrogel microspheres displayed cell-type dependent differences in ultrastructural and morphological characteristics. These differences reveal important insights into 3D cell behavior under the synergistic influence of cell-cell and cell-matrix interactions within PF hydrogel microspheres.

REFERENCES CITED IN THIS EXAMPLE

1. D. Seliktar, *Science*, 2012, 336, 1124-1128.
2. S. Pradhan, I. Hassani, J. M. Clary and E. A. Lipke, *Tissue engineering. Part B, Reviews*, 2016, DOI: 10.1089/ten.TEB.2015.0567.
3. G. D. Nicodemus and S. J. Bryant, *Tissue engineering. Part B, Reviews*, 2008, 14, 149-165.
4. S. Pradhan, C. S. Chaudhury and E. A. Lipke, *Langmuir*, 2014, 30, 3817-3825.
5. Y. Ling, J. Rubin, Y. Deng, C. Huang, U. Demirci, J. M. Karp and A. Khademhosseini, *Lab on a Chip*, 2007, 7, 756-762.
6. S. Y. Teh, R. Lin, L. H. Hung and A. P. Lee, *Lab on a Chip*, 2008, 8, 198-220.
7. M. T. Guo, A. Rotem, J. A. Heyman and D. A. Weitz, *Lab on a Chip*, 2012, 12, 2146-2155.
8. C. L. Franco, J. Price and J. L. West, *Acta biomaterialia*, 2011, 7, 3267-3276.
9. R. M. Olabisi, Z. W. Lazard, C. L. Franco, M. A. Hall, S. K. Kwon, E. M. Sevick-Muraca, J. A. Hipp, A. R. Davis, E. A. Olmsted-Davis and J. L. West, *Tissue engineering. Part A*, 2010, 16, 3727-3736.
10. M. B. Oliveira, O. Kossover, J. F. Mano and D. Seliktar, *Acta biomaterialia*, 2015, 13, 78-87.
11. Y. C. Lu, W. Song, D. An, B. J. Kim, R. Schwartz, M. Wu and M. Ma, *Journal of Materials Chemistry B*, 2015, 3, 353-360.
12. P. Panda, S. Ali, E. Lo, B. G. Chung, T. A. Hatton, A. Khademhosseini and P. S. Doyle, *Lab on a Chip*, 2008, 8, 1056-1061.
13. D. Dendukuri, D. C. Pregibon, J. Collins, T. A. Hatton and P. S. Doyle, *Nat Mater*, 2006, 5, 365-369.
14. L. E. Bertassoni, J. C. Cardoso, V. Manoharan, A. L. Cristino, N. S. Bhise, W. A. Araujo, P. Zorlutuna, N. E. Vrana, A. M. Ghaemmaghami, M. R. Dokmeci and A. Khademhosseini, *Biofabrication*, 2014, 6, 024105.
15. K. Pataky, T. Braschler, A. Negro, P. Renaud, M. P. Lutolf and J. Brugger, *Advanced Materials*, 2012, 24, 391-396.
16. N. Nagai, N. Kumasaka, T. Kawashima, H. Kaji, M. Nishizawa and T. Abe, *Journal of Materials Science: Materials in Medicine*, 2010, 21, 1891-1898.
17. K. S. Huang, T. H. Lai and Y. C. Lin, *Lab on a Chip*, 2006, 6, 954-957.
18. J. Wu, T. Kong, K. W. K. Yeung, H. C. Shum, K. M. C. Cheung, L. Wang and M. K. T. To, *Acta biomaterialia*, 2013, 9, 7410-7419.
19. N. B. Skop, F. Calderon, S. W. Levison, C. D. Gandhi and C. H. Cho, *Acta biomaterialia*, 2013, 9, 6834-6843.
20. N. A. Impellitteri, M. W. Toepke, S. K. Lan Levengood and W. L. Murphy, *Biomaterials*, 2012, 33, 3475-3484.
21. P. Kerscher, I. C. Turnbull, A. J. Hodge, J. Kim, D. Seliktar, C. J. Easley, K. D. Costa and E. A. Lipke, *Biomaterials*, 2016, 83, 383-395.
22. R. K. Singh, D. Seliktar and A. J. Putnam, *Biomaterials*, 2013, 34, 9331-9340.
23. L. Almany and D. Seliktar, *Biomaterials*, 2005, 26, 2467-2477.

Example 5

Varying the Aspect Ratio of the Microparticles can Affect Cellular Function

Figure 32:
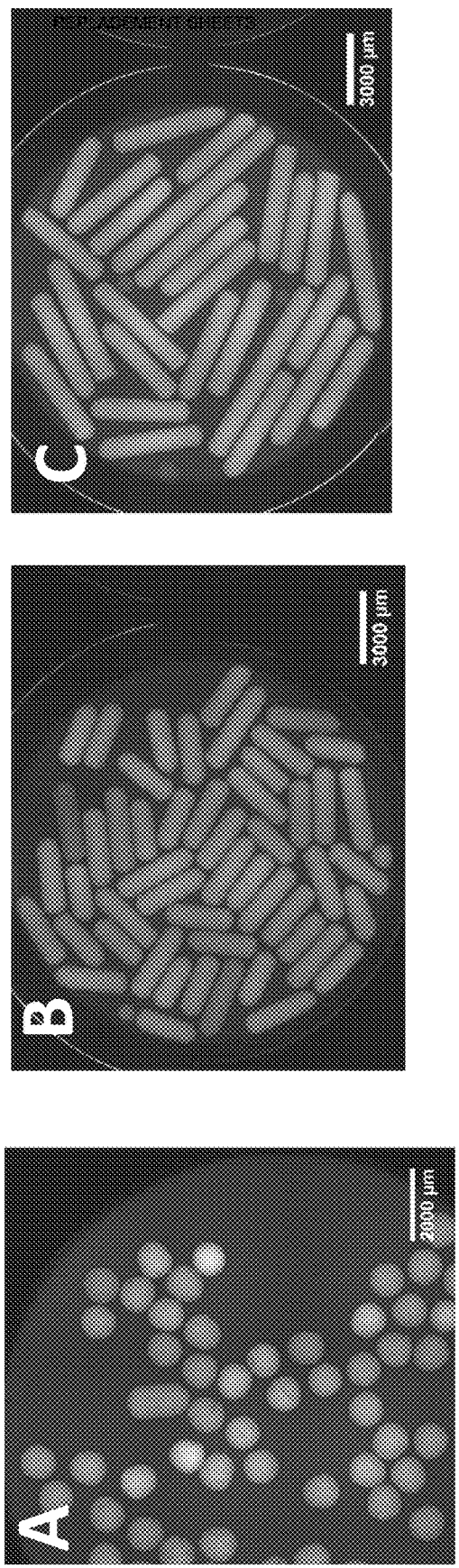
FIG. 32A-32E show microparticle variation resulting from altering the polymer precursor flow rate while holding the oil flow rate constant.
Figure 32:
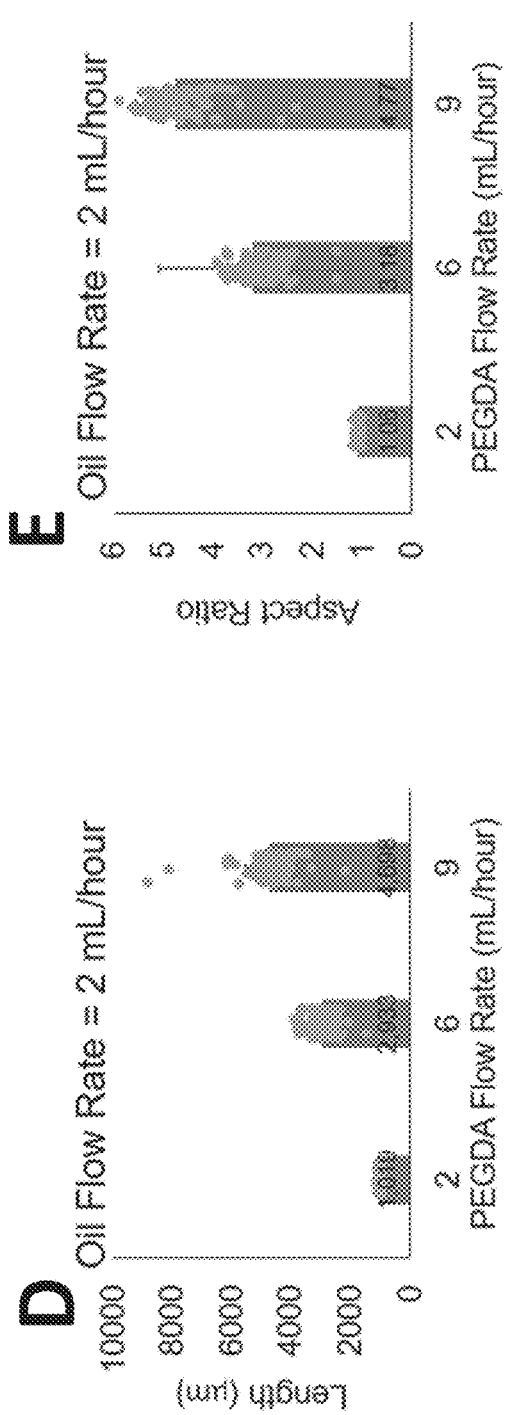
Figure 33:
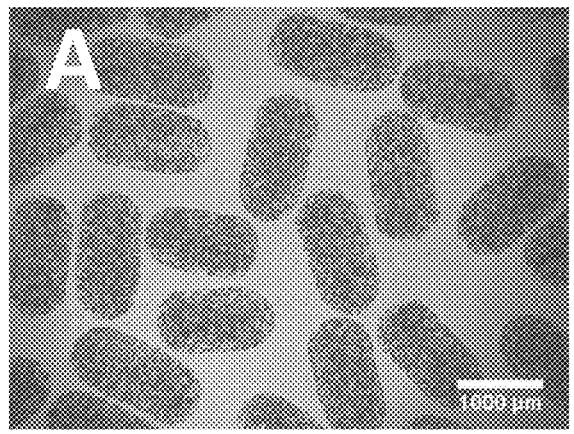
FIGS. 33A-33F show cell encapsulation in elongated microparticles.
Figure 33:
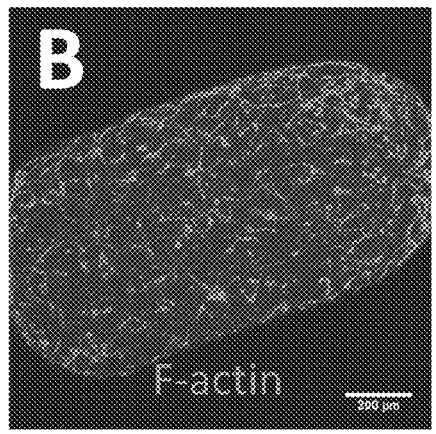
Figure 33:
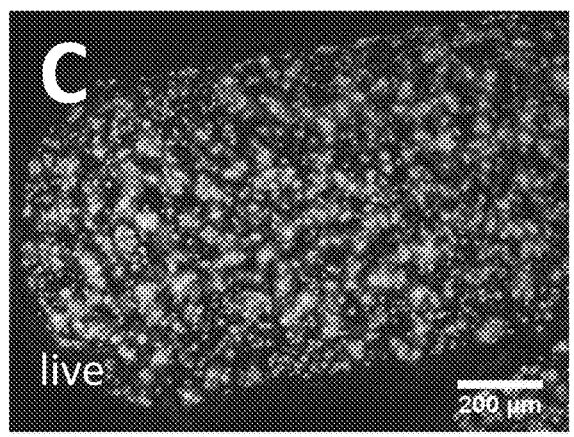
Figure 33:
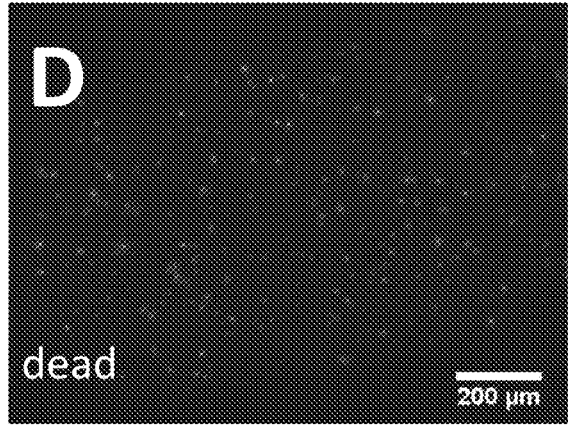
Figure 33:
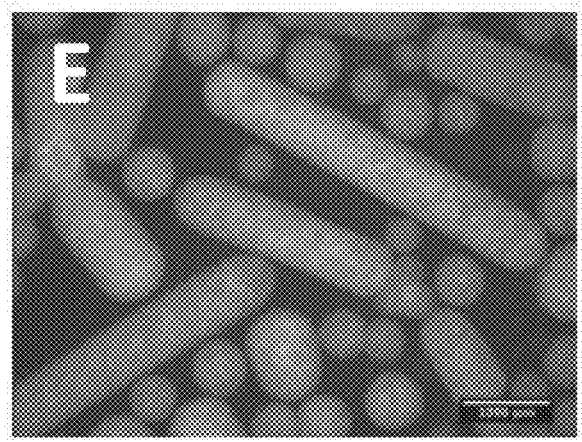
Figure 33:
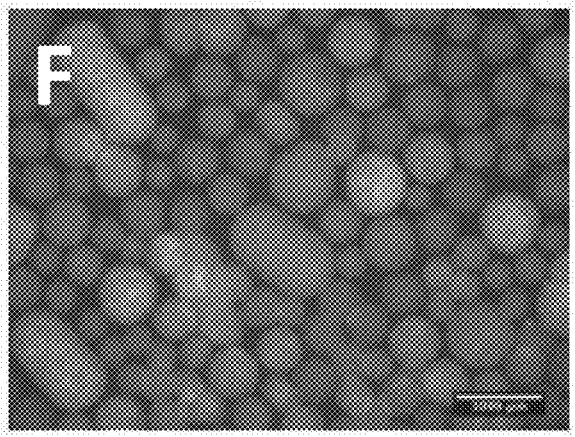
Figure 34:
FIGS. 34A-34C are graphs showing functional variation in cardiomyocytes encapsulated in microparticles of varying aspect ratios.
Figure 35:
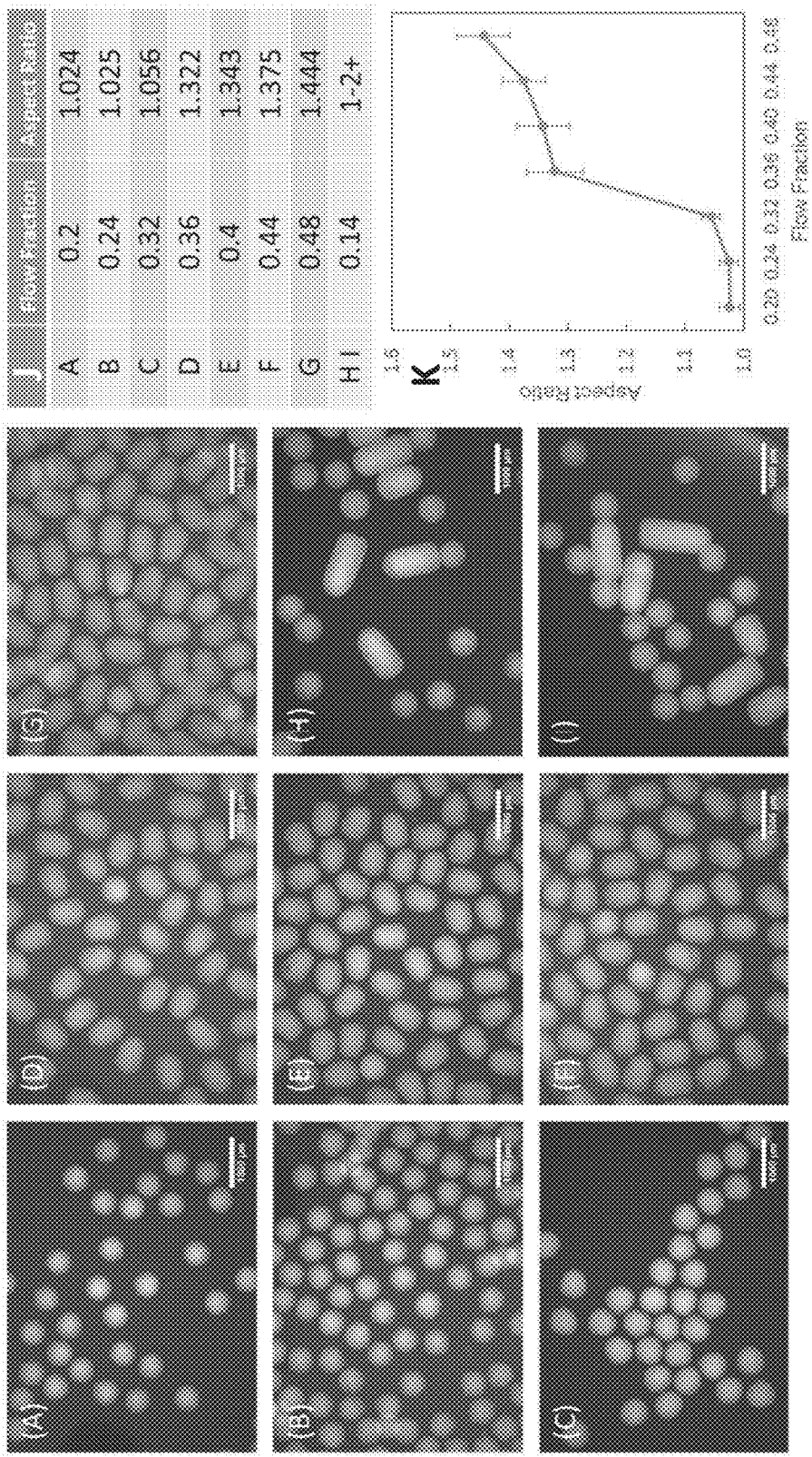
FIGS. 35A-35K show the results of a study on varying aspect ratio of microparticles.

Varying the precursor flow rate with respect to the oil flow rate can affect the aspect ratio of the resulting microparticles, as shown in FIGS. 32A-32E. FIG. 32A shows fluorescent images of microparticles resulting from an oil flow rate of 2 mL/hour with a corresponding PEGDA flow rate of 2 mL per hour. FIGS. 32B and 32C show microparticles resulting from an oil flow rate of 2 mL/hour with a corresponding PEGDA flow rate of 6 mL/hour and 9 mL/hour, respectively. As shown in FIGS. 32D and 32E, increasing the polymer precursor flow rate while keeping the oil flow rate constant increases the length and the aspect ratio of the resulting microparticles (high aspect ratio indicates longer microparticles). Microparticles having a high aspect ratio can be formed across a range of transverse radii (for example, from about 200 micrometers to about 1,000 micrometers. Fibroblasts encapsulated in microparticles (FIG. 33A) stain positively for F-actin (FIG. 33B) and have high viability after encapsulation, as demonstrated by live-dead staining (FIGS. 33C and 33D, live-dead staining method described in Example 1). It was also possible to encapsulate hiPSCs in elongated microparticles having high aspect ratios (FIG. 33E) and of lower aspect ratios (FIG. 33F). Interestingly, cardiomyocytes encapsulated in elongated microparticles show variation in functional activity that corresponds to the aspect ratio of the microparticles (FIGS. 34A-34C). While beat rate remains unchanged (FIG. 34A), the maximum contraction velocity (FIG. 34B) and the maximum relaxation velocity (FIG. 34C) appear to increase with increasing aspect ratio. FIGS. 35A-35I show microparticles formed by varying the flow ratio of the device (described in detailed description). FIG. 35J and FIG. 35K show the effects of varying flow fraction on aspect ratio.

Those skilled in the art will recognize, or be able to ascertain using no more than routine experimentation, many equivalents to the specific embodiments of the invention described herein. While the invention has been described with reference to particular embodiments and implementations, it will understood that various changes and additional variations may be made and equivalents may be substituted for elements thereof without departing from the scope of the invention or the inventive concept thereof. In addition, many modifications may be made to adapt a particular situation or device to the teachings of the invention without departing from the essential scope thereof. Such equivalents are intended to be encompassed by the following claims. It is intended that the invention not be limited to the particular implementations disclosed herein, but that the invention will include all implementations falling within the scope of the appended claims.

Unless defined otherwise, all technical and scientific terms used herein have the same meanings as commonly understood by one of skill in the art to which the disclosed invention belongs. Publications cited herein and the materials for which they are cited are specifically incorporated by reference.

REFERENCES CITED IN BACKGROUND SECTION

Dini, E., Alexandridou, S. and Kiparissides, C. Synthesis and characterization of cross-linked chitosan microspheres for drug delivery applications. *Journal of Microencapsulation* 2003; 20(3):375-385.

Franco, C. L., Price, J. and West, J. L. Development and optimization of a dual-photoinitiator, emulsion-based technique for rapid generation of cell-laden hydrogel microspheres. *Acta* Biomaterialia 2011; 7(9):3267-3276.

Headen, D. M., et al. Microfluidic-Based Generation of Size-Controlled, Biofunctionalized Synthetic Polymer Microgels for Cell Encapsulation. Advanced Materials 2014; 26(19):3003-3008.

Horning, J. L., et al. 3-D tumor model for in vitro evaluation of anticancer drugs. Molecular Pharmaceutics 2008; 5(5): 849-862.

Khademhosseini, A. and Langer, R. Microengineered hydrogels for tissue engineering. Biomaterials 2007; 28(34): 5087-5092.

King, T. W. and Patrick, C. W. Development and in vitro characterization of vascular endothelial growth factor (VEGF)-loaded poly(DL-lactic-co-glycolic acid)/poly (ethylene glycol) microspheres using a solid encapsulation/single emulsion/solvent extraction technique. *Journal of Biomedical Materials Research* 2000; 51(3):383-390.

Leong, W. Y. and Wang, D. A. Cell-laden Polymeric Microspheres for Biomedical Applications. Trends in Biotechnology 2015; 33(11):653-666.

Lutolf, M. P. and Hubbell, J. A. Synthetic biomaterials as instructive extracellular microenvironments for morphogenesis in tissue engineering. Nature Biotechnology 2005; 23(1):47-55.

Pradhan, S., et al. A three-dimensional spheroidal cancer model based on PEG-fibrinogen hydrogel microspheres. Biomaterials 2017; 115:141-154.

Seeto, W. J., et al. Encapsulation of Equine Endothelial Colony Forming Cells in Highly Uniform, Injectable Hydrogel Microspheres for Local Cell Delivery. Tissue Engineering Part C-Methods 2017; 23(11):815-825.

Shofuda, T., et al. A method for efficiently generating neurospheres from human-induced pluripotent stem cells using microsphere arrays. Neuroreport 2013; 24(2):84-90.

Tashiro, S., Tsumoto, K. and Sano, E. Establishment of a microcarrier culture system with serial sub-cultivation for functionally active human endothelial cells. *Journal of Biotechnology* 2012; 160(3-4): 202-213.

Tree, J. A., et al. Comparison of large-scale mammalian cell culture systems with egg culture for the production of influenza virus A vaccine strains. Vaccine 2001; 19(25-26): 3444-3450.

Van Den Bulcke, A. I., et al. Structural and rheological properties of methacrylamide modified gelatin hydrogels. *Biomacromolecules* 2000; 1 (1): 31-38.

Velasco, D., Tumarkin, E. and Kumacheva, E. Microfluidic Encapsulation of Cells in Polymer Microgels. Small 2012; 8(11):1633-1642.

Yang, Y. Y., Chung, T. S. and Ng, N. P. Morphology, drug distribution, and in vitro release profiles of biodegradable polymeric microspheres containing protein fabricated by double-emulsion solvent extraction/evaporation method. Biomaterials 2001; 22(3):231-241.

Yao, R., et al. Injectable cell/hydrogel microspheres induce the formation of fat lobule-like microtissues and vascularized adipose tissue regeneration. *Biofabrication* 2012; 4(4).

What is claimed is:

1. A device for encapsulating cells within microparticles, the device comprising:
    a housing, the housing comprising a horizontal plane extending through the housing and a vertical plane extending through the housing,
    a first inlet port positioned on an upper surface of the housing, adjacent a first side surface,
    a first inlet channel in fluid communication with the first inlet port, the first inlet channel extending through the housing at an angle to the horizontal plane,
    a second inlet port positioned on a lower surface of the housing, adjacent the first side surface,
    a second inlet channel in fluid communication with the second inlet port and positioned below the first inlet channel, the second inlet channel extending through the housing at an angle to the horizontal plane and meeting the first inlet channel at a junction, and
    an outlet channel in fluid communication with the first and second inlet channels, the outlet channel extending away from the first and second inlet channels, through the housing, and to an outlet port on a second side surface of the housing.

2. The device of claim 1, further comprising a mirror coupled to the housing and configured to reflect light through the outlet channel.

3. The device of claim 1, wherein the first inlet channel, the second inlet channel, or both extend parallel to the vertical plane.

4. The device of claim 1, wherein the first and second inlet channels each have narrowed diameter adjacent the junction.

5. The device of claim 4, wherein the first inlet channel narrows in a stepwise fashion and the second inlet channel narrows in a tapered fashion.

6. The device of claim 1, wherein the outlet channel is perpendicular to the first inlet channel, the second inlet channel, or both.

7. The device of claim 1, wherein the width of the outlet channel increases as it extends away from the first and second inlet channels.

8. The device of claim 1, wherein the outlet channel extends a distance of from 5 centimeters to 20 centimeters before reaching the outlet port on the second side surface of the device.

9. The device of claim 1, wherein the outlet channel is cylindrical along at least a portion of the length of the device.

10. The device of claim 1, wherein the housing is formed within an elongated rectangular bracket and around an arrangement of tubing and wires.

11. A method of making microparticles, the method comprising:
  flowing a hydrophilic polymer precursor solution down through a first inlet port positioned on an upper surface of a housing, adjacent a first side surface of the housing;
  flowing the hydrophilic polymer precursor solution down through a first inlet channel that extends at an angle to a horizontal plane extending through the housing;
  flowing a hydrophobic fluid up through a second inlet port positioned on a lower surface of the housing, adjacent the first side surface;
  flowing the hydrophobic fluid up through a second inlet channel that is positioned below the first inlet channel and extends at an angle to the horizontal plane;
  bringing the hydrophilic polymer precursor solution into contact with the hydrophobic fluid at a junction of the first inlet channel and the second inlet channel;
  flowing the hydrophilic polymer precursor solution and the hydrophobic fluid together through an outlet channel;
  dispersing the hydrophilic polymer precursor solution within the outlet channel using the upwardly moving hydrophobic fluid;
  polymerizing the dispersed hydrophilic polymer precursor solution into microparticles within the outlet channel; and
  ejecting the microparticles from an outlet port on a second side surface of the housing.

12. The method of claim 11, further comprising generating cell-laden microparticles by suspending cells in the hydrophilic polymer precursor solution at a cell density from 10 million cells/milliliter to 60 million cells/milliliter prior to flowing the hydrophilic polymer precursor solution through the first inlet channel.

13. The method of claim 11, wherein the formed microparticles range in size from 100 micrometers to 1,000 micrometers across a largest dimension.

14. The method of claim 13, wherein the microparticles are formed at a rate of from 3,500 to 35,000 microparticles per hour.

15. The method of claim 11, wherein polymerizing the dispersed hydrophilic polymer precursor solution into microparticles comprises photopolymerizing the hydrophilic polymer precursor solution within the outlet channel for a time period of greater than 1 second.

16. The method of claim 15, wherein photopolymerizing the hydrophilic polymer precursor solution further comprises transmitting light from an initial light source through the outlet channel, and reflecting the transmitted light off of a mirror and back through the outlet channel.

17. The method of claim 11, further comprising running a wash fluid over the outlet port.

* * * * *